(12) United States Patent
Schwarz et al.

(10) Patent No.: US 8,173,597 B2
(45) Date of Patent: May 8, 2012

(54) MODIFIED RECOMBINANT FACTOR VIII AND VON WILLEBRAND FACTOR AND METHODS OF USE

(75) Inventors: Hans-Peter Schwarz, Vienna (AT); Peter Turecek, Klosterneuburg (AT)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 552 days.

(21) Appl. No.: 12/267,491

(22) Filed: Nov. 7, 2008

(65) Prior Publication Data
US 2009/0247459 A1 Oct. 1, 2009

Related U.S. Application Data

(60) Provisional application No. 60/986,975, filed on Nov. 9, 2007.

(51) Int. Cl.
*A61K 38/37* (2006.01)
*C07K 14/775* (2006.01)
(52) U.S. Cl. .................. 514/14.1; 525/54.1; 530/383
(58) Field of Classification Search .................. None
See application file for complete search history.

(56) References Cited

U.S. PATENT DOCUMENTS

| | | | |
|---|---|---|---|
| 5,672,662 | A | 9/1997 | Harris et al. |
| 6,037,452 | A | 3/2000 | Minamino et al. |
| 7,060,259 | B2 | 6/2006 | Bentley et al. |
| 2004/0235723 | A1 | 11/2004 | Albersheim et al. |
| 2004/0235734 | A1 | 11/2004 | Bossard et al. |
| 2005/0009988 | A1 | 1/2005 | Harris et al. |
| 2005/0079155 | A1 | 4/2005 | Marshall |
| 2006/0115876 | A1 | 6/2006 | Pan et al. |
| 2006/0160948 | A1 | 7/2006 | Scheiflinger et al. |
| 2006/0171920 | A1 | 8/2006 | Shechter et al. |
| 2006/0293499 | A1 | 12/2006 | Bentley et al. |
| 2008/0058504 | A1 | 3/2008 | Bossard et al. |

FOREIGN PATENT DOCUMENTS

| | | | |
|---|---|---|---|
| WO | WO 2004/029280 | A2 | 4/2004 |
| WO | WO 2004/029280 | A3 | 4/2004 |
| WO | WO 2004/089280 | A2 | 10/2004 |
| WO | WO 2004/089280 | A3 | 10/2004 |
| WO | WO 2006/053299 | A2 | 5/2006 |
| WO | WO 2007/126808 | A1 | 11/2007 |
| WO | WO 2008/082669 | A2 | 7/2008 |

OTHER PUBLICATIONS

Denis, C.V. et al., "Clearance of von Willebrand factor," *Thromb. and Haemost.*, 2008, vol. 99, pp. 271-278.
Gregoriadis, G. et al., "Polysialylated proteins, An approach to improving enzyme stability and half-life in the blood circulation," *STP Pharma Sciences*, 1999, vol. 9, No. 1, pp. 61-66.
Hermanson, G.T., *Bioconjugate Techniques 2nd Edition*, 2008, Academic Press, Inc., Table of Contents Only, 20 pages.
International Search Report mailed on Feb. 9, 2009, for International Application No. PCT/US2008/082888, filed on Nov. 11, 2008, 6 pages.
Peleg-Schulman, T. et al., "Reversible PEGylation: A Novel Technology to Release Native Interferon α2 over a Prolonged Time Period," *Journal of Medicinal Chemistry*, 2004, vol. 47, No. 20, pp. 4897-4904.
Roberts, M.J. et al., "Chemistry for peptide and protein PEGylation," *Advanced Drug Delivery Reviews*, 2002, vol. 54, pp. 459-476.
Rottensteiner, H. et al., "PEGylation or Polysialylation Reduces FVIII Binding to LRP Resulting in Prolonged Half-Life in Murine Models," *ASH Annual Meeting Abstracts*, Nov. 16, 2007, Part 1, vol. 118, Issue 11, Abstract No. 3150, 2 pages.
Schwarz, H.P. et al., "Involvement of low-density lipoprotein receptor-related protein (LRP) in the clearance of factor VIII in von Willebrand factor-deficient mice," *Blood*, Mar. 1, 2000, vol. 95, No. 5, pp. 1703-1708.
Stennicke, H.R. et al., "Generation and biochemical characterization of glycoPEGylated factor VIIa derivatives," *Thrombosis and Haemostatsis*, Nov. 1, 2008, vol. 100, No. 5, pp. 920-928.
Turecek, P.L. et al., "Modification of rVWF with Polysialic Acid: Biochemical and Functional Characterization in Mice with VWD," *Blood*, 2006, vol. 108, No. 11, Abstract 1001, 2 pages.
Turecek, P.L. et al., "PEG Modified rVWF Prolongs the Survival of Native rFVIII in Hemophilia a Knock-Out Mice," *Blood*, 2006, vol. 108, No. 11, Abstract 1002, 2 pages.
Turecek, P.L. et al., "Biochemical and Functional Characterization of Chemically Modified Recombinant von Willebrand Factor (rVWF) as a Carrier Prolonging Survival of rFVIII in Hemophilia a Knock-Out Mice," *J. Thromb. Haemost.*, Jul. 9, 2007, vol. 5, Suppl. 2, Abstract No. O-M-018, 1 page.
Turecek, P.L. et al., "In Vitro and In Vivo Characterization of Full-Length rFVIII Modified with PEG Via Coupling to Primary Amino Groups," *ASH Annual Meeting Abstracts*, Nov. 16, 2007, Part 1, vol. 118, Issue 11, Abstract No. 3147, 2 pages.
P. L. Turecek et al., "Biochemical and Functional Characterization of Chemically Modified Recombinant Von Willebrand Factor (RVWF) as a Carrier Prolonging Survival of RFVIII in Hemophilia a Knock-Out Mice," Jul. 9, 2007, Session: Oral Communications, Haemophilia therapy I, Room A/B (5(2) J. Thromb. Haemost O-M-018 (2007)) Abstract available at: http://www.blackwellpublishing.com/isth2007/abstract.asp?id=64898.
T. Liu et al., "Evaluation of PEG-FVIII Molecules with Prolonged Half-Lives in a Murine FVIII-Dependent Bleeding Model," Jul. 9, 2007, Session: Poster: Factor VIII, Factor V, Exhibition Area (5(2) J. Thromb. Haemost P-M-035 (2007)) Abstract available at: http://www.blackwellpublishing.com/isth2007/abstract.asp?id=65896.
J. E. Murphy et al., "Site-Specific Pegylation of RFVIII Results in Prolonged In Vivo Efficacy," Jul. 10, 2007, Session: Poster: Factor VIII, Factor V, Exhibition Area (5(2) J. Thromb. Haemost P-T-022 (2007)) Abstract available at: http://www.blackwellpublishing.com/isth2007/abstract.asp?id=66581.

*Primary Examiner* — Lisa J Hobbs
(74) *Attorney, Agent, or Firm* — Morgan, Lewis & Bockius LLP

(57) ABSTRACT

The present invention provides novel methods of increasing the survival of a coagulation protein by inhibiting the interaction with a clearance receptor. The invention also provides methods of preparing compositions that inhibit coagulation protein clearance receptors. Conjugated coagulation proteins, including compositions and formulations thereof, are also provided by the present invention.

15 Claims, 57 Drawing Sheets

Comparison of wt-rFVIII and hydrolyzable PEG-FVIII for their interaction with LRP1. No binding of PEG-FVIII to LRP1 could be detected.

Inhibition of FVIII binding to LRP1 by wt-VWF or PEG-conjugated VWF. Both VWF variants are similar in interfering with the FVIII-LRP1 interaction.

*Fig. 5*

Inhibition of FVIII binding to LRP1 by wt-VWF or PSA-conjugated VWF. PSA-VWF seems to be slightly less efficient than wt-VWF in interfering with the FVIII-LRP1 interaction.

Binding of VWF to recombinant GpIb in the presence of botrocetin. Binding of PEG-VWF to GpIb is reduced by approx. 50%, whereas PSA-VWF virtually lacks the ability to display botrocetin-dependent binding to GpIb.

Binding of VWF to nanobody AU/VWFa-11. Binding of PEG-VWF and PSA-VWF to this nanobody (recognizing the active conformation of VWF) is strongly reduced.

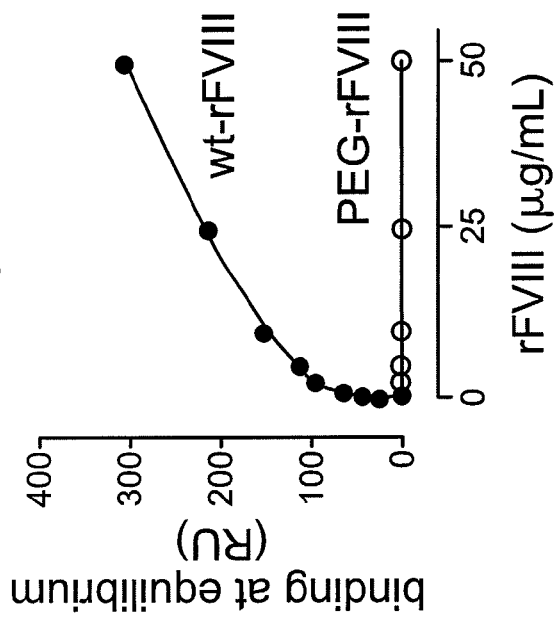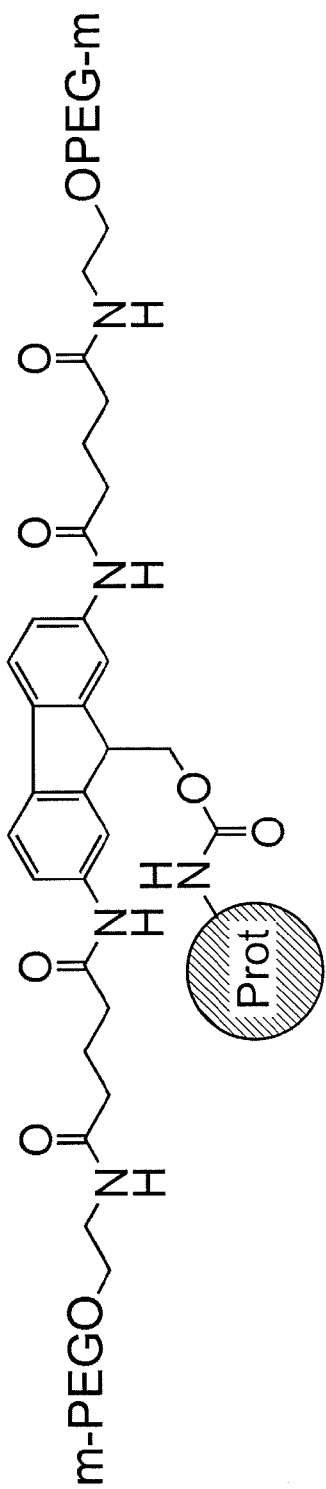
Fig. 13

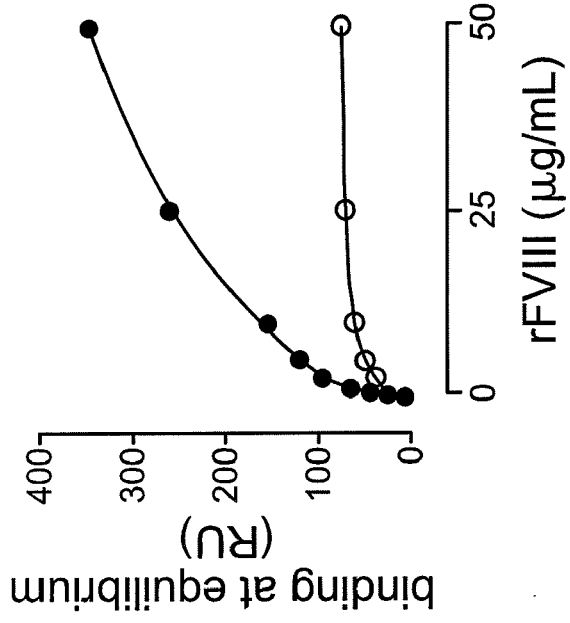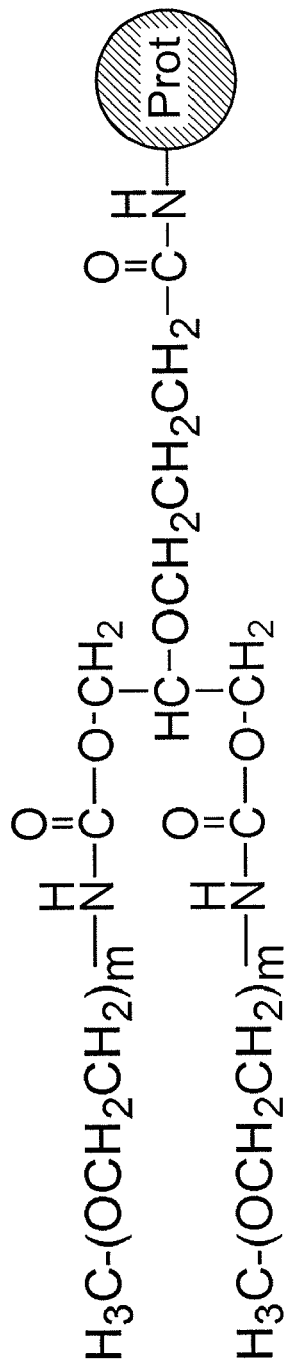
Fig. 15

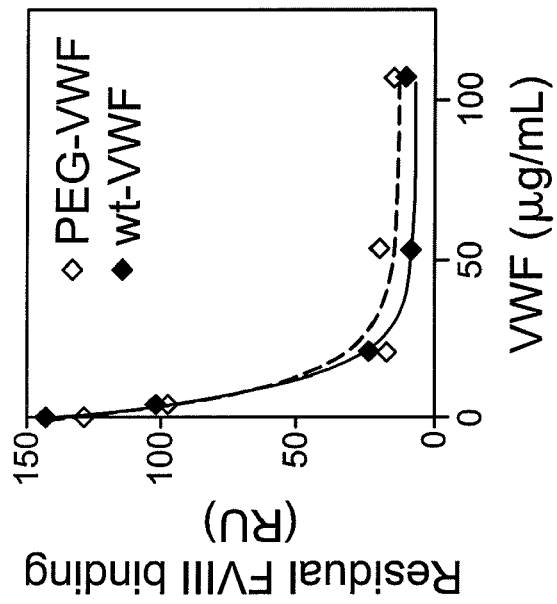
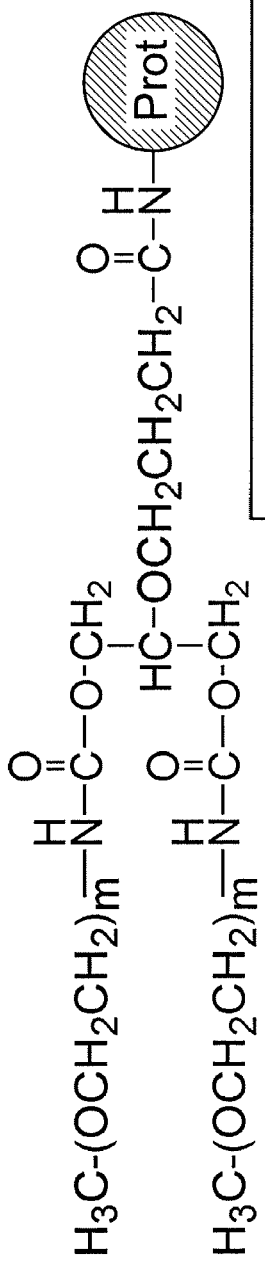
Fig. 17

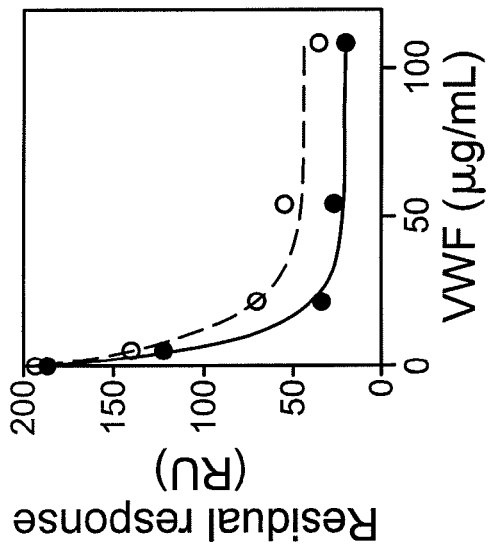
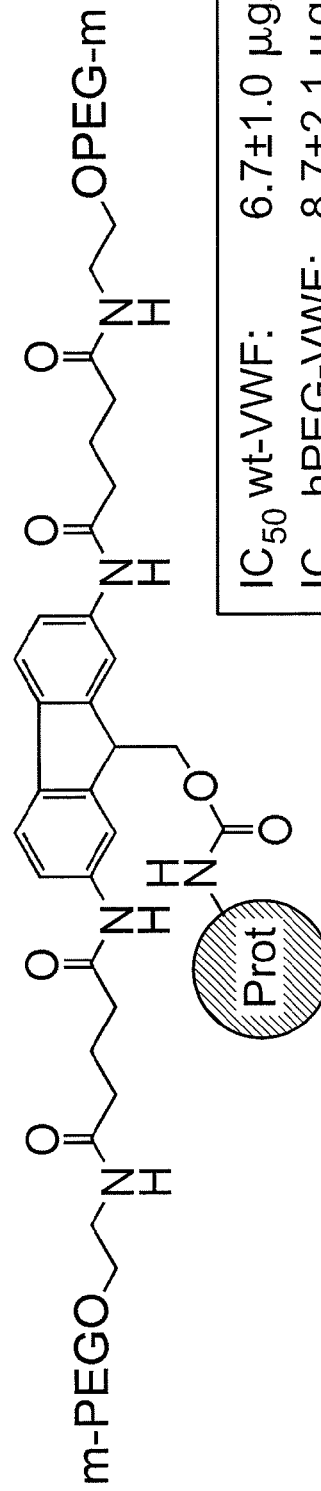
Fig. 18

Fig. 30a
mPEG-Succinimidyl propionate (mPEG-SPA)
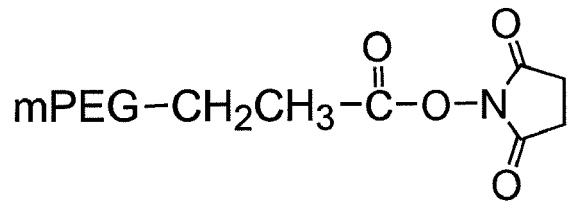
mPEG-Succinimidyl α-methylbutanoate (mPEG-SPA)
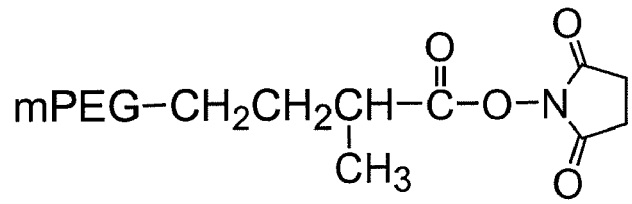
mPEG-CM-HBA-NHS (CM = carboxymethyl;
HBA = Hydroxy butyric acid
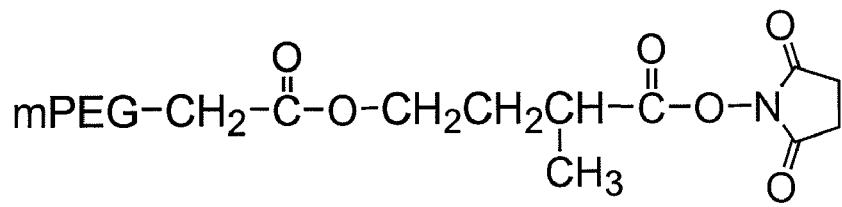
Branched PEG N-Hydroxysuccinimide (mPEG2-NHS)
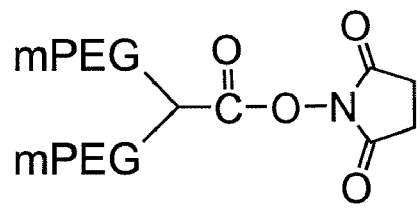

Fig. 30b
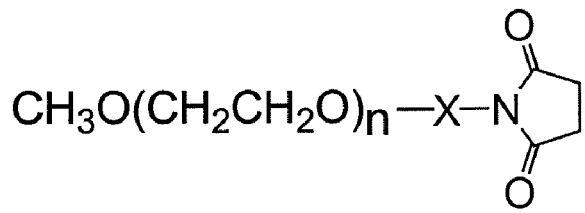
X = carboxymethyl
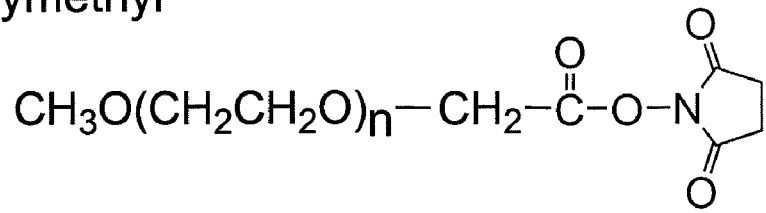
X = carboxypentyl
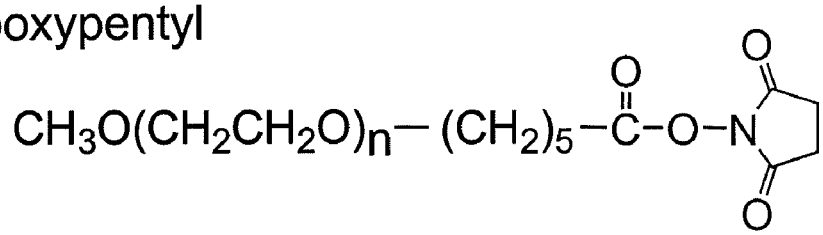
X = succinate
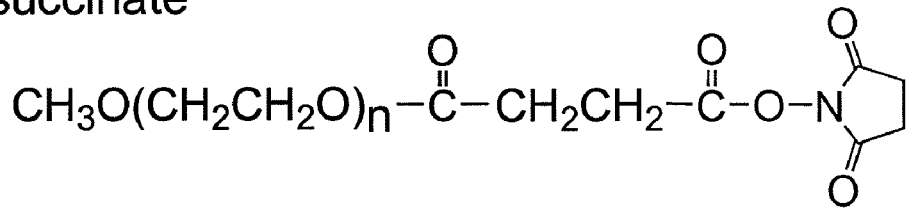
mPEG Succinimidyl succinate
X = glutarate
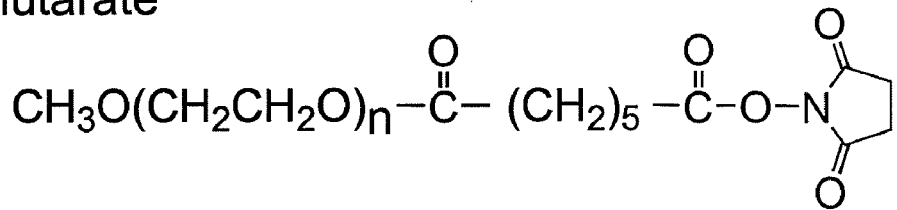
mPEG Succinimidyl glutarate

Fig. 30c
2,3-Bis(methyl)polyoxyethylene-oxy)-1-(1,5-dioxo-5-succinimidyloxy, pentyloxy) propane
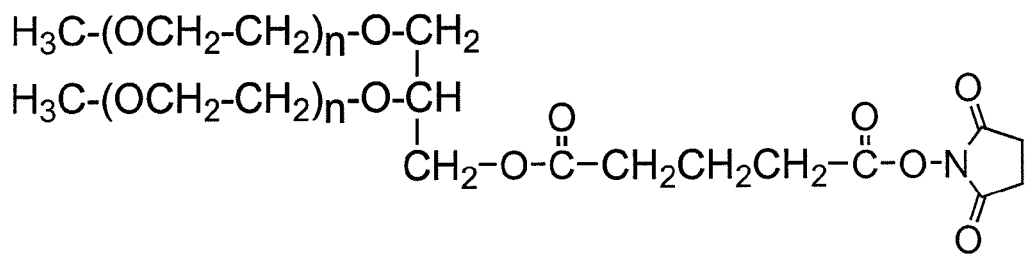
2,3-Bis(methyl)polyoxyethylene-oxy)-1-succinimidyl carboxypentyloxy) propane
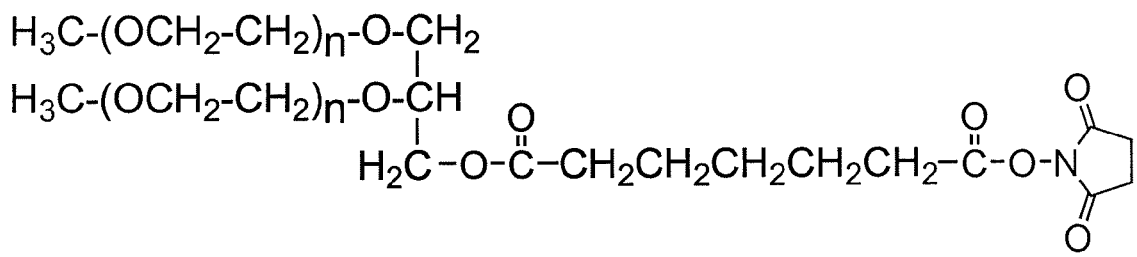
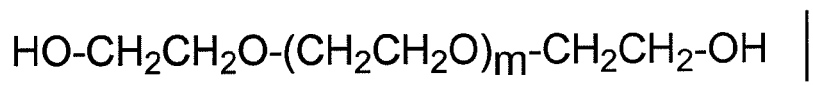
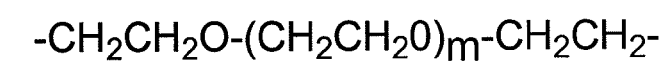
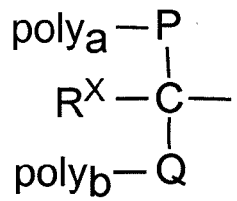   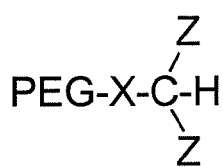

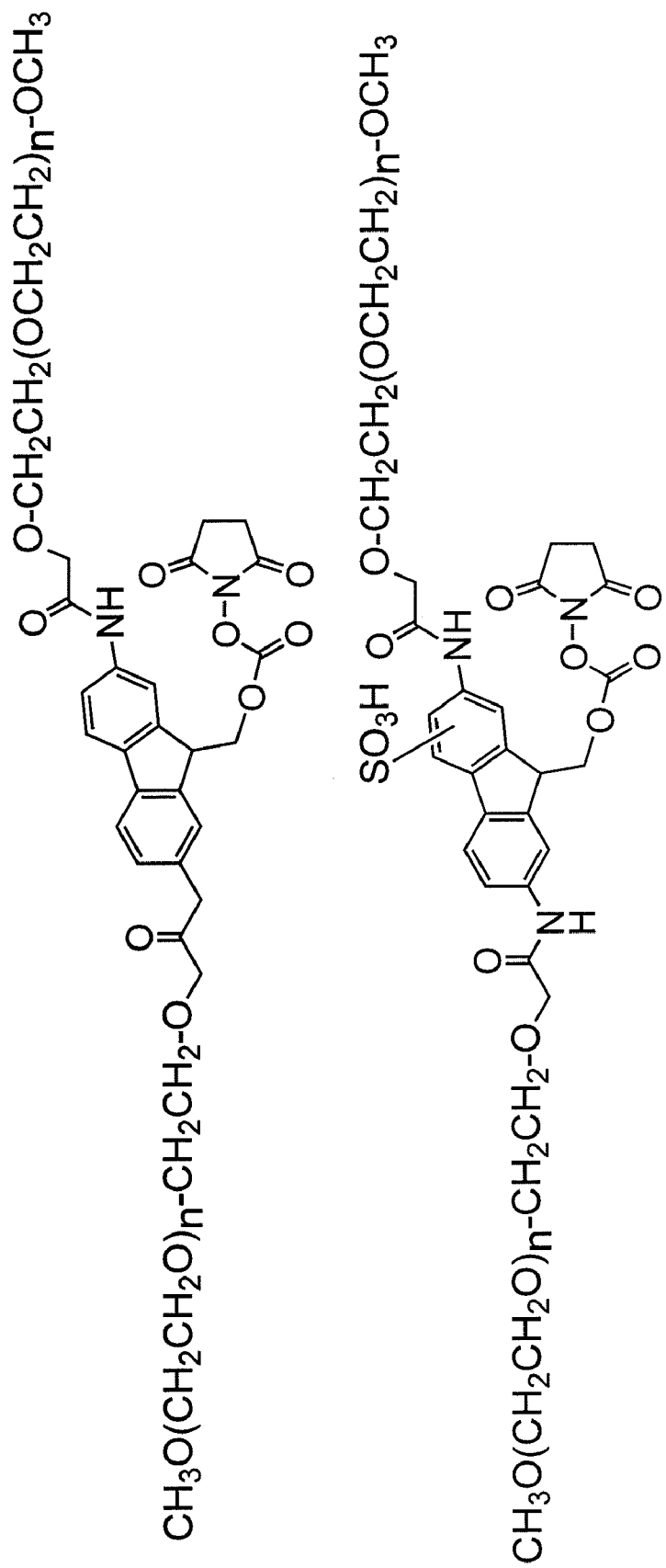
Fig. 30e (Sheet 1)

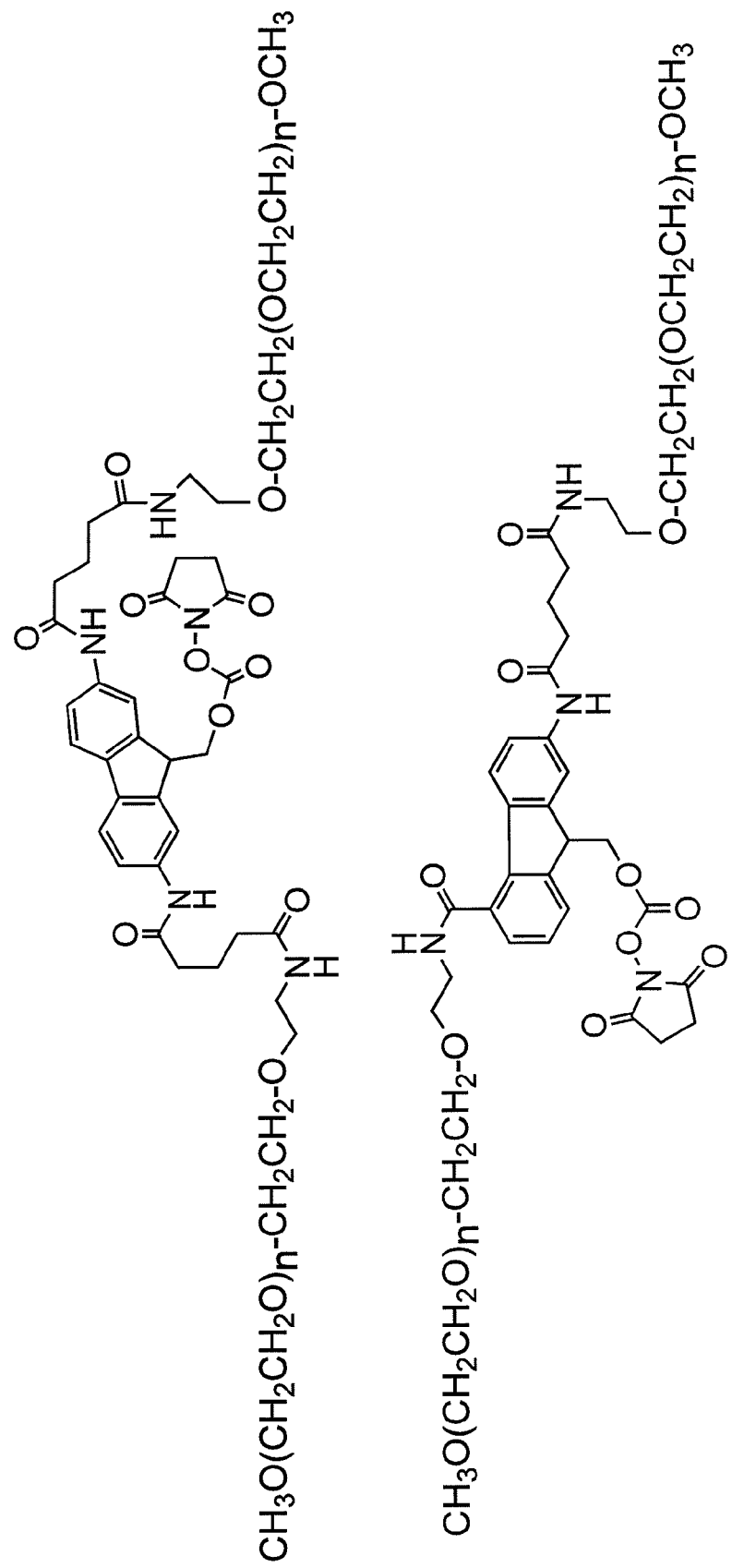
Fig. 30e (Sheet 2)

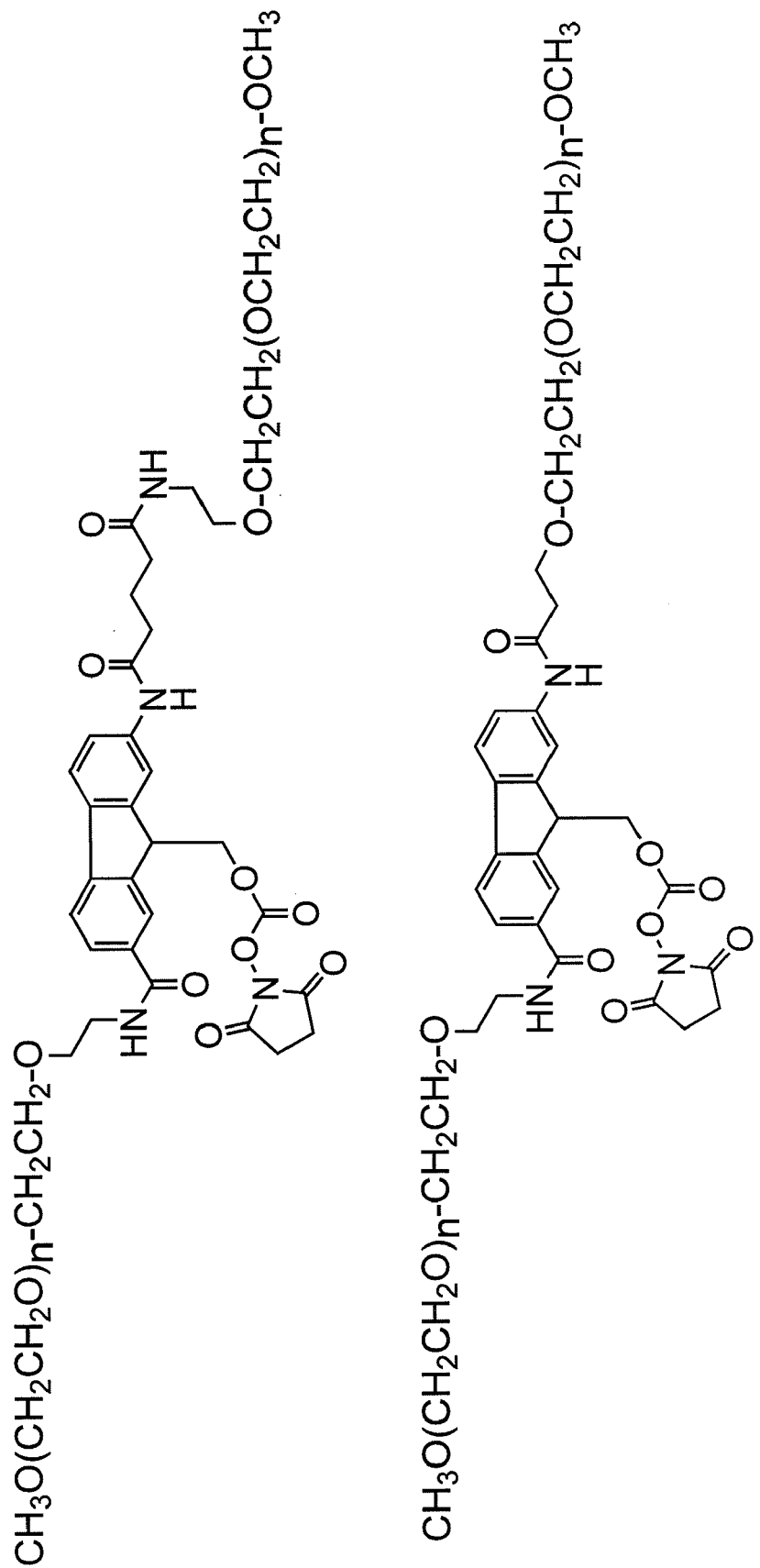
Fig. 30e (Sheet 3)

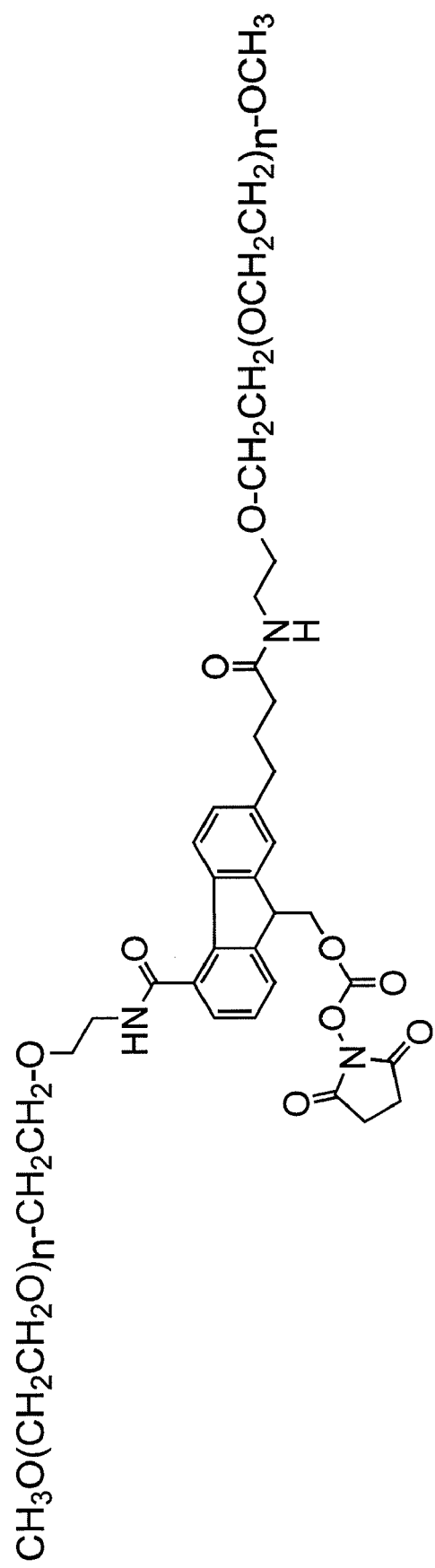
Fig. 30e (Sheet 4)

Fig. 30f (Sheet 1)
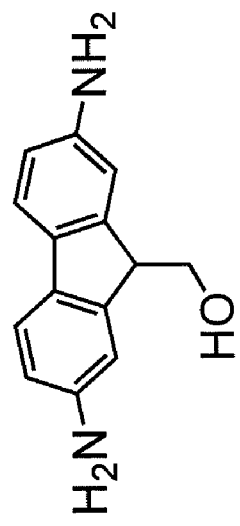
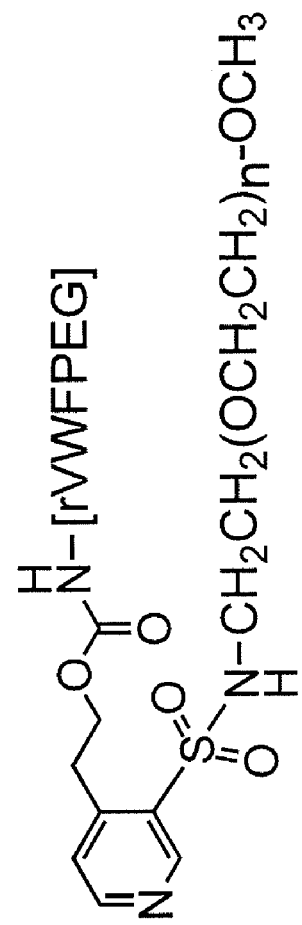

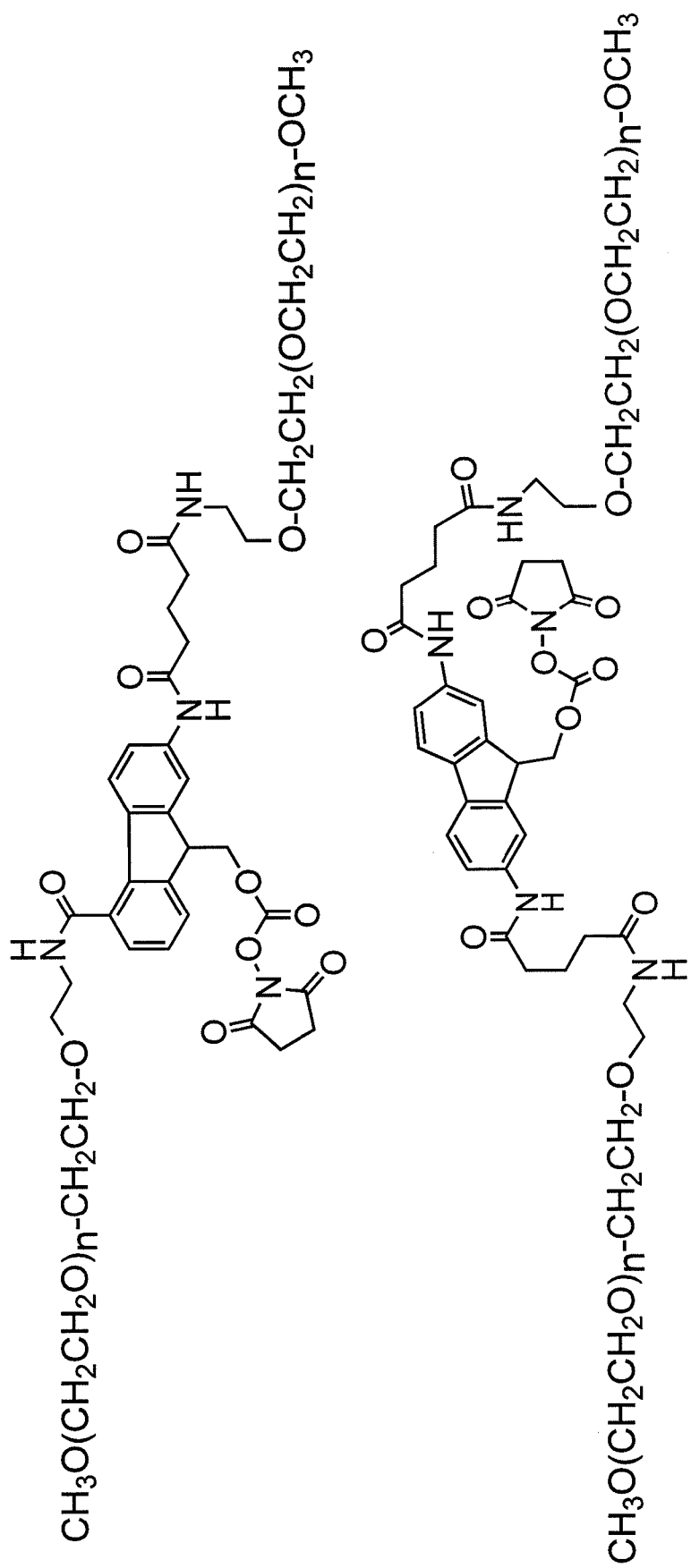
Fig. 30f (Sheet 2)

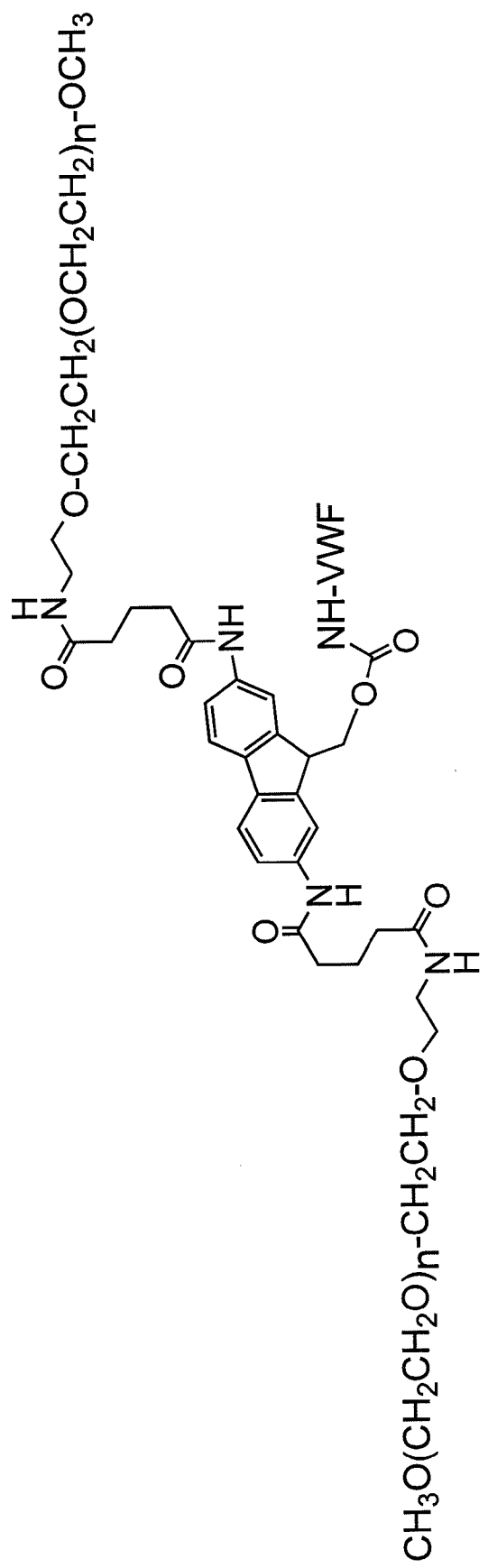
Fig. 30f (Sheet 3)

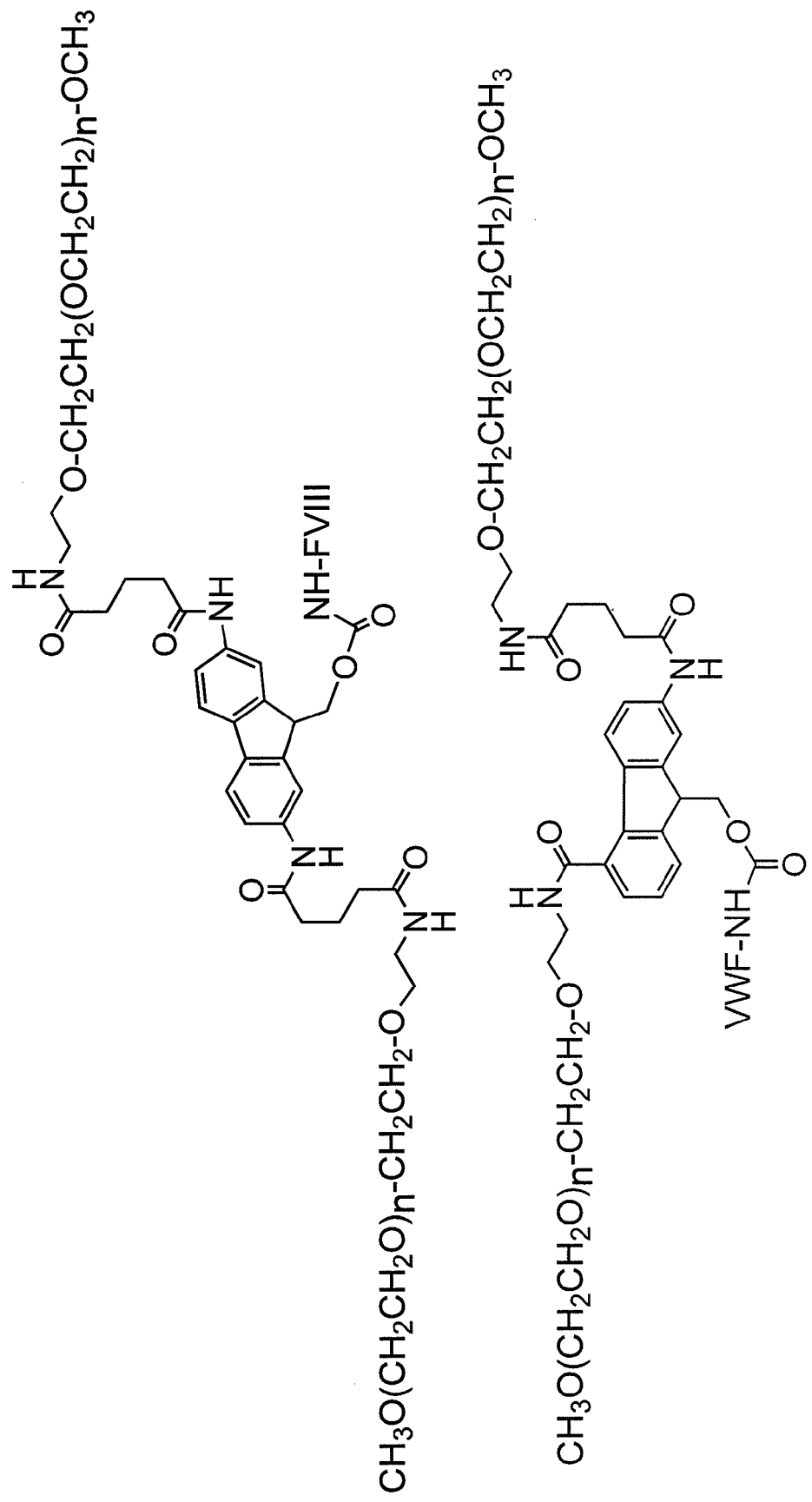
Fig. 30g (Sheet 1)

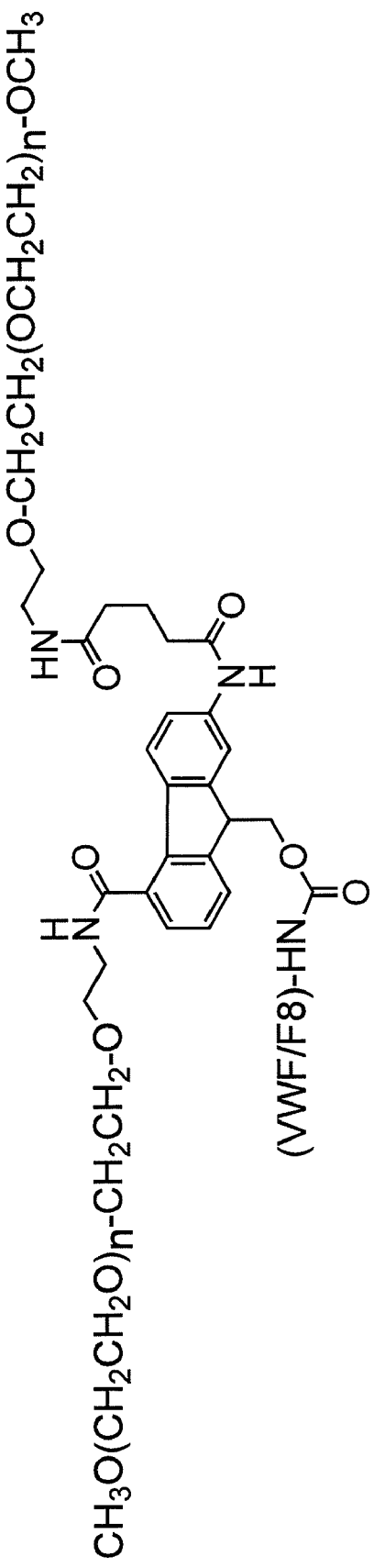
Fig. 30g (Sheet 2)

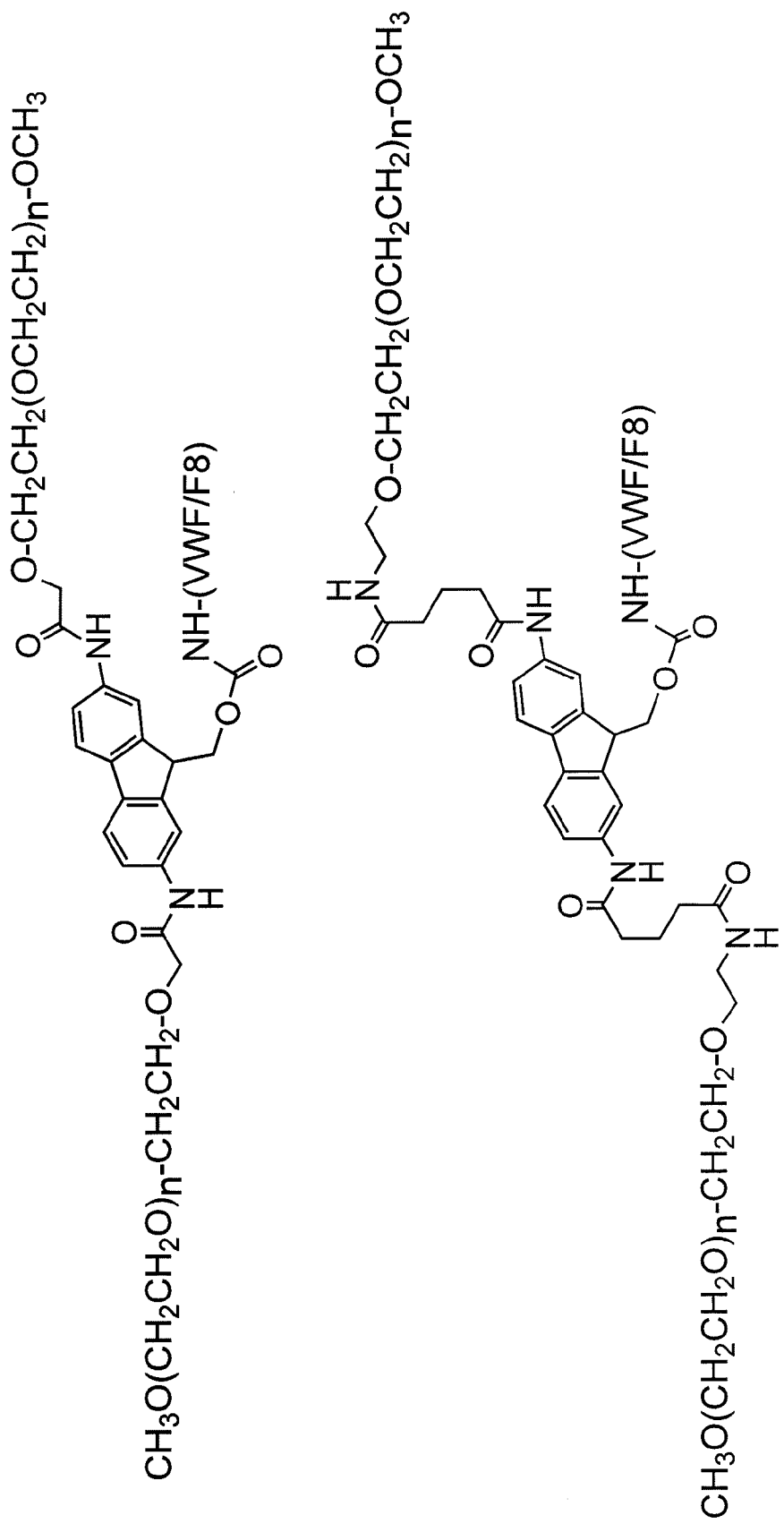
Fig. 30h (Sheet 1)

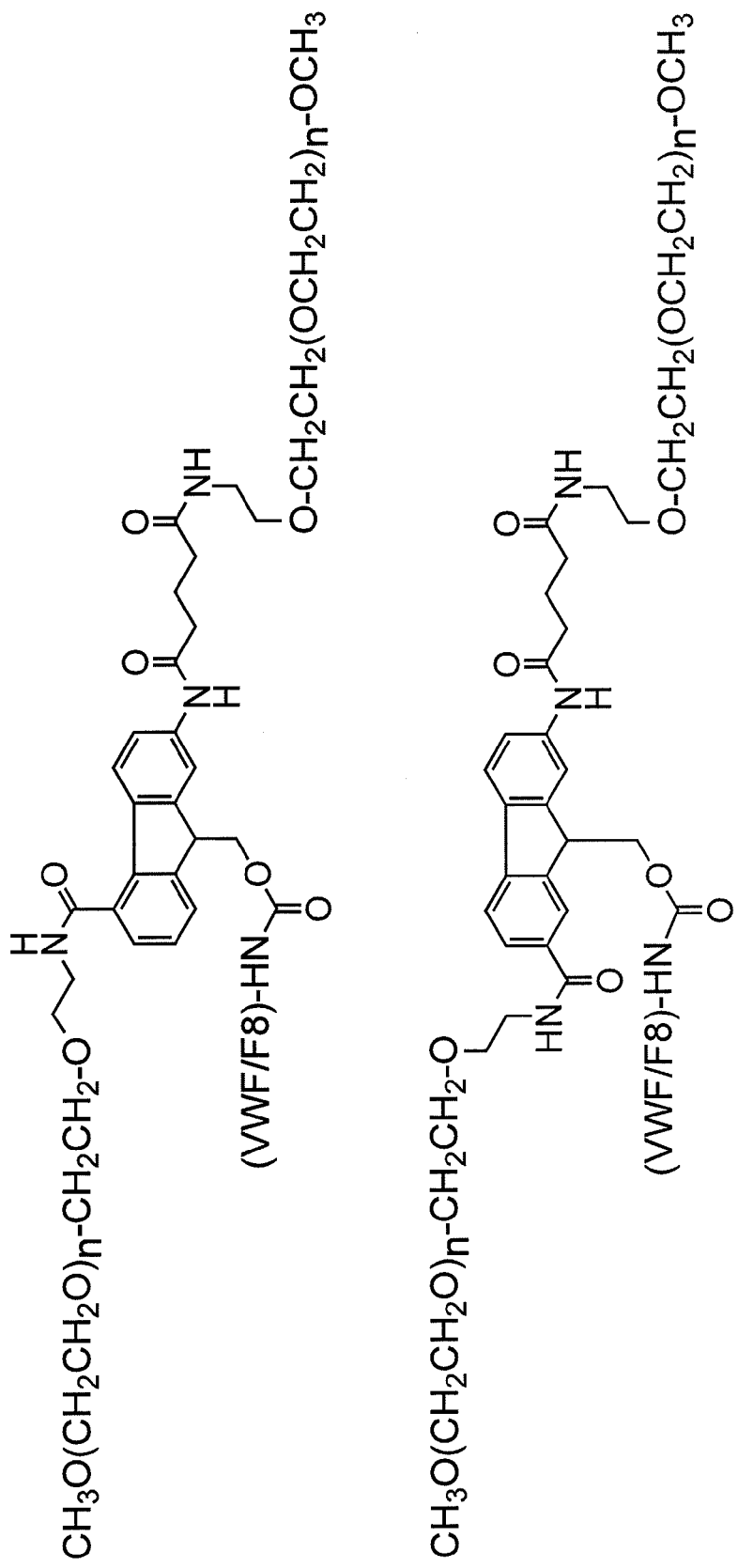
Fig. 30h (Sheet 2)

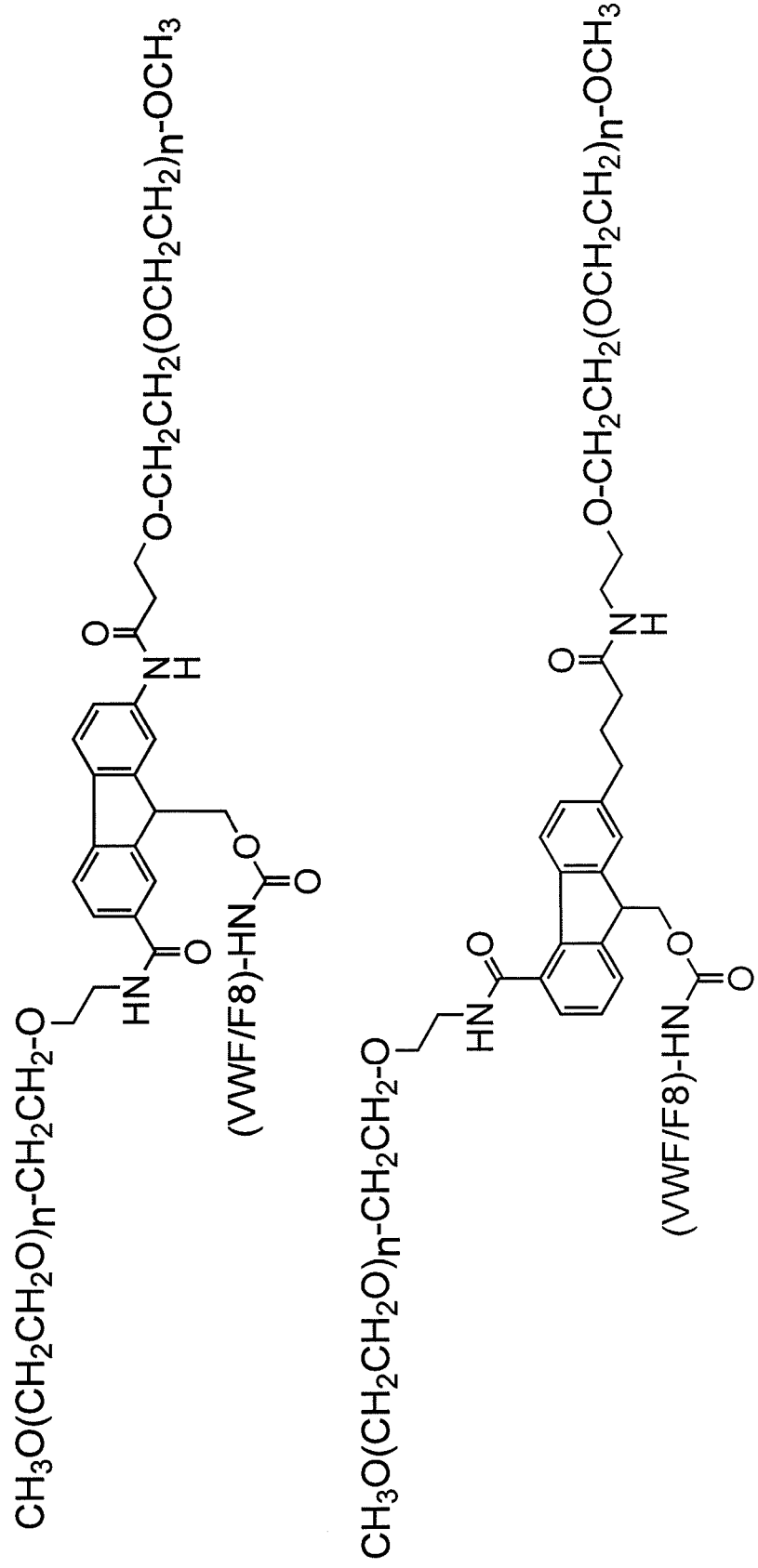
Fig. 30h (Sheet 3)

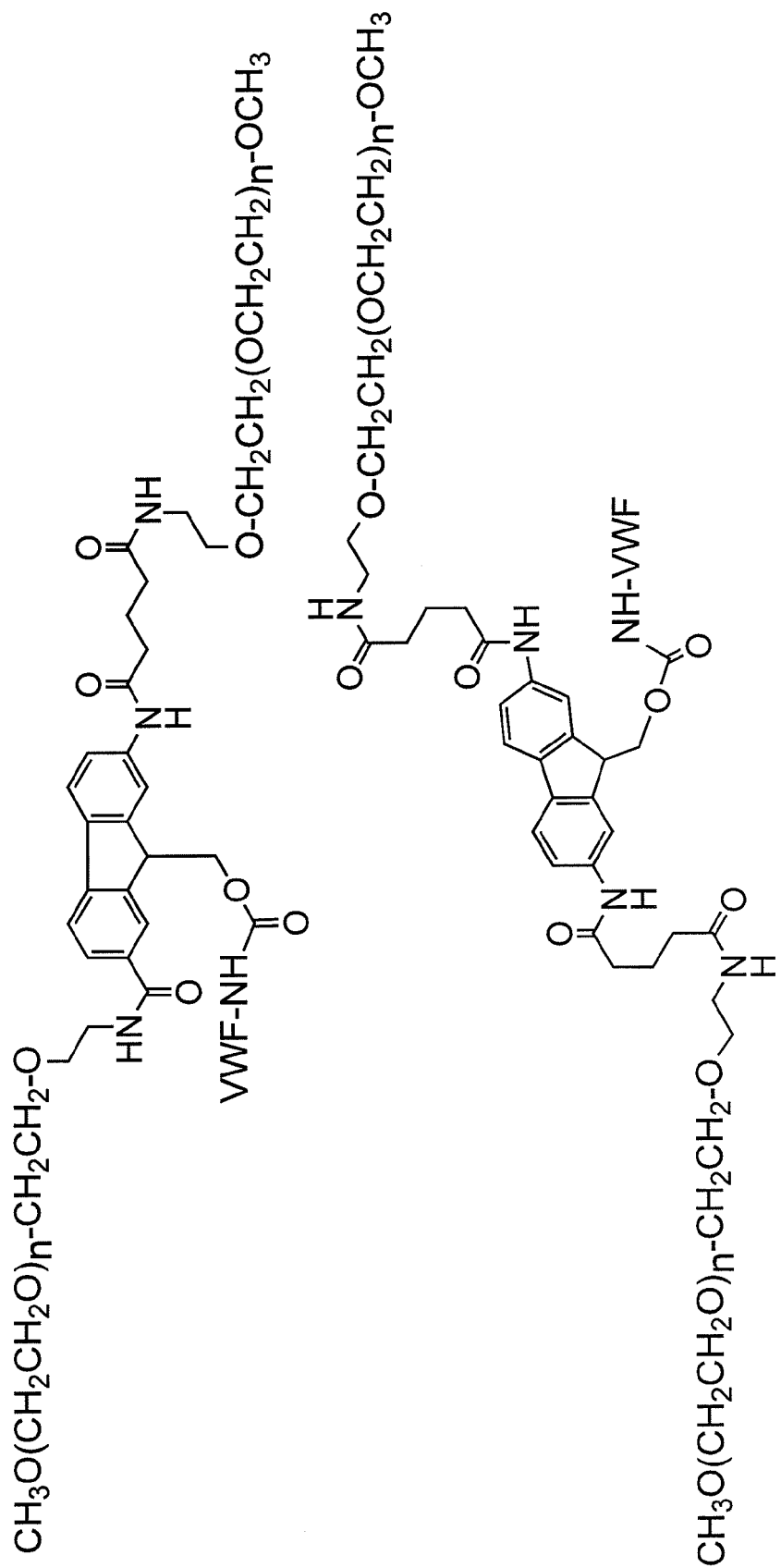
Fig. 30i (Sheet 1)

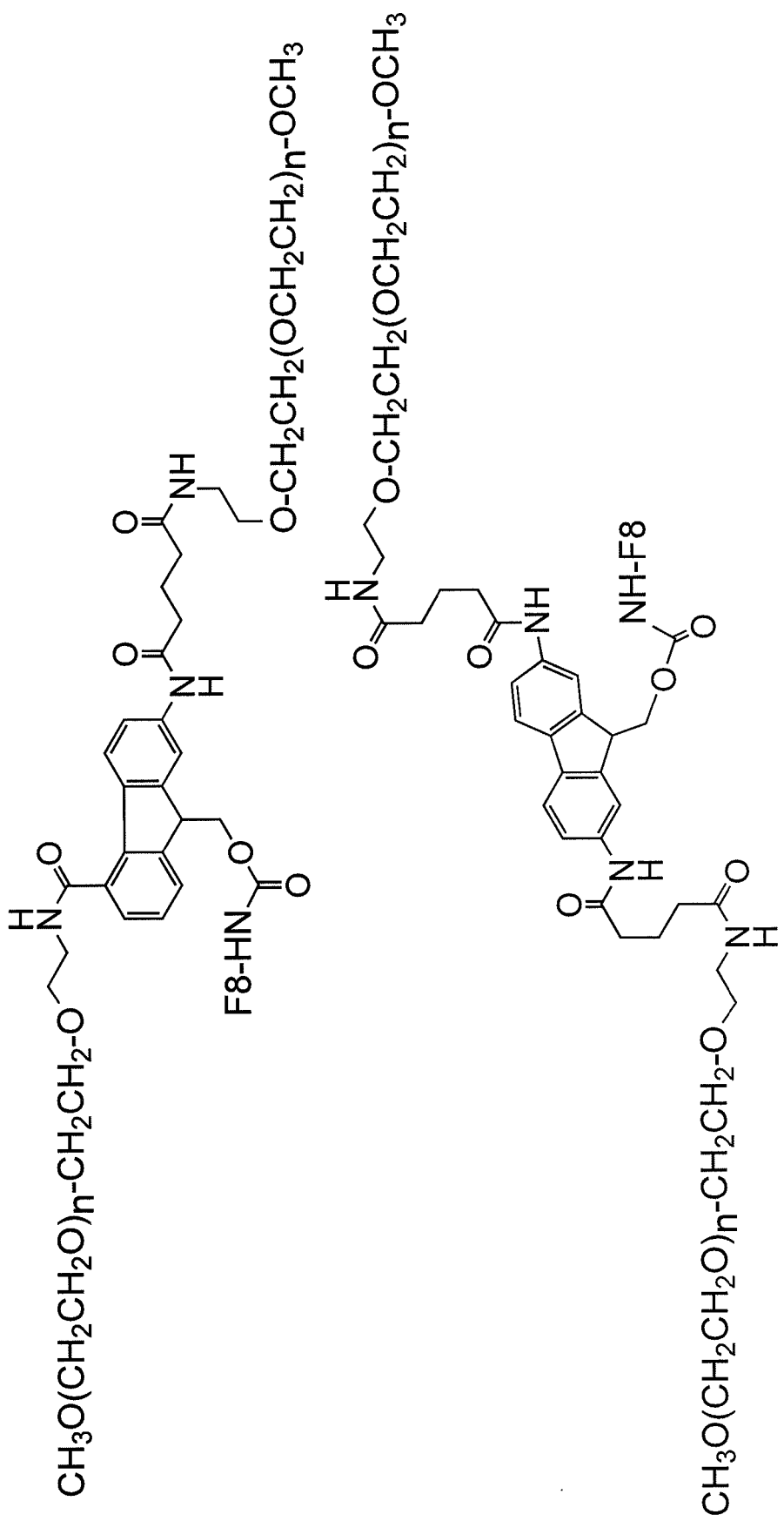
Fig. 30i (Sheet 2)

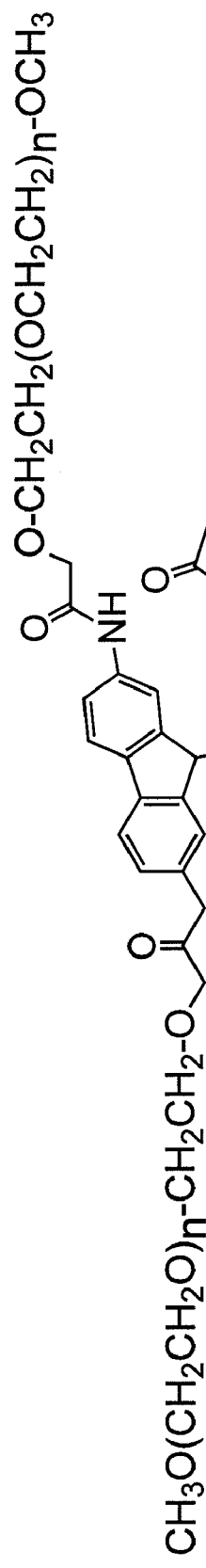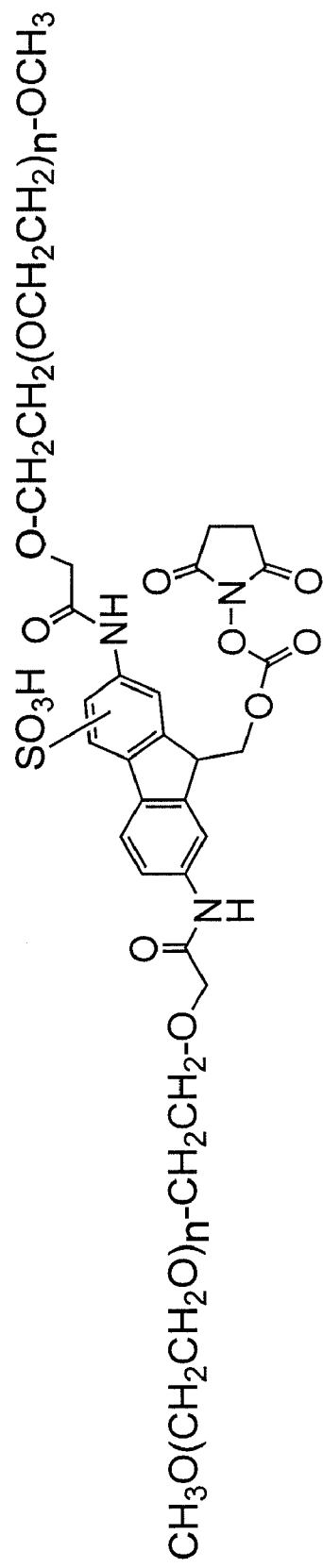
Fig. 30i (Sheet 3)

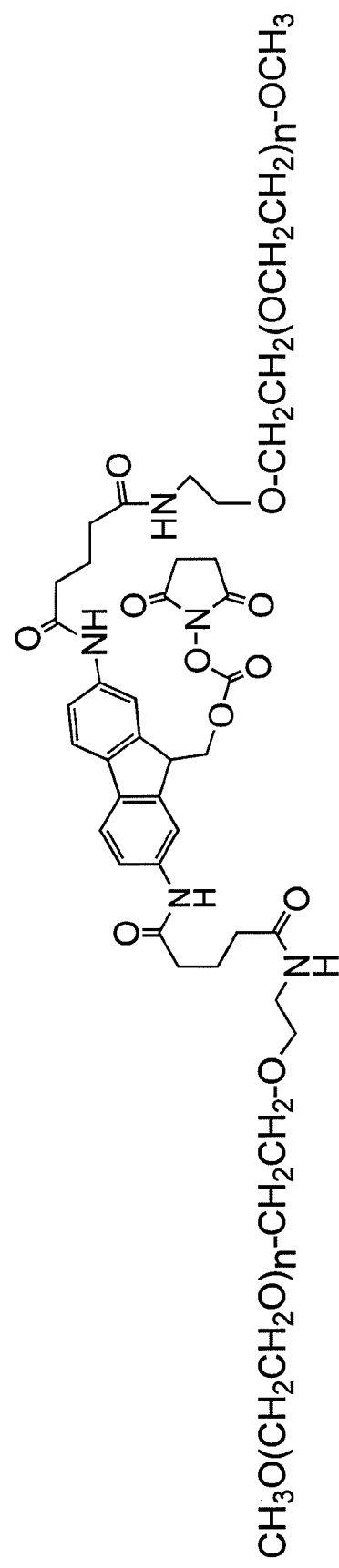
Fig. 30i (Sheet 4)

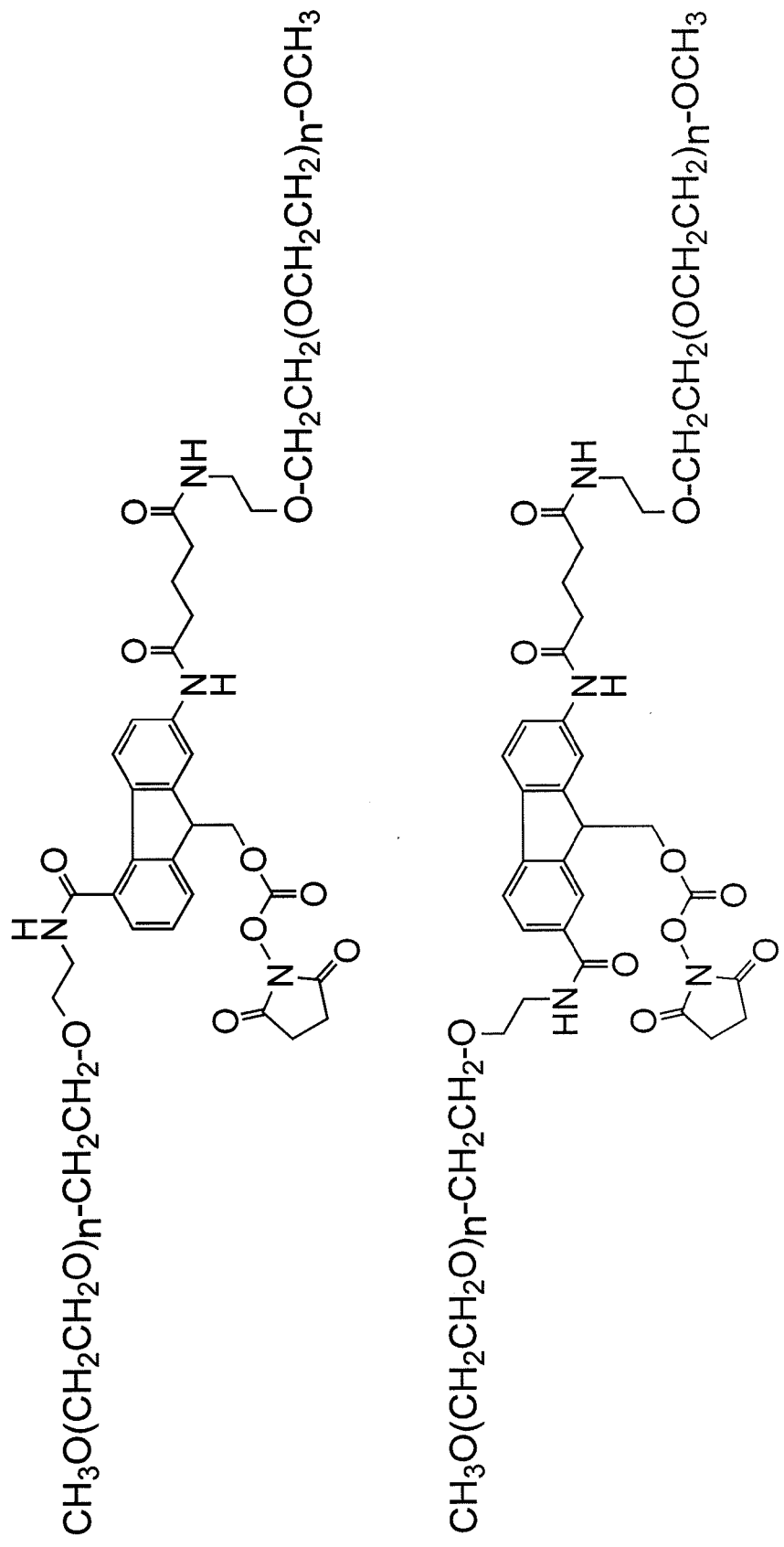
Fig. 30j (Sheet 1)

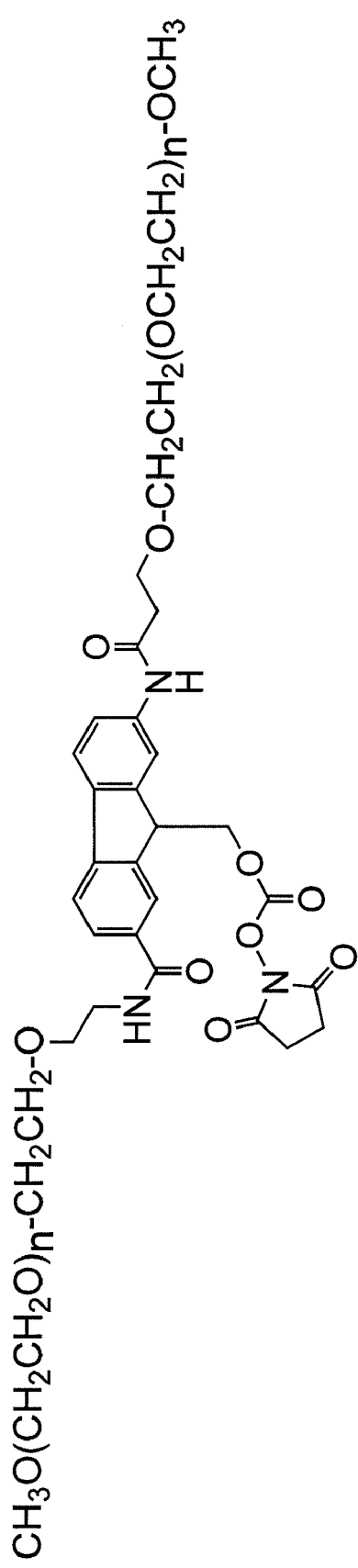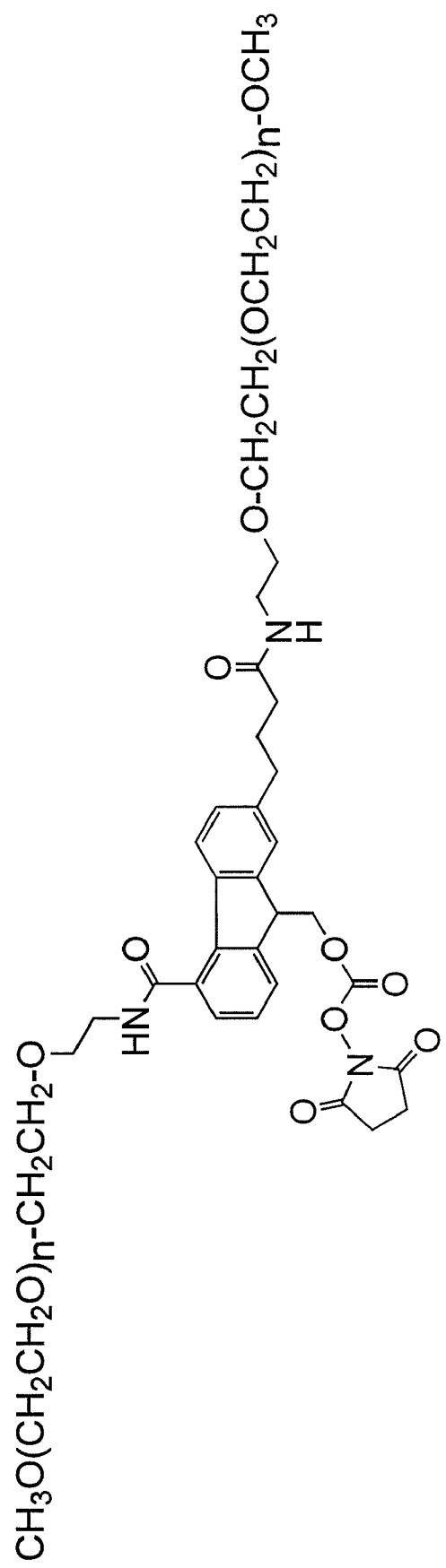
Fig. 30j (Sheet 2)

Fig 30I (Sheet 1)
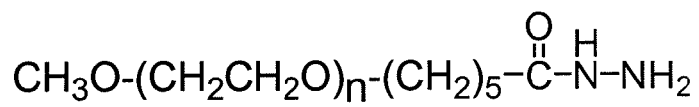
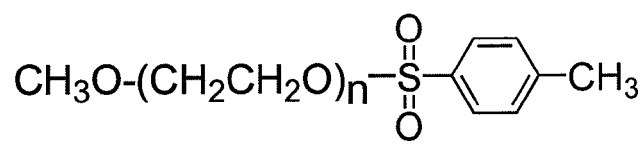
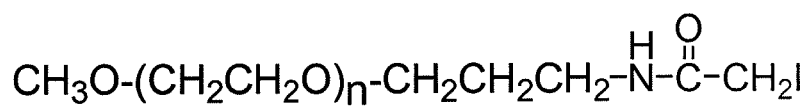
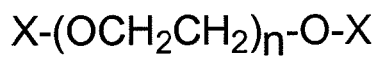
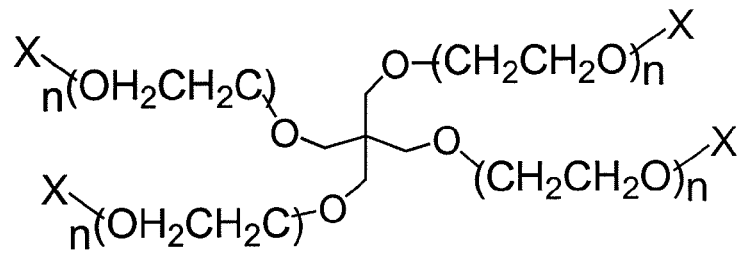
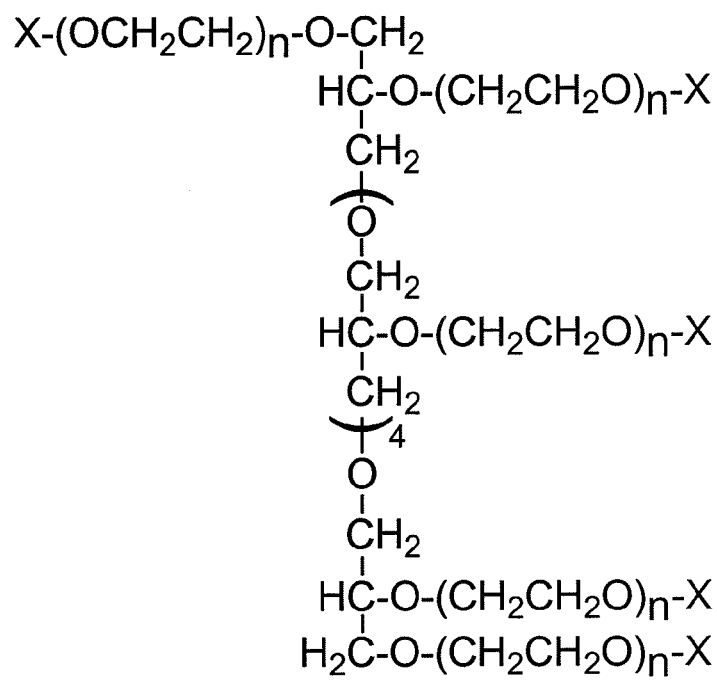

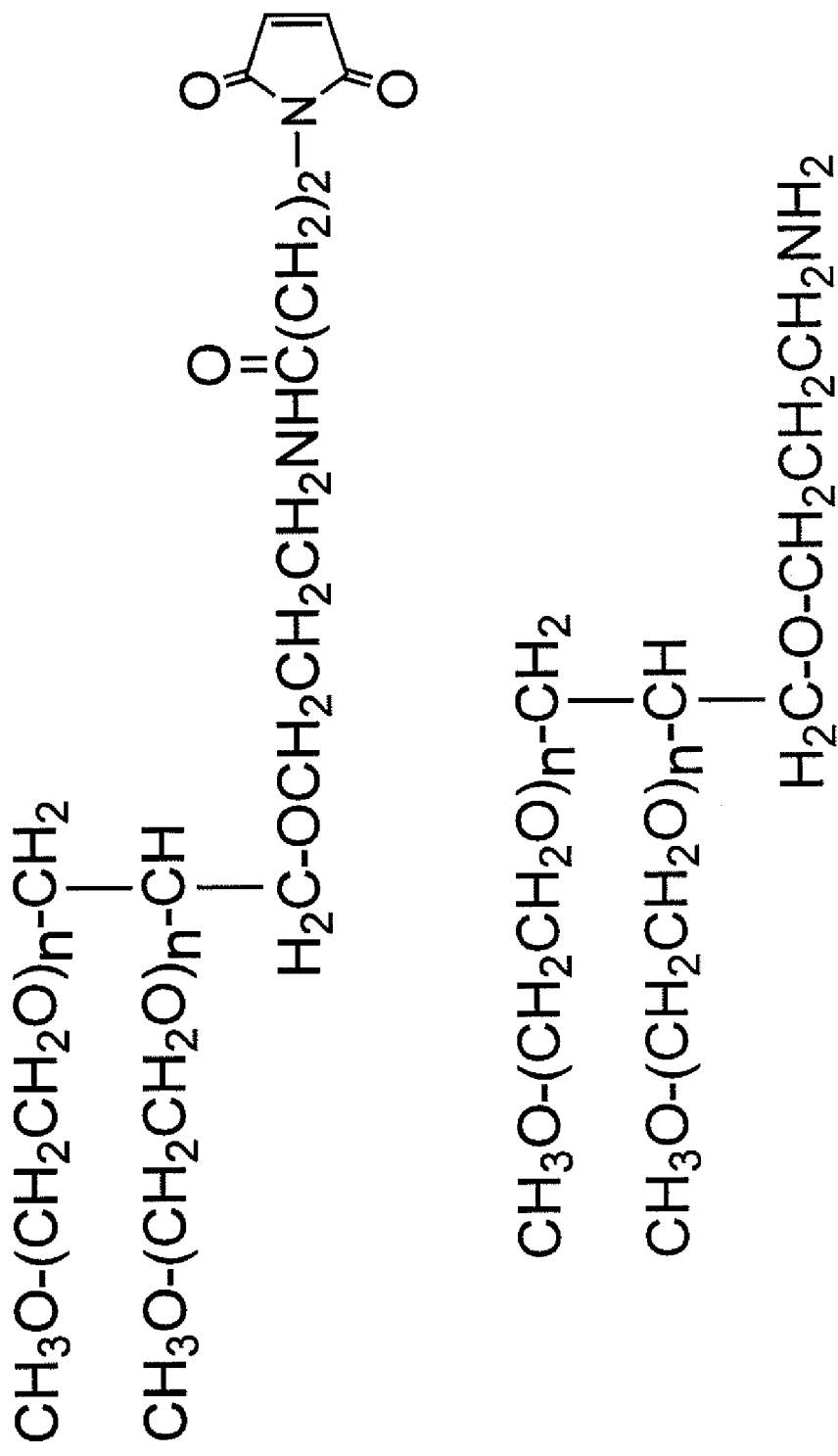
Fig. 30I (Sheet 2)

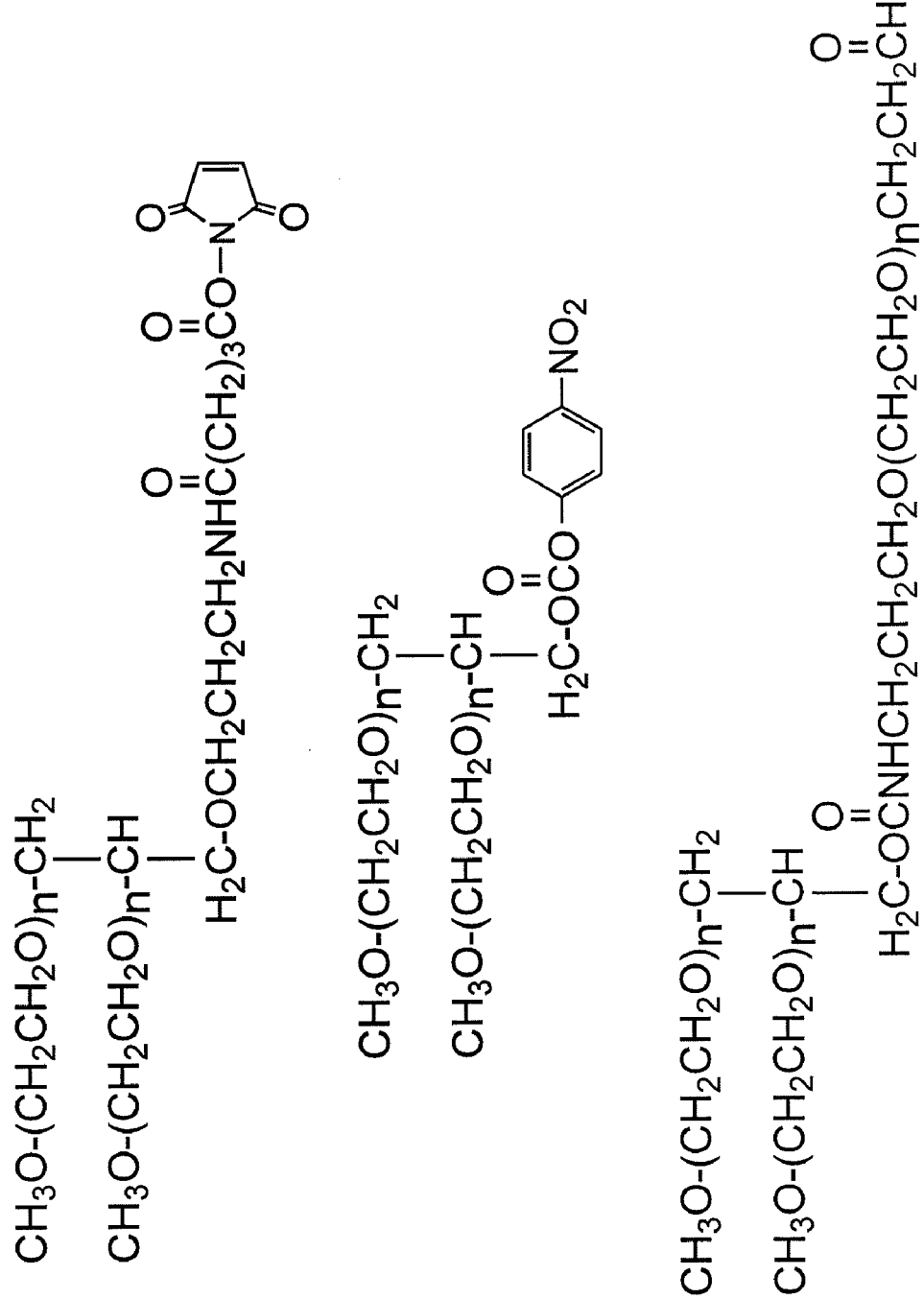
Fig. 30m (Sheet 1)

Fig. 30m (Sheet 2)
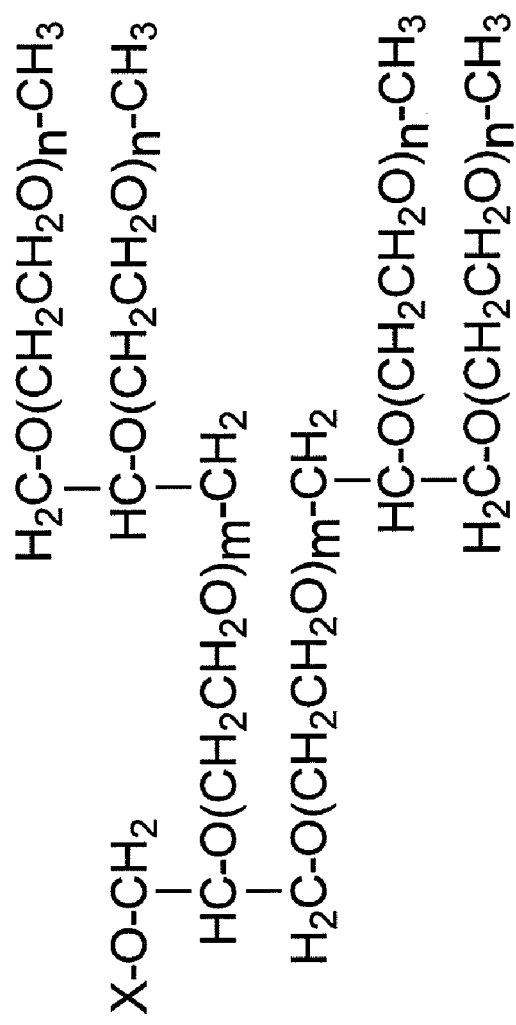

MODIFIED RECOMBINANT FACTOR VIII AND VON WILLEBRAND FACTOR AND METHODS OF USE

CROSS-REFERENCES TO RELATED APPLICATIONS

The present application claims priority to U.S. Ser. No. 60/986,975, filed Nov. 9, 2007, herein incorporated by reference in its entirety.

STATEMENT AS TO RIGHTS TO INVENTIONS MADE UNDER FEDERALLY SPONSORED RESEARCH OR DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

Hemostasis involves the interaction of various hemostatic reaction routes finally leading to thrombus formation. Thrombi are deposits of blood components on the surface of the vascular wall that mainly consist of aggregated blood platelets and insoluble cross-linked fibrin. Fibrin formation is the result of the restricted proteolysis of fibrinogen by thrombin, a coagulation enzyme. Thrombin is the end product of the coagulation cascade, a succession of zymogen activations occurring on the surfaces of activated blood platelets and leucocytes, and a variety of vascular cells (for a survey, cf. K. G. Mann et al., Blood, 1990, Vol. 76, pp. 1-16).

A key function in the coagulation cascade resides in the activation of Factor X by the complex of activated Factor IX (Factor IXa) and activated Factor VIII (Factor VIIIa). A deficiency or a dysfunction of the components of this complex is associated with the blood disease known as hemophilia (J. E. Sadler & E. W. Davie: Hemophilia A, Hemophilia B, and von Willebrand's Disease, in G. Stamatoyannopoulos et al., (Eds.): The molecular basis of blood diseases. W.B. Saunders Co., Philadelphia, 1987, pp. 576-602). Hemophilia A is related to a deficiency of Factor VIII activity, whereas Hemophilia B is related to a Factor IX deficiency. Current treatment consists of a replacement therapy using pharmaceutical preparations comprised of the normal coagulation factor. Of these thrombopathies, Hemophilia A occurs more frequently, affecting approximately one out of 10,000 men. Replacement therapy in Hemophilia A patients involves the repeated administration of preparations containing normal Factor VIII by intravenous infusion. The interval between the infusions is a function of the degradation of the Factor VIII activity in blood circulation. The half-life of the Factor VIII activity after an infusion differs from one individual to another, ranging from 10 to 30 hours. Thus, a prophylactic therapy requires an infusion every two to three days. This constitutes a heavy load on the life of hemophilic patients, in particular, if the venous access has become difficult due to local citratization following frequent needle punctures for intravenous infusions.

It would be particularly advantageous if the frequency of infusions could be lowered by using Factor VIII having extended half-lives. The half-life of Factor VIII may be extended by interfering with the mechanism of Factor VIII degradation (clearance), for instance, by reducing the affinity of Factor VIII to receptors that are essential to its clearance, either directly by modifying Factor VIII on its binding site(s) for the clearance receptors concerned, or indirectly by using compounds interfering with the interaction of Factor VIII with those receptors. However, the design of such agents has so far been impeded by not knowing the Factor VIII clearance mechanism, the cell receptors involved in this process, and the molecular sites involved in the Factor VIII receptor interaction.

There is limited knowledge in the molecular field as to the clearance mechanism of Factor VIII. The Factor VIII protein is synthesized as a single chain polypeptide comprising 2332 amino acids and having the typical domain structure A1-A2-B-A3-C1-C2 (G. A. Vehar et al., Nature, Vol. 312, 1984, pp 337-342; J. J. Toole et al., Nature, Vol., 312, 1984, 342-347). Factor VIII enters the blood circulation as a heterodimeric complex of heavy and light chains as a result of intracellular endoproteolytic processing. The light chain comprises the amino acid residues 1649-2332 and contains the A3-C1-C2 domains. The heavy chain contains the domains A1-A2-B (residues 1-1648) and is heterogenic due to the limited proteolysis in a number of positions within the B domain. The Factor VIII heterodimer has no biological activity, but the heterodimer becomes active as a cofactor of the enzyme Factor IXa after proteolytic activation by thrombin or Factor Xa. Proteolysis affects both the heavy chain and the light chain of Factor VIII (M. J. S. H. Donath et al., J. Biol. Chem., Vol. 270, 1995, pp. 3648-3655), leading to the cleavage of an aminoterminal fragment from the light chain and a break of domain connection sites within the heavy chain (between domains A1-A2 and A2-B). The activated cofactor, Factor VIIIa, is a heterotrimer comprised of the A1 domain, the A2 domain and the light chain including domains A3-C1-C2.

It is well known in the art that the half-life of the non-activated Factor VIII heterodimer strongly depends on the presence of von Willebrand Factor, which exhibits a strong affinity to Factor VIII (yet not to Factor VIIIa) and serves as a carrier protein (J. E. Sadler and E. W. Davie: Hemophilia A, Hemophilia B and von Willebrand's disease, in G. Stamatoynnopoulos et al. (Eds.): The molecular basis of blood diseases. W.B. Saunders Co., Philadelphia, 1987, pp. 576-602). It is known that patients suffering from von Willebrand's disease type 3, who do not have a detectable von Willebrand Factor in their blood circulation, also suffer from a secondary Factor VIII deficiency. In addition, the half-life of intravenously administered Factor VIII in those patients is 2 to 4 hours, which is considerably shorter than the 10 to 30 hours observed in Hemophilia A patients.

From these findings results that Factor VIII tends to a rapid clearance from the blood circulation and that this process is to some extent inhibited by complexation with its natural carrier, von Willebrand Factor. Nevertheless, its half-life remains undesirably short.

Recently, it has been indicated in a preliminary report that Factor VIII activated by thrombin binds to low density lipoprotein receptor protein ("LRP") (A. Yakhyaev et al., Blood, Vol. 90 (Suppl. 1), 1997, 126-I (Abstract). This abstract describes the cell absorption and the degradation of Factor VIII fragments activated by thrombin and reports that the A2 domain, unlike the two other subunits of the Factor VIIIa heterotrimer, interacts with cell-bound LRP. The authors have suggested that binding of the A2 domain to LRP further destabilizes the loose interaction of the A2 domain in the Factor VIIIa heterotrimer and thereby downwardly regulating Factor VIIIa activity.

It is known that LRP is one of the receptors that are involved in the clearance of various proteins. LRP in this field is also known as the alpha2-macroglobulin receptor, belonging to the family of low density lipoprotein (LDL) receptors. It is comprised of two non-covalently connected polypeptide chains: an alpha chain (515 kd) and a .beta.-chain (85 kd) [for a review refer to D. K. Strickland et al., FASEB J Vol. 9, 1995, pp. 890-898]. LRP is a multi-ligand receptor for lipoprotein and proteinase catabolism. The β-chain includes a transmembrane domain and a short cytoplasmatic tail which is essential to endocytosis. The alpha chain functions as a large ectodomain and includes three types of repeats: epidermal growth factor-like domains, Tyr-Trp-Thr-Asp (SEQ ID NO:1) sequences and LDL receptor class A domains. These class A domains are present in four separate clusters, clusters I (2 domains), II (8 domains), III (20 domains) and IV (11 domains). It has been shown that these clusters are involved in ligand binding. LRP is expressed in a plurality of tissues such as the placenta, lungs, brain, and liver. In the liver, LRP is present on parenchyma cells and Kupffer cells. Moreover, LRP is expressed in a plurality of cell types such as fibroblasts, smooth muscle cells, Leydig cells, Sertoli cells, and monocytes. The differentiation from monocytes to macrophages is associated with a drastic increase in LRP expression. Finally, LRP is expressed also in cell types such as ape kidney cells (COS) or Chinese hamster ovary cells (CHO) (D. J. FitzGerald et al., J. Cell Biol. Vol. 129, 1995, pp. 1533-1541), which are both frequently used to express mammalian proteins including Factor VIII (R. J. Kaufman et al., Blood Coag. Fibrinol. Vol. 8 (Suppl. 2), 1997, pp. 3-14).

LRP is involved in the clearance of a diversity of ligands including proteases, inhibitors of the Kunitz type, protease serpin complexes, lipases and lipoproteins, which suggests that LRP plays an essential role in various physiological arid pathophysiological clearance processes (Narita et al., Blood, Vol. 2, pp. 555-560, 1998; Orth et al., Proc. Natl. Acad. Sci., Vol. 89, pp. 7422-7426, 1992; Kounnas et al., J. Biol. Chem., Vol. 271, pp. 6523-6529, 1996). LRP's physiological importance goes back to the finding that LRP knock-out mice do not survive the embryonic stage (Herz, J. Curr. Opin. Lipidol Vol. 4, 1993, pp. 107-113). LRP secretion may be complicated by LRP interacting with multiple ligands. Within the cell, LRP is, however, associated with its chaperone protein, the receptor-associated protein (RAP). If bound to RAP, LRP cannot interact with any of its known ligands (Herz et al., J. Biol. Chem., Vol. 266, pp. 21232-21238, 1991).

The interaction of LRP with its natural ligands may be effectively blocked by soluble LRP fragments. These fragments may be obtained by various methods known in the art, including recombinant techniques, and as such provide access to effective LRP antagonists (I. R. Horn, J. Biol. Chem., Vol. 272, 1997, pp. 13608-13613; B. Vash et al., Blood, Vol. 92, 1998, pp. 3277-3285).

In view of the typical role of LRP in the clearance of proteases, inhibitors and protease inhibitor complexes, it is to be noted that LRP also binds the activated non-enzymatic cofactor Factor VIIIa (A. Yakhyaev et al., Blood Vol. 90 (Suppl. 1), 1997, 126-I (Abstract)). While that disclosure suggests LRP's role in the regulation of Factor VIIIa, it does not give any hint as to its role in the regulation of non-activated heterodimeric Factor VIII, although this would be of potential interest for the clearance of Factor VIII from the blood circulation, and hence the half-life of Factor VIII.

Accordingly, it was further shown in Lentig et al. (JBC 274(34):23734-9 (1999)) and U.S. Pat. No. 6,919,311, that the light chain, but not the heavy chain, of Factor VIII bound to surface exposed LRP1 receptor protein. Further experimentation led to the identification of several exosites in both the C2 and A3-C1 regions of the light chain, that are responsible for the LRP1 binding activity. This led to the discovery that specific mutations in this region weaken the interaction between the proteins.

Von Willebrand factor (vWF) is a glycoprotein circulating in plasma as a series of multimers ranging in size from about 500 to 20,000 kD. Multimeric forms of vWF are composed of 250 kD polypeptide subunits linked together by disulfide bonds. vWF mediates the initial platelet adhesion to the subendothelium of the damaged vessel wall, only the larger multimers also exhibiting hemostatic activity. Multimerized VWF binds to the platelet surface glycoprotein Gplbα, through an interaction in the A1 domain of VWF, in order to facilitate platelet adhesion. It is assumed that endothelial cells secret large polymeric forms of vWF and that those forms of vWF which have a low molecular weight (low molecular weight vWF) have arisen from proteolytic cleavage. The multimers having large molecular masses are stored in the Weibel-Pallade bodies of the endothelial cells and liberated upon stimulation. The full length of cDNA of vWF was cloned; the propolypeptide corresponds to amino acid residues 23 to 764 of the full length prepro-vWF (Eikenboom et al (1995) Haemophilia 1, 77 90).

Moreover, monomeric vWF functions as a molecular carrier of Factor VIII (FVIII) in plasma, stabilizing the coagulation factor. Reduction of FVIII binding activity, due to either reduced vWF protein levels or lowered FVIII binding affinity, results in one of three types of von Willebrand's Disease. In addition to, or alternatively, certain types of von Wildebrand's disease are characterized by an increase or decrease in the level of Gplbα-mediated platelet association, namely in Types 2A, 2B, and 2M (summarized in Castaman et al., Disorders of Hemostasis 88(1):94-108 (2003)). As such, the modulation of vWF interactions with both FVIII and Gplbα is a viable strategy for the treatment of both Haemophlia and von Willebrand's Disease.

There have been several prior art attempts to enhance the pharmacokinetic profile of Factor VIII, including modifications in various regions of Factor VIII polypeptides:

WO 87/07144 describes various modifications of proteolytic interfaces comprising arginine and lysine residues, reducing the instability of the molecules for a specific protease-catalyzed cleavage, for instance the Factor VIIIa interface between Arg 1721 and Ala 1722.

WO 95/18827, WO 95/18828 and WO 95/18829 describe Factor VIII derivatives with modifications in the A2 region of the heavy chain.

WO 97/03193 discloses Factor VIII polypeptide analogs in which the modifications comprise alterations of the metal binding properties of the molecule.

WO 97/03195 describes Factor VIII:C polypeptide analogs in which modifications are provided on one or several amino acid residues adjacent an Arg residue.

EP-0 808 901 describes the construction of Factor VIII variants including at least one mutation in at least one immunodominant region of Factor VIII and the use of these Factor VIII variants in the treatment of patients with Factor VIII inhibitors. Those modifications do not result in an extended half-life or enhanced stability of the Factor VIII variant, neither in vivo nor in vitro.

U.S. Pat. No. 6,919,311 describes the construction of mutant Factor VIII variants with reduced affinity for LRP1 in vitro, further suggesting that these protein variants will have an increased half-life when administered in vivo.

In light of the prior art, none of the documents suggest that chemical conjugates of Factor VIII or von Willebrand Factor will display modified binding affinity for cellular clearance receptors, resulting in a reduced clearance rate of the Factor VIII protein and, consequently, an extended half-life and enhanced stability of Factor VIII. The present invention fulfills a need in the art for conjugated coagulation proteins with reduced clearance and increased half-lives in vivo.

BRIEF SUMMARY OF THE INVENTION

The present invention provides methods of increasing the survival of a coagulation protein by inhibiting the interaction with a clearance receptor. In one embodiment, the methods of the present invention comprise modifying a coagulation protein with a water soluble polymer and administering to a mammal in need thereof a therapeutically effective amount of a composition comprising the modified coagulation factor.

In one embodiment, the modified coagulation proteins of the invention are selected from those involved in the coagulation cascade. In particular embodiments, the proteins may be Factor VIII (FVIII) or Von Willebrand Factor (VWF). In one embodiment, the clearance receptor may be selected from the class of LFP receptors, vLDL receptors, LDL receptor related proteins, megalin receptors, and macrophage mannose receptors. In a particular embodiment, the clearance receptor is LRP1.

In certain embodiments, the coagulation proteins of the present invention are modified by conjugation of a water soluble polymer, such as a PEG, a PEO, a polypropylene glycol, a polyoxyalkylene, a starch, a poly-carbohydrate, a polysialic acid, and the like. In particular embodiments, the polymer may be conjugated to the coagulation protein through a linker. In other embodiments, the polymer may be linked directly to the protein. In certain embodiments, the polymer may be stably conjugated to the coagulation protein, or alternatively, conjugated to the coagulation protein through a releasable linker.

In one embodiment, the present invention provides methods of increasing the survival of Factor VIII by inhibiting the interaction with a clearance receptor. In certain embodiments, the method comprises the steps of: (a) modifying a binding protein of Factor VIII with a water soluble polymer, and (b) administering to a mammal in need thereof a therapeutically effective amount of a composition comprising the modified binding protein. In particular embodiments, the binding protein is von Willebrand Factor. In certain embodiments, the clearance receptor is LRP1. In particular embodiments, the water soluble polymer is selected from a PEG, a PEO, a polypropylene glycol, a polyoxyalkylene, a poly-carbohydrate, a polysialic acid, and the like. In still another embodiment, both Factor VIII and a binding protein of FVIII are modified with a water soluble polymer.

In another embodiment, the present invention provides methods of preparing a composition that inhibits coagulation protein clearance receptors. In certain embodiments, the methods comprise the step of modifying a coagulation protein with a water soluble polymer, wherein the modification increases the survival of the protein in blood circulation of a mammal by inhibiting coagulation protein clearance receptors. In certain embodiments of the invention, the coagulation protein is FVIII or VWF.

In one embodiment, the present invention provides modified coagulation proteins that demonstrate reduced binding to a clearance receptor and have increased half-lives in vivo. In certain embodiments, the coagulation proteins of the present invention are conjugated to water soluble polymers or carbohydrate moieties. In one embodiment, the modified coagulation proteins of the invention are selected from VWF and FVIII. In particular embodiments, the modified coagulation proteins of the invention may be plasmatic (plasma-derived) VWF or FVIII, recombinant VWF or FVIII, or a biologically active derivative of VWF or FVIII.

The present invention also provides compositions comprising modified coagulation proteins with increased survival in vivo, wherein said coagulation proteins are modified with a water soluble polymer. In certain embodiments, the modified coagulation proteins of the invention have reduced binding affinity for their clearance receptors. The present invention also provides pharmaceutical formulations of modified coagulation proteins for administration to an individual with a blood clotting disease. In certain embodiments, the pharmaceutical compositions of the present invention comprise modified FVIII, modified VWF, or both.

In another embodiment, the present invention provides methods of treating an individual with a blood clotting disease, the method comprising the step of administering to a patient in need thereof a modified coagulation protein, wherein said coagulation protein has an increased survival in vivo. In certain embodiments, the coagulation protein is FVIII, VWF, or both. In other embodiments, the coagulation protein is modified with a water soluble polymer, such as a PEG, a PEO, a polypropylene glycol, a polyoxyalkylene, a poly-carbohydrate, a polysialic acid, and the like. In one embodiment, the modified coagulation protein has a reduced binding affinity for its clearance receptor. In one particular embodiment, the clearance receptor is LRP1.

BRIEF DESCRIPTION OF THE DRAWINGS

FIG. 5. Comparison of the inhibitory binding effect of vWF and PSA-vWF on FVIII binding to LRP1 as determined by SPR analysis. PSA-vWF appears to be slightly less efficient than wt-vWF in interfering with the FVIII-LRP1 interaction.

FIG. 13. (Top Panel) Comparison of wt-rFVIII and hPEGylated-rFVIII binding (0-50 μg) to LRP1 as determined by SPR analysis. (Bottom Panel) Chemical structure of the hydrolysable PEG moiety conjugated to rFVIII.

FIG. 15. (Top Panel) Comparison of wt-rFVIII and sPEGylated-rFVIII binding (0-50 μg) to LRP1 as determined by SPR analysis. (Bottom Panel) Chemical structure of the stable PEG moiety conjugated to rFVIII.

FIG. 17. (Top Panel) Comparison of the effect of wt-VWF and sPEGylated-VWF (0-100 μg) on FVIII binding to LRP1 as determined by SPR analysis. (Middle Panel) Chemical structure of the stable PEG moiety conjugated to rFVIII. (Bottom Panel) $IC_{50}$ values for the effect of wt-VWF and sPEG-VWF on FVIII-LRP1 binding.

FIG. 18. (Top Panel) Comparison of the effect of wt-VWF and hPEGylated-VWF (0-100 μg) on FVIII binding to LRP1 as determined by SPR analysis. (Middle Panel) Chemical structure of the hydrolysable PEG moiety conjugated to rFVIII. (Bottom Panel) $IC_{50}$ values for the effect of wt-VWF and hPEG-VWF on FVIII-LRP1 binding.

DETAILED DESCRIPTION OF THE INVENTION

Figure 1:
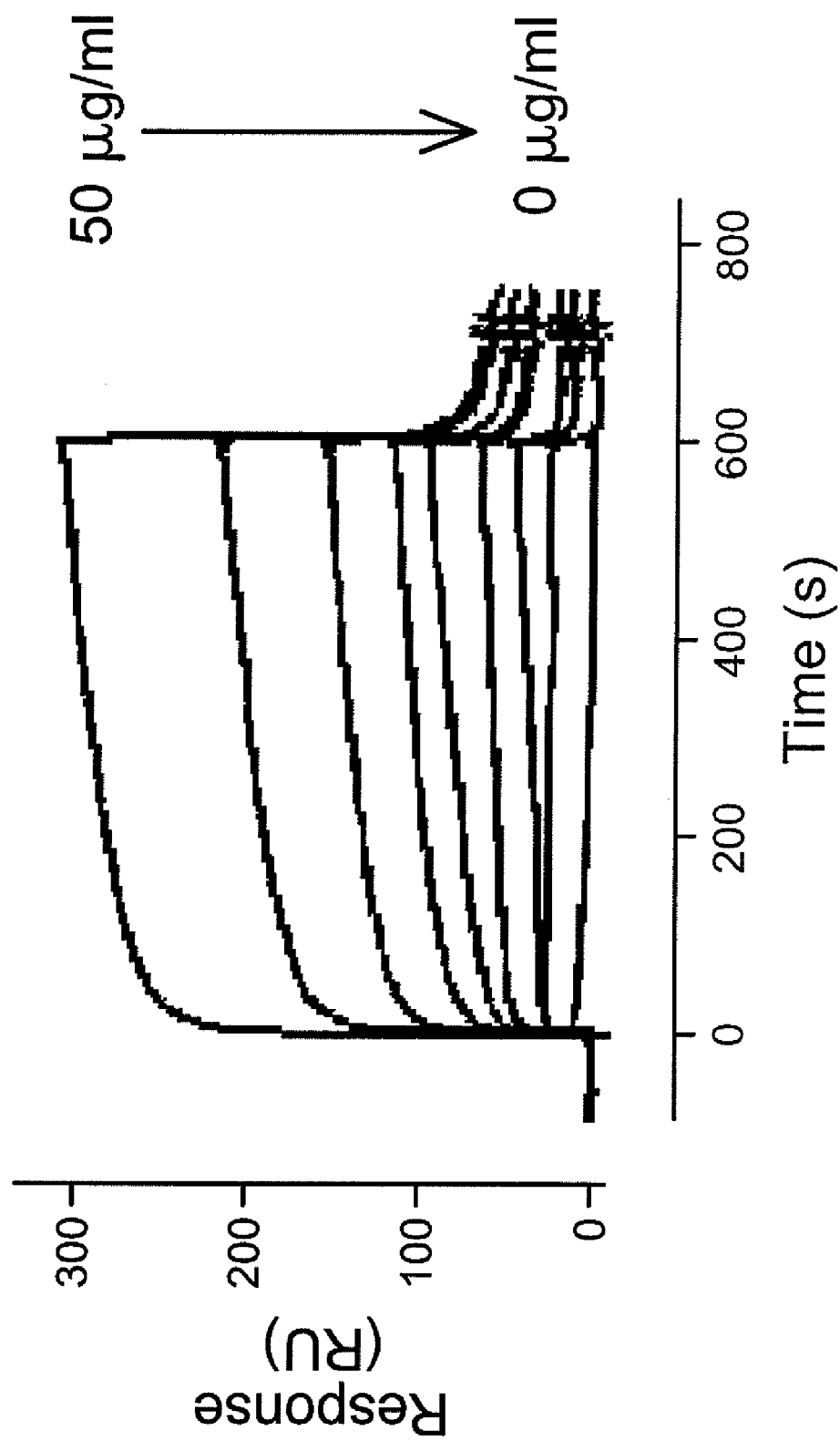
FIG. 1. SPR analysis of wt-rFVIII (0-50 μg) binding to immobilized LRP1.

The present invention provides methods of increasing the survival or half-life of a coagulation protein by inhibiting or reducing the interaction with a clearance receptor. In one embodiment, the methods of the present invention comprise modifying a coagulation protein with a water soluble polymer and administering to a mammal in need thereof a therapeutically effective amount of a composition comprising the modified coagulation factor. Coagulation proteins embraced by the present invention include those that participate in or assist in the regulation of a pathway involved in the coagulation cascade.

The coagulation proteins of the present invention may be purified from endogenous sources, such as pooled human plasma, or may be produced by recombinant means. In one embodiment, the coagulation proteins modified in the methods of the invention are selected from Factor VIII (FVIII) and Von Willebrand Factor (VWF). In a particular embodiment, the coagulation proteins are selected from recombinant Factor VIII (rFVIII) and recombinant von Willebrand Factor (rVWF).

One known clearance receptor for FVIII is LRP1. In certain embodiments, the invention provides methods of increasing the survival or half-life of FVIII by inhibiting or reducing the binding affinity of FVIII for LRP1. In some embodiments, the methods comprise administering to a mammal in need thereof a therapeutically effective amount of a modified or conjugated FVIII molecule with a reduced binding affinity for LRP1. In particular embodiments, the modified FVIII may be administered simultaneously with VWF, or in a preformed FVIII/VWF complex.

In a related embodiment, the methods of the present invention comprise the steps of: (a) modifying a binding protein of a coagulation protein with a water soluble polymer, and (b) administering to a mammal in need thereof a therapeutically effective amount of a composition comprising the modified binding protein. In one embodiment, the interaction between FVIII and the clearance receptor LRP1 is inhibited by administering to a mammal a modified VWF protein. In certain embodiments, the modified VWF is administered simultaneously with FVIII or in a preformed FVIII/VWF complex. In yet other embodiments, both FVIII and VWF are modified.

The present invention also provides methods of preparing a composition that inhibits the interaction between a coagulation protein and a clearance receptor. In certain embodiments, the methods comprise modifying a coagulation protein with a water soluble polymer, wherein the modification increases the survival of the protein in blood circulation of a mammal by inhibiting coagulation protein clearance receptors. In specific embodiments, the coagulation protein composition comprises FVIII, VWF, or a preformed FVIII/VWF complex.

In one embodiment, the present invention also provides modified or conjugated coagulation proteins that demonstrate reduced binding to their clearance receptor and have increased half-lives in vivo. In other embodiments, the invention provides pharmaceutical formulations of modified or conjugated coagulation proteins for administration to a mammal in need thereof. In particular embodiments, the formulations comprise modified FVIII, VWF, or a preformed FVIII/VWF complex.

In another embodiment, the present invention provides methods of treating an individual with a blood clotting disease, the method comprising administering to a patient in need thereof a modified coagulation protein, wherein said coagulation protein has an increased survival in vivo. The methods of the present invention may be practiced with any of the modified coagulation proteins, compositions, or formulations thereof presented herewith. In a particular embodiment, the clotting disease is Haemophilia or von Willebrand's Disease.

In one embodiment, the invention provides a method of treating an individual suffering from a disease characterized by a FVIII deficiency, by administering a modified VWF to the individual, wherein said VWF is conjugated to a water soluble polymer. In certain embodiments, the method further comprises administering FVIII to the individual. In some embodiments, the FVIII may also be modified by a water soluble polymer. In other embodiments, the FVIII is not modified by a water soluble polymer. In particular embodiments, the patient is administered a preformed VWF/FVIII complex, wherein the VWF is conjugated to a water soluble polymer. In certain embodiments, the disease may be Haemophilia or von Willebrand's Disease.

DEFINITIONS

As used herein, a "coagulation protein" refers to a protein that functions in or has a regulatory role in a pathway of the coagulation cascade that results in the cross-linking of fibrin molecules. Coagulation proteins embraced by the present invention may participate in or regulate, for example, the tissue factor or extrinsic coagulation pathway, the contact activation or intrinsic pathway, or the common final coagulation pathway. Non-limiting examples of coagulation proteins include; Factor I (fibrinogen), Factor II (prothrombin), Factor IIa (thrombin), Factor III (Tissue Factor), Factor V, Factor VI, Factor VII, Factor VIII, Factor IX, Factor X, Factor XI, Factor XII, Factor XIII, VWF, Prekallikrein, High Molecular Weight Kininogen (HMWK), Fibronectin, Antithrombin III, Heparin cofactor II, Protein C, Protein S, Protein Z, Protein Z-related Protease Inhibitor (ZPI), Plasminogen, alpha 2-antiplasmin, tissue Plasminogen Activator (tPA), Urokinase, Plasminogen Activator Inhibitor-1 (PAI1), Plasminogen Activator Inhibitor-2 (PAI2), Cancer Procoagulant, and the like. The coagulation proteins of the present invention include full-length proteins as well as matured polypeptides, activated polypeptides, precursor polypeptides, partially proteolysed polypeptides, and the like. It is understood that the coagulation proteins of the present invention include alternatively spliced forms, conservatively modified proteins, substantially identical proteins, homologues, and the like.

As used herein, a "clearance receptor" refers to a class of proteins which bind to and remove coagulation proteins from the blood or plasma of an individual, thereby reducing the effective concentration of a given coagulation protein. Generally, a clearance receptor is a membrane protein comprising at least an extracellular domain and a membrane attachment domain. In certain embodiments, a membrane protein may be a transmembrane protein, an integral membrane protein, or a peripheral membrane protein. Exemplary clearance receptors embraced by the present invention include LFP receptors, vLDL receptors, LDL receptor related proteins, megalin receptors, and macrophage mannose receptors. For example, LRP1 binds to and removes Factor VIII in vivo. One of skill in the art will know of many clearance receptors well suited for use in the present invention.

The term "water-soluble" refers to moieties that have some detectable degree of solubility in water. Methods to detect and/or quantify water solubility are well known in the art. Exemplary water-soluble polymers include peptides, saccharides, poly(vinyls), poly(ethers), poly(amines), poly(carboxylic acids) and the like. Peptides can have mixed sequences or be composed of a single amino acid, e.g., poly (lysine). An exemplary polysaccharide is poly(sialic acid) or hydroxyethyl starch. An exemplary poly(ether) is poly(ethylene glycol), e.g., m-PEG. Poly(ethylene imine) is an exemplary polyamine, and poly(acrylic) acid is a representative poly(carboxylic acid). Other water-soluble polymers that are suited for use in the present invention include polyelkylenes such as polyoxyethylene, polyoxypropylene, and block copolymers of polyoxyethylene and polyoxypropylene (Pluronics); polymethacrylates; and carbomers. One of skill in the art will know of other water-soluble polymers well suited for use in the present invention.

The polymer backbone of the water-soluble polymer can be poly(ethylene glycol) (i.e. PEG). However, it should be understood that other related polymers are also suitable for use in the practice of this invention and that the use of the term PEG or poly(ethylene glycol) is intended to be inclusive and not exclusive in this respect. The term PEG includes poly (ethylene glycol) in any of its forms, including alkoxy PEG, difunctional PEG, multiarmed PEG, forked PEG, branched PEG, pendent PEG (i.e. PEG or related polymers having one or more functional groups pendent to the polymer backbone), or PEG with degradable linkages therein.

The polymer backbone can be linear or branched. Branched polymer backbones are generally known in the art. Typically, a branched polymer has a central branch core moiety and a plurality of linear polymer chains linked to the central branch core. PEG is commonly used in branched forms that can be prepared by addition of ethylene oxide to various polyols, such as glycerol, pentaerythritol and sorbitol. The central branch moiety can also be derived from several amino acids, such as lysine. The branched poly(ethylene glycol) can be represented in general form as $R(-PEG-OH)_m$ in which R represents the core moiety, such as glycerol or pentaerythritol, and m represents the number of arms. Multiarmed PEG molecules, such as those described in U.S. Pat. No. 5,932,462, which is incorporated by reference herein in its entirety, can also be used as the polymer backbone.

Many other polymers are also suitable for the invention. Polymer backbones that are non-peptidic and water-soluble, with from 2 to about 300 termini, are particularly useful in the invention. Examples of suitable polymers include, but are not limited to, other poly(alkylene glycols), such as poly(propylene glycol) ("PPG"), copolymers of ethylene glycol and propylene glycol and the like, poly(oxyethylated polyol), poly(olefinic alcohol), poly(vinylpyrrolidone), poly(hydroxypropylmethacrylamide), poly(-hydroxy acid), poly(vinyl alcohol), polyphosphazene, polyoxazoline, poly(N-acryloylmorpholine), such as described in U.S. Pat. No. 5,629,384, which is incorporated by reference herein in its entirety, and copolymers, terpolymers, and mixtures thereof. Although the molecular weight of each chain of the polymer backbone can vary, it is typically in the range of from about 100 Da to about 100,000 Da, often from about 6,000 Da to about 80,000 Da.

The term "glycoconjugation," as used herein, refers to the enzymatically mediated conjugation of a modified sugar moiety to an amino acid or glycosyl residue of a polypeptide, e.g., a coagulation protein of the present invention. A subgenus of "glycoconjugation" is "glycol-PEGylation," in which the modifying group of the modified sugar is poly(ethylene glycol), and alkyl derivative (e.g., m-PEG) or reactive derivative (e.g., H2N-PEG, HOOC-PEG) thereof.

The term, "glycosyl linking group," as used herein refers to a glycosyl residue to which a modifying group (e.g., PEG moiety or other water-soluble polymer) is covalently attached; the glycosyl linking group joins the modifying group to the remainder of the conjugate. In the methods of the invention, the "glycosyl linking group" becomes covalently attached to a glycosylated or unglycosylated coagulation protein, thereby linking the agent to an amino acid and/or glycosyl residue on the peptide. A "glycosyl linking group" is generally derived from a "modified sugar" by the enzymatic attachment of the "modified sugar" to an amino acid and/or glycosyl residue of the coagulation protein. The glycosyl linking group can be a saccharide-derived structure that is degraded during formation of modifying group-modified sugar cassette (e.g., oxidation Schiff base formation reduction), or the glycosyl linking group may be intact. An "intact glycosyl linking group" refers to a linking group that is derived from a glycosyl moiety in which the saccharide monomer that links the modifying group and to the remainder of the conjugate is not degraded, e.g., oxidized, e.g., by sodium metaperiodate. "Intact glycosyl linking groups" of the invention may be derived from a naturally occurring oligosaccharide by addition of glycosyl unit(s) or removal of one or more glycosyl unit from a parent saccharide structure.

A "physiologically cleavable" as well as a "hydrolyzable" bond is a relatively weak bond that reacts with water (i.e., is hydrolyzed) under physiological conditions. The tendency of a bond to hydrolyze in water will depend not only on the general type of linkage connecting two central atoms but also on the substituents attached to these central atoms. Exemplary hydrolyzable bonds include, but are not limited to, carboxylate ester, phosphate ester, anhydride, acetal, ketal, acyloxyalkyl ether, imine, and ortho esters.

A "releasable linkage", or "hydrolysable linkage", or "releasable linkage" includes, but is not limited to, a physiologically cleavable bond, a hydrolyzable bond, and an enzymatically degradable linkage. Thus, a "releasable linkage" is a linkage that may undergo either hydrolysis or cleavage by some other mechanism (e.g., enzyme-catalyzed, acid-catalyzed, base-catalyzed, and so forth) under physiological conditions. For example, a "releasable linkage" can involve an elimination reaction that has a base abstraction of a proton, (e.g., an ionizable hydrogen atom, $H_\alpha$), as the driving force. For purposes herein, a "releasable linkage" is synonymous with a "degradable linkage." Thus, a releasable moiety has one or more groups (e.g., a linker) that is releasable, degradable, or capable of being removed or cleaved under physiological and/or laboratory conditions, thus releasing, e.g., the water soluble polymer from the protein, or a protecting group linked to the conjugation moiety.

An "enzymatically releasable linkage" means a linkage that is subject to degradation by one or more enzymes.

A "hydrolytically stable" linkage or bond refers to a chemical bond, typically a covalent bond, that is substantially stable in water, that is to say, does not undergo hydrolysis under physiological conditions to any appreciable extent over an extended period of time. Examples of hydrolytically stable linkages include but are not limited to the following: carbon-carbon bonds (e.g., in aliphatic chains), ethers, amides, and the like. Generally, a hydrolytically stable linkage is one that exhibits a rate of hydrolysis of less than about 1-5% per day under physiological conditions.

As used herein, a protein having a "reduced binding affinity" for a receptor refers to a modified or recombinant protein that displays partially or totally inhibited, decreased, reduced, or down-regulated interactions with a particular receptor. In the context of the present invention, a modified or recombinant coagulation protein is said to inhibit the interaction with its clearance receptor if it binds with a lower binding affinity or does not bind at all. The reduced binding of the coagulation protein may be from about a 5% to about a 100% or more reduction in the interaction with the clearance receptor. For example, the reduction may be about 5%, 10%, 20%, 30%, 40%, 50%, 60%, 70%, 80%, 90%, 100%, or more. Similarly, the inhibition of the binding between the modified or recombinant coagulation protein and clearance receptor may be about a 5%, 10%, 20%, 30%, 40%, 50%, 60%, 70%, 80%, 90%, 95%, or 100% inhibition of the interaction. In certain embodiments, the reduced interaction may be from about 1-fold to about 10-fold reduced, for example, 1-fold, 2-fold, 3-fold, 4-fold, 5-fold, 6-fold, 7-fold, 8-fold, 9-fold, 10-fold, or more reduced binding in comparison to the interaction between the wild type coagulation protein and clearance receptor. In other embodiments, the reduced interaction may be from about $10^1$-fold to about $10^5$-fold reduced, for example $10^1$-fold, $10^2$-fold, $10^3$-fold, $10^4$-fold, $10^5$-fold, or more reduced as compared to the wild type protein. Quantitative means for determining the affinity of an interaction are well known in the art and include without limitation, Surface Plasmon Resonance (SPR) analysis, Isothermal Titration Calorimetry, affinity chromatography, Fluorescence Polarization (FP) and Anisotropy (FA) assays, and the like.

As used herein, a "conjugation moiety" refers to a chemical structure comprising a water soluble polymer that is covalently attached to a protein, such as a coagulation protein as in the present invention. Conjugation moieties may further comprise one or more linking groups as well as one or more branching groups.

As used herein, "treatment" refers to clinical intervention in an attempt to alter the natural course of the individual or condition being treated, for example a blood coagulation disorder such as Haemophilia or von Willebrand's Disease, and may be performed either for prophylaxis or during the course of clinical pathology. Desirable effects include preventing occurrence or recurrence of symptoms of the disease, alleviation of symptoms, diminishment of any direct or indirect pathological consequences of the disease, lowering the rate of disease progression, amelioration or palliation of the disease state, and remission or improved prognosis.

An "effective amount" or a "therapeutically effective amount" is an amount sufficient to effect a beneficial or desired clinical result, for example, in the treatment of a disease state such as Haemophilia, von Willebrand's Disease, or a related coagulapathy. In terms of clinical response for subjects bearing a disease, an effective amount is an amount sufficient to palliate, ameliorate, stabilize, reverse, or slow progression of the disease, or otherwise reduce pathological consequences of the disease. An effective amount may be given in single or divided doses.

Non-limiting examples of coagulapathies that may be treated with the methods and compositions of the present invention include hypercoagulability diseases, such as Antithrombin III deficiency, Protein C deficiency, Activated protein C resistance, Protein S deficiency, Factor V Leiden, Hyperprothrombinemia; essential thrombocytosis; hyopcoagulability diseases, such as Hemophilia, including Types A, B, and C, Von Willebrand's disease, Hypoprothrombinemia/Factor II deficiency, Hypofibrinogenemia, Factor XIII deficiency, and the like; purpura, such as Henoch-Schönlein, idiopathic thrombocytopenic purpura (ITP), Evans syndrome, and thrombotic thrombocytopenic purpura (TTP); and thrombocytopenia, including heparin-induced thrombocytopenia.

As used herein, the terms "Hemophilia" or "Haemophilia" refer to a group of disease states broadly characterized by reduced blood clotting or coagulation. Haemophilia may refer to Type A, Type B, or Type C Haemophilia, or to the composite of all three diseases types. Type A Haemophilia (Haemophilia A) is caused by a reduction or loss of Factor VIII (FVIII) activity and is the most prominent of the Haemophilia subtypes. Type B Haemophilia (Haemophilia B) results from the loss or reduction of Factor IX (FIX) clotting function. Type C Haemophilia (Haemophilia C) is a consequence of the loss or reduction in Factor XI (FXI) clotting activity. Haemophilia A and B are X-linked diseases, while Haemophilia C is autosomal. Common treatments for Haemophilia include both prophylactic and on-demand administration of clotting factors, such as FVIII, FIX, including Bebulin®VH, and FXI, as well as FEIBA-VH, desmopressin, and plasma infusions.

As used herein, "Von Willebrand Disease" or "Von Willebrand's disease" (vWD), refers to a class of diseases characterized by a defect in the normal activity of von Willebrand Factor (vWF). The defect in vWF may include loss or reduction of function, as in Type 1, Type 3, and some Type 2 Von Willebrand Diseases, or alternatively may result from a gain of function, as in Type 2B and platelet-type vWD. In the context of the present invention, vWD may refer to any type of the disease, including Type 1, Type 2, Type 3, and platelet type vWD, any subtype of the disease, such as Type 2A, Type 2B, Type 2M, or Type 2N, or to the group of diseases as a whole.

Common treatments for VWD include administration of VWF, FVIII, and FVIII/VWF compositions and equivalents, such as Advate®, Hemophil M, MONARC-M™, and Recombinate. Other treatments include desmopressin, which can be administered orally or intravenously (DDAVP), subcutaneously (octostim), or nasally (octostim spray); cyklokapron and amicar, which help to stabilize established clots; thrombin, which can be applied directly to a site of bleeding, and general plasma infusions.

Factor VIII (FVIII) exists naturally and in therapeutic preparations as a heterogeneous distribution of polypeptides arising from a single gene product (see, e.g., Andersson et al., Proc. Natl. Acad. Sci. USA, 83, 2979-2983, May 1986). The term "Factor VIII" as used herein refers to all such polypeptides, whether derived from blood plasma or produced through the use of recombinant DNA techniques. Commercially available examples of therapeutic preparations containing Factor VIII include those sold under the trade names of HEMOFIL M and RECOMBINATE (available from Baxter Healthcare Corporation, Deerfield, Ill., U.S.A.). Other preparations currently in development comprise primarily a single subpopulation of Factor VIII molecules which lack the B domain portion of the molecule. In the context of the present invention, FVIII may be post-translationally modified, either in vivo, or in vitro, and/or conjugated to a water soluble polymer, e.g. a polyether such as a PEG, PEO, POE, and the like. In certain embodiments, the FVIII molecules of the present invention may be polysialylated, PEGylated, or otherwise post-translationally modified.

VWF and FVIII molecules particularly well suited for use in the present invention include full-length protein constructs, precursor protein constructs, biologically active fragments, subunits, or derivatives thereof, plasmonic polypeptides, recombinant polypeptides, and the like.

In certain embodiments, VWF proteins of the invention may comprise a construct, for example, prepared as in WO 1986/06096 published on Oct. 23, 1986 and U.S. patent application Ser. No. 07/559,509, filed on Jul. 23, 1990, in the name of Ginsburg et al., which is incorporated herein by reference with respect to the methods of producing recombinant VWF. The VWF useful for the present invention includes all potential forms, including the monomeric and multimeric forms. One particularly useful form of VWF are homo-multimers of at least two VWFs. The VWF proteins may be either a biologically active derivative, or when to be used solely as a stabilizer for FVIII the VWF may be of a form not biologically active. It should also be understood that the present invention encompasses different forms of VWF to be used in combination. For example, a composition useful for the present invention may include different multimers, different derivatives and both biologically active derivatives and derivatives not biologically active. In primary hemostasis VWF serves as a bridge between platelets and specific components of the extracellular matrix, such as collagen. The biological activity of VWF in this process can be measured by two different in vitro assays (Turecek et al., Semin. Thromb. Hemost. 28: 149-160, 2002). The ristocetin cofactor assay is based on the agglutination of fresh or formalin-fixed platelets induced by the antibiotic ristocetin in the presence of VWF. The degree of platelet agglutination depends on the VWF concentration and can be measured by the turbidimetric method, e.g. by use of an aggregometer (Weiss et al., J. Clin. Invest. 52: 2708-2716, 1973; Macfarlane et al., Thromb. Diath. Haemorrh. 34: 306-308, 1975). The second method is the collagen binding assay, which is based on ELISA technology (Brown et Bosak, Thromb. Res. 43: 303-311, 1986; Favaloro, Thromb. Haemost. 83: 127-135, 2000). A microtiter plate is coated with type I or III collagen. Then the VWF is bound to the collagen surface and subsequently detected with an enzyme-labeled polyclonal antibody. The last step is the substrate reaction, which can be photometrically monitored with an ELISA reader.

As used herein, "plasma-derived VWF (pdVWF)" includes all forms of the protein found in blood including the mature VWF obtained from a mammal having the property of in vivo-stabilizing, e.g. binding, of at least one FVIII molecule. However, the invention is not limited to the mature VWF. One, biologically active derivative of said pVWF is pro-VWF which contains the pro-peptide. Other forms of VWF useful for the present invention include the proteinaceous construct comprises immature VWF including the precursor VWF molecule (pre-pro-VWF) synthesized by endothelial cells and megakaryocytes, and/or the VWF propeptide (pro-VWF) and/or mature pdVWF obtained upon cleavage of the signal peptide and pro-peptide, respectively of the precursor molecule. Further examples of biologically active derivatives of pdVWF include pro-drugs which are processed or converted into the biologically active form, or is biologically active as such, truncated forms, forms having deletions, forms having substitutions, forms having additions other than pro-forms, fragments of the mature form, chimeric forms, and forms having post-translational modifications as compared to the natural form. PdVWF useful for the present invention also includes those forms not biologically active. This may be accomplished by modification of the mature VWF or other naturally occurring forms found in blood. The source for VWF useful for the invention is mammalian, including porcine and human versions.

As used herein, "recombinant VWF (rVWF)" includes VWF obtained via recombinant DNA technology. One form of useful rVWF has at least the property of in vivo-stabilizing, e.g. binding, of at least one FVIII molecule and having optionally a glycosylation pattern which is pharmacologically acceptable. Specific examples thereof include VWF without A2 domain thus resistant to proteolysis (Lankhof et al., Thromb. Haemost. 77: 1008-1013, 1997), the VWF fragment from Val 449 to Asn 730 including the glycoprotein lb-binding domain and binding sites for collagen and heparin (Pietu et al., Biochem. Biophys. Res. Commun. 164: 1339-1347, 1989). The determination of stabilizing at least one FVIII molecule can be carried out in VWF-deficient mammals according to methods known in the state in the art. The level of FVIII activity can be measured by, for instance, a chromogenic assay such as published in the European Pharmacopoeia (Ph. Eur., 3.sup.rd Ed. 1997:2.7.4).

In certain embodiments, FVIII proteins of the invention may comprise a construct, for example, prepared as in any of U.S. Pat. Nos. 4,757,006; 5,733,873; 5,250,421; and 5,919, 766, or as in EP 306 968. Generally, a FVIII protein of the invention may comprise any FVIII molecule having at least a portion of the B domain intact, and which has biological activity that is associated with wild type FVIII. For example, the construct may be a full length FVIII, a construct encoded by a nucleotide capable of hybridizing to a nucleic acid encoding Factor VIII:C. Such a protein may contain amino acid deletions at various sites between or within the domains A1-A2-B-A3-C1-C2 (U.S. Pat. No. 4,868,112). The FVIII molecule may also be an analog of native FVIII wherein one or more amino acid residues have been replaced by site-directed mutagenesis. Non-limiting example of constructs well suited for use in the methods of the present invention include, for example, those described in WO 2007/126808.

The production of rVWF or rFVIII may include any method known in the art for (i) the production of recombinant DNA by genetic engineering, e.g. via reverse transcription of RNA and/or amplification of DNA, (ii) introducing recombinant DNA into prokaryotic or eukaryotic cells by transfection, e.g. via electroporation or microinjection, (iii) cultivating said transformed cells, e.g. in a continuous or batchwise manner, (iv) expressing rVWF or rFVIII, e.g. constitutively or inducibly, and (v) isolating said rVWF or rFVIII, e.g. from the culture medium or by harvesting the transformed cells, in order to (vi) obtain purified rVWF or rFVIII, e.g. via anion or cation exchange chromatography, affinity chromatography, size exclusion chromatography, and the like.

The rVWF or rFVIII can be produced by expression in a suitable prokaryotic or eukaryotic host system characterized by producing a pharmacologically acceptable rVWF or rFVIII molecule. Examples of eukaryotic cells are mammalian cells, such as CHO, COS, HEK 293, BHK, SK-Hep, and HepG2. There is no particular limitation to the reagents or conditions used for producing or isolating rVWF or rFVIII according to the present invention and any system known in the art or commercially available can be employed.

A wide variety of vectors can be used for the preparation of the rVWF or rFVIII and can be selected from eukaryotic and prokaryotic expression vectors. Examples of vectors for prokaryotic expression include plasmids such as pRSET, pET, pBAD, etc., wherein the promoters used in prokaryotic expression vectors include lac, tre, tip, recA, araBAD, etc. Examples of vectors for eukaryotic expression include: (i) for expression in yeast, vectors such as pAO, pPIC, pYES, pMET, using promoters such as AOX1, GAP, GAL1, AUG1, etc; (ii) for expression in insect cells, vectors such as pMT, pAc5, pIB, pMIB, pBAC, etc., using promoters such as PH, p10, MT, Ac5, OpIE2, gp64, polh, etc., and (iii) for expression in mammalian cells, vectors such as pSVL, pCMV, pRc/RSV, pcDNA3, pBPV, etc., and vectors derived from viral systems such as vaccinia virus, adeno-associated viruses, herpes viruses, retroviruses, etc., using promoters such as CMV, SV40, EF-1, UbC. RSV, ADV, BPV, and actin.

The terms "polypeptide," "peptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for metbionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention. One of skill in the art will also recognize that conservative substitutions to a protein embraced by the present invention will be well tolerated, especially when made in residues not involved in active sites or required for a particular catalytic function. One of skill in the art will recognize that a plethora of conservative mutations, as well as non-conservative mutations made in regions with low homology or distal to an active site or protein binding interface, may be well tolerated and can be designed by inspection of high resolution structural information readily available in the art.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, *Proteins* (1984)).

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. A coagulation protein or complex of coagulation proteins, for example, FVIII, VWF, or FVIII/VWF, that is the predominant species present in a preparation is substantially purified. The term "purified" in some embodiments denotes that a nucleic acid or protein gives rise to essentially one band in an electrophoretic gel. In other embodiments, it means that the nucleic acid or protein is at least 50% pure, more preferably at least 60%, 65%, 70%, 75%, 80%, 85%, 90%, 95%, 96%, 97%, 98%, 99% or more pure. "Purify" or "purification" in other embodiments means removing at least one contaminant from the composition to be purified. In this sense, purification does not require that the purified compound be homogenous, e.g., 100% pure.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site http://www.ncbi.nlm.nih.gov/BLAST/ or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100, 200, 300, 400, 500, or more amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1987-2005, Wiley Interscience)).

An example of algorithms that are suitable for determining percent sequence identity and sequence similarity include the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

Conjugates and Post-Translational Modifications

Generally, the conjugation, post-translation modification, or covalent modification of the coagulation proteins of the invention include modifications of the N- or C-terminal residues as well as modifications of selected side chains, for example, at free sulfhydryl-groups, primary amines, and hydroxyl-groups. In one embodiment, the water soluble polymer is linked to the protein (directly or via a linker) by a lysine group or other primary amine. In one embodiment, the coagulation proteins of the present invention may be modified by conjugation of a water soluble polymer, including without limitation, a polyethylene glycol (PEG), a polypropylene glycol, a polyoxyalkylene, a polysialic acid, hydroxylethyl starch, a poly-carbohydrate moiety, and the like.

Water soluble polymers that may be used to modify the coagulation proteins of the present invention include linear and branched structures. The conjugated polymers may be attached directly to the coagulation proteins of the invention, or alternatively may be attached through a linking moiety. Non-limiting examples of protein conjugation with water soluble polymers can be found in U.S. Pat. Nos. 4,640,835; 4,496,689; 4,301,144; 4,670,417; 4,791,192, and 4,179,337, as well as in Abuchowski and Davis "Enzymes as Drugs," Holcenberg and Roberts, Eds., pp. 367 383, John Wiley and Sons, New York (1981), and Hermanson G., *Bioconjugate Techniques* $2^{nd}$ Ed., Academic Press, Inc. 2008.

Protein conjugation may be performed by a number of well known techniques in the art, for example, see Hermanson G., *Bioconjugate Techniques* $2^{nd}$ Ed., Academic Press, Inc. 2008. Examples include linkage through the peptide bond between a carboxyl group on one of either the coagulation protein or water-soluble polymer moiety and an amine group of the other, or an ester linkage between a carboxyl group of one and a hydroxyl group of the other. Another linkage by which a coagulation protein of the invention could be conjugated to a water-soluble polymer compound is via a Schiff base, between a free amino group on the polymer moiety being reacted with an aldehyde group formed at the non-reducing end of the polymer by periodate oxidation (Jennings and Lugowski, J. Immunol. 1981; 127:1011-8; Femandes and Gregonradis, Biochim Biophys Acta. 1997; 1341; 26-34). The generated Schiff Base can be stabilized by specific reduction with $NaCNBH_3$ to form a secondary amine. An alternative approach is the generation of terminal free amino groups on the polymer by reductive amination with $NH_4Cl$ after prior oxidation. Bifunctional reagents can be used for linking two amino or two hydroxyl groups. For example a polymer containing an amino group can be coupled to an amino group of the coagulation protein with reagents like $BS^3$ (Bis(sulfosuccinimidyl)suberate/Pierce, Rockford, Ill.). In addition heterobifunctional cross linking reagents like Sulfo-EMCS(N-ε-Maleimidocaproyloxy) sulfosuccinimide ester/Pierce) can be used for instance to link amine and thiol groups. In other embodiments, an aldehyde reactive group, such as PEG alkoxide plus diethyl acetal of bromoacetaldehyde; PEG plus DMSO and acetic anhydride, and PEG chloride plus the phenoxide of 4-hydroxybenzaldehyde, succinimidyl active esters, activated dithiocarbonate PEG, 2,4,5-trichlorophenylcloroformate and P-nitrophenylcloroformate activated PEG, may be used in the conjugation of a coagulation protein.

In yet other embodiments of the invention, various reactive groups may be used to conjugate a water-soluble polymers to a coagulation protein of the invention, for example, an imidoester, a hydroxymethyl phosphine, a carbodiimide, a N-hydroxysuccinimide ester (NHS-ester), a pentafluorophenyl ester (PFP-ester), a psoralen group, an aryl azide, a hydrazide, an isocynate, a maleimide, a pyridyl disulfide, a vinyl sulfone, and the like.

The term "sialic acid" refers to any member of a family of nine-carbon carboxylated sugars. The most common member of the sialic acid family is N-acetyl-neuraminic acid (2-keto-5-acetamido-3,5-dideoxy-D-glycero-D-galactononulopyranos-1-onic acid (often abbreviated as Neu5Ac, NeuAc, or NANA). A second member of the family is N-glycolylneuraminic acid (Neu5Gc or NeuGc), in which the N-acetyl group of NeuAc is hydroxylated. A third sialic acid family member is 2-keto-3-deoxy-nonulosonic acid (KDN) (Nadano et al. (1986) *J. Biol. Chem.* 261: 11550-11557; Kanamori et al., *J. Biol. Chem.* 265: 21811-21819 (1990)). Also included are 9-substituted sialic acids such as a 9-O—$C_1$-$C_6$ acyl-Neu5Ac like 9-O-lactyl-Neu5Ac or 9-O-acetyl-Neu5Ac, 9-deoxy-9-fluoro-Neu5Ac and 9-azido-9-deoxy-Neu5Ac. For review of the sialic acid family, see, e.g., Varki, *Glycobiology* 2: 25-40 (1992); *Sialic Acids Chemistry, Metabolism and Function*, R. Schauer, Ed. (Springer-Verlag, New York (1992)). Poly-sialic acid moieties can be conjugated to the coagulation proteins of the invention for example by the method described in U.S. Pat. No. 4,356,170, which is herein incorporated by reference. In one embodiment of the invention, the polysaccharide compound may be a naturally occurring polysaccharide, a derivative of a naturally occurring polysaccharide, or a naturally occurring polysaccharide derivative.

One type of covalent modification included within the scope of this invention comprises altering the native glycosylation pattern of the coagulation protein. Generally, altering the native glycosylation pattern of a protein refers to removing and/or adding one or more glycosylation sites to the coagulation protein such that the interaction between the coagulation protein and its clearance receptor is reduced or inhibited. Additionally, the native glycosylation pattern of a coagulation protein may be altered by quantitatively or qualitatively changing the various carbohydrate moieties present, i.e. the amount of glycosylation per molecule may be increased, or the identity of the carbohydrate moieties may be changed. In one embodiment, the coagulation proteins of the present invention may be chemically or enzymatically coupled to glycosides, for example, as in WO 87/05330 or Aplin and Wriston, CRC Crit. Rev. Biochem., pp. 259 306 (1981).

In one embodiment, the present invention provides O-linked glycosylated coagulation proteins, conjugates of these species, and methods for forming O-linked glycosylated peptides that include a selected amino acid sequence ("an O-linked glycosylation site"). Of particular interest are mutant coagulation proteins that include an O-linked glycosylation site that is not present in the corresponding wild type coagulation protein. The O-linked glycosylation site is a locus for attachment of a glycosyl residue that bears a modifying group.

In one embodiment, a polymer conjugated to a coagulation factor of the invention comprises a polysaccharide, which may be branched or unbranched. Monomer units of the polysaccharides used for conjugation include without limitation, D-mannose, D- and L-galactose, fucose, fructose, D-xylose, L-arabinose, D-glucuronic acid, sialic acid, D-galacturonic acid, D-mannuronic acid, D-glucosamine, D-galactosamine, D-glucose and neuraminic acid, and the like. Non-limiting examples of polysaccharides the may be used include homopolysaccharides and heteropolysaccharides such as lactose, amylopectin, starch, hydroxyethyl starch, amylose, dextrane sulfate, dextran, dextrins, glycogen, or the polysaccharide subunit of acid mucopolysaccharides, e.g. hyaluronic acid; polymers of sugar alcohols such as polysorbitol and polymannitol; heparin, heparin, and the like.

Figure 30D:
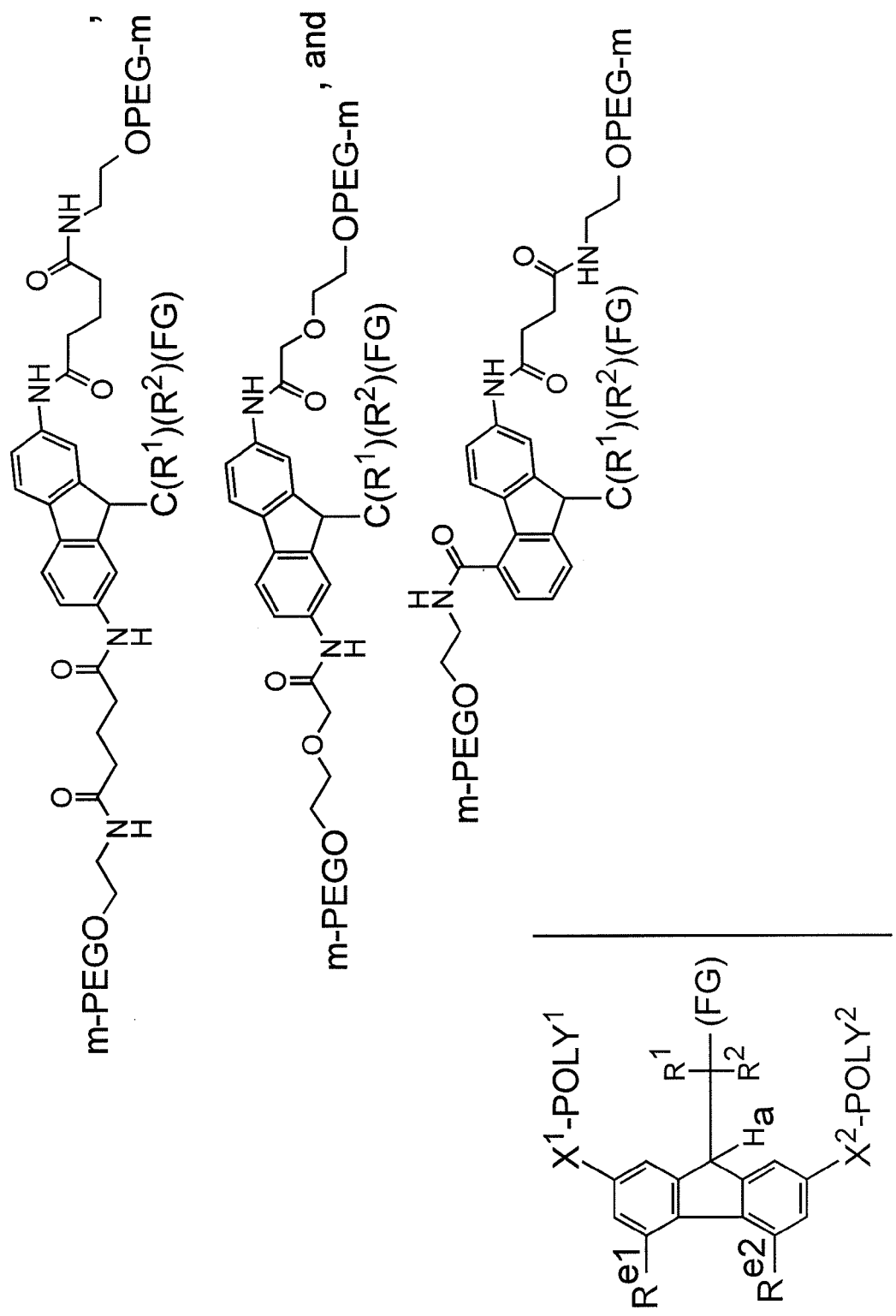
FIG. 30. Non-limiting examples of water soluble polymer moieties that are well suited for conjugation to the coagulation proteins of the present invention.
Figure 30K:
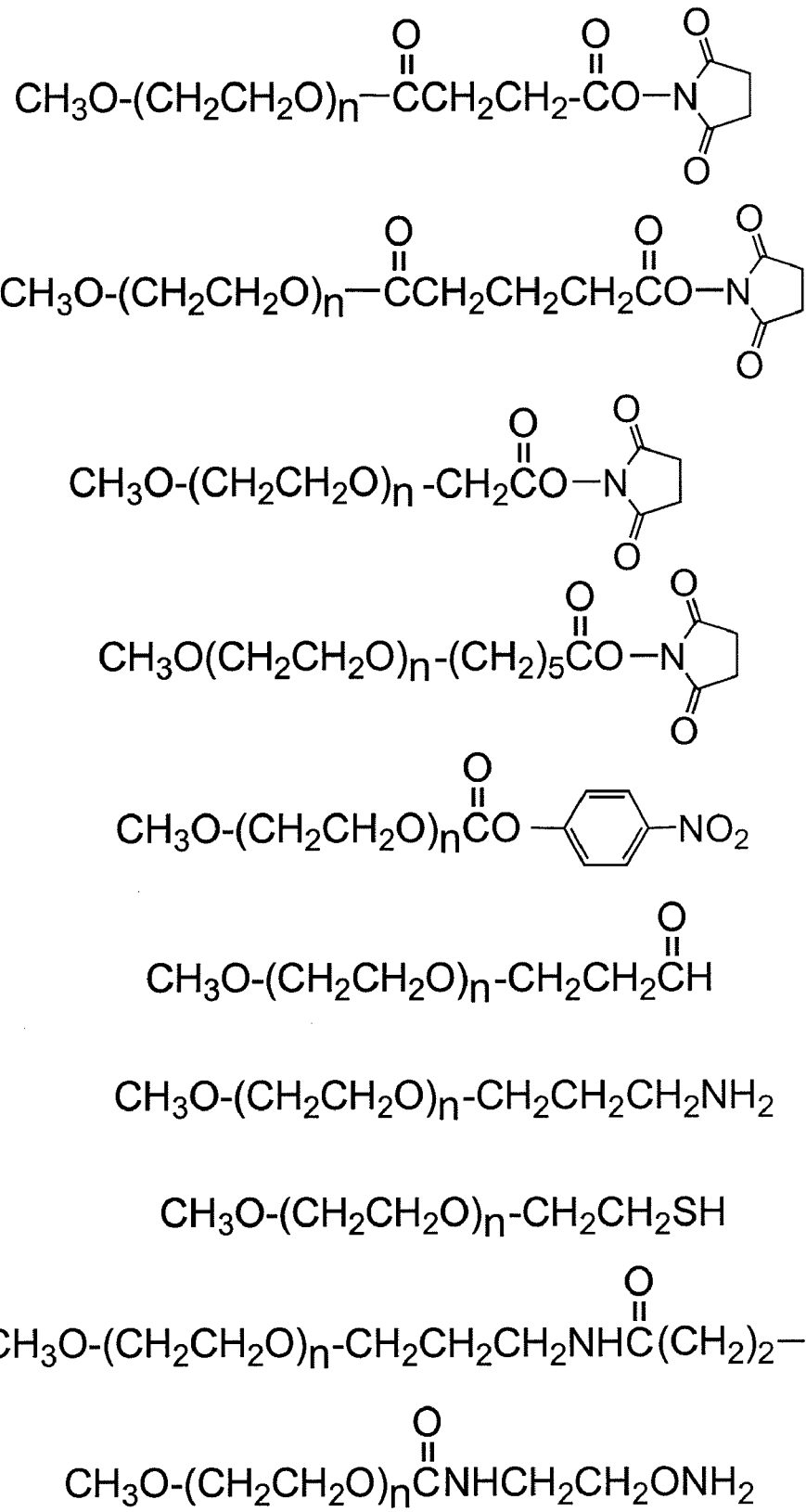
Figure 30N:
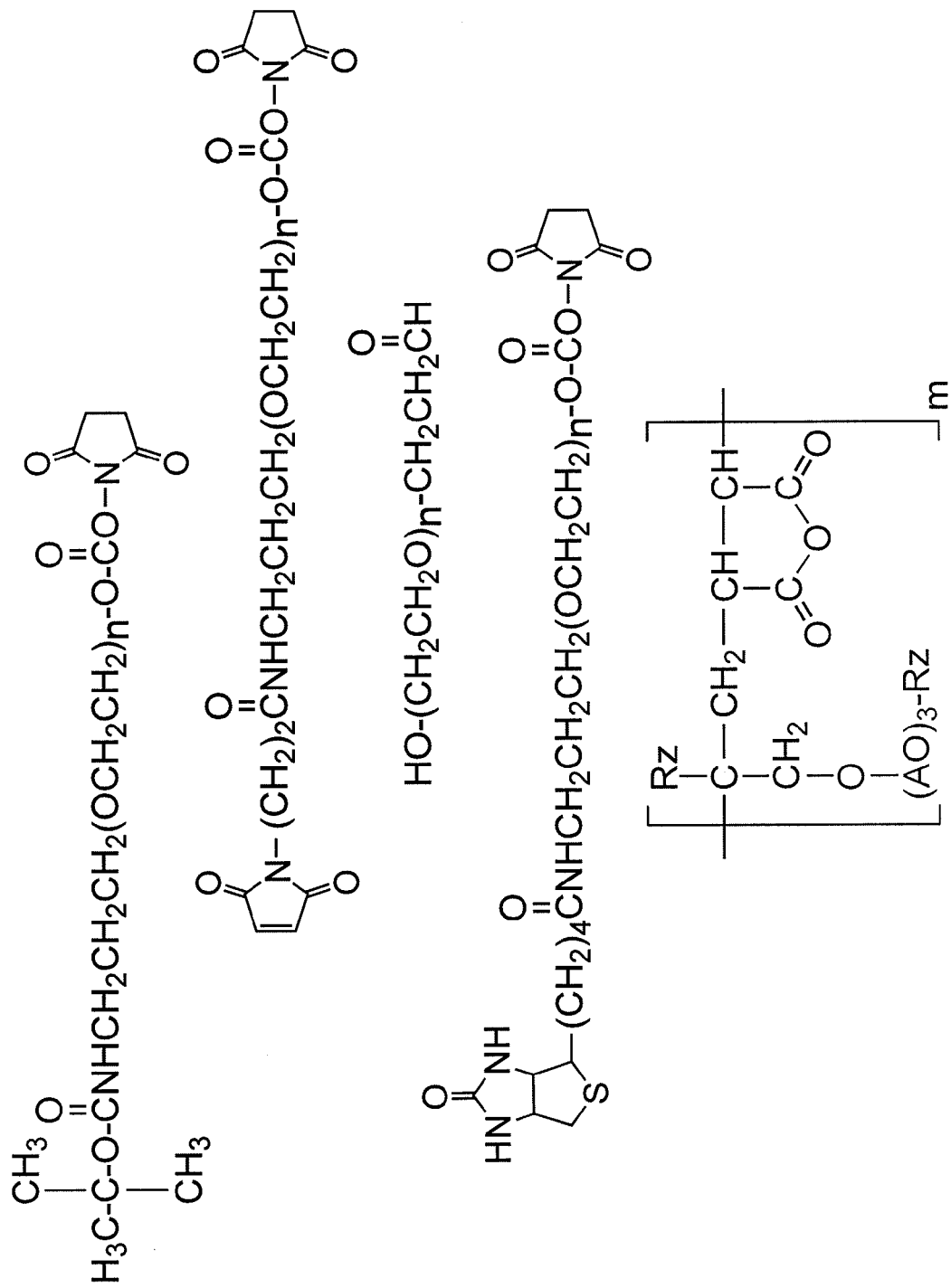

In one particular embodiment, a coagulation protein of the present invention may be conjugated to a water soluble polymer selected from those shown in FIG. 30.

Polymers used for conjugation of the coagulation proteins of the invention may have an average molecular weight of about 100 Da to about 500,000 Da. In certain embodiments, the polymers may have an average molecular weight of about 1,000 Da to about 20,000 Da. In other embodiments, the average molecular weight of the polymers may be about 1 kDa, or about 2 kDa, 3 kDa, 3.5 kDa, 4 kDa, 5 kDa, 6 kDa, 7 kDa, 8 kDa, 9 kDa, 10 kDa, 11 kDa, 12 kDa, 13 kDa, 14 kDa, 15 kDa, 16 kDa, 17 kDa, 18 kDa, 19 kDa, 20 kDa, 30 kDa, 40 kDa, 50 kDa, 75 kDa, 100 kDa, 125 kDa, 150 kDa, 200 kDa, 250 kDa, 300 kDa, 400 kDa, 500 kDa, or higher. The average molecular weight of the polymers used to conjugate the coagulation proteins of the invention will depend upon many factors, including the nature of the coagulation protein, the nature of the polymer, the degree of conjugation, and the like.

In certain embodiments, the invention comprises a coagulation protein linked to a conjugation moiety comprising a first linker group, a first branching group, and one or more water soluble polymers attached to said branching group. In other embodiments, the conjugation moiety may further comprise at least a second linking group connecting said branching group and said water soluble polymers. Suitable linking groups include, without limitation, a urethane, an amide, urea, an ester, a thioether, and the like. One of skill in the art will know of other linking groups particularly well suited for use in the present invention. In yet other embodiments, the conjugation moiety may comprise a copolymer, for example, an alternating copolymer, a periodic copolymer, a random copolymer, a block copolymer, such as a diblock or triblock, or a branched copolymer. Many conjugation moieties well suited for use with the present invention are known in the art and can be found, for example, in Hermanson G., *Bioconjugate Techniques* 2$^{nd}$ Ed., Academic Press, Inc. 2008.

In one embodiment, the coagulation proteins of the invention may be conjugated to a water soluble polymer through a reversible or hydrolysable linkage. U.S. Patent Application Publication No. 2005/0079155 describes conjugates using reversible linkages. As described in this publication, reversible linkages can be effected through the use of an enzyme substrate moiety. Another approach for reversible PEGylation is described in U.S. Pat. No. 7,060,259, which describes water-soluble prodrugs in which a biologically active agent is linked to a water-soluble non-immunogenic polymer by a hydrolyzable carbamate bond. As described therein, the biologically active agent can be readily released by the hydrolysis of the carbmate bond in vivo without the need for adding enzymes or catalytic materials. A different approach for the conjugation of reversible moieties is described by Peleg-Schulman (2004) J. Med. Chem. 47:4897-4904, WO 2004/089280 and U.S. Patent Application Publication No. 2006/0171920. Although this approach has been applied to a limited number of active agents, these references ignore other active agents for which reversible PEGylation would be particularly suited. Yet another releasable approach is described in U.S. Patent Application Publication No. 2006/0293499.

In one embodiment, the present invention provides modified coagulation proteins with the general structure:

$$R\text{-}L_1\text{-}X_1$$

wherein R is a coagulation protein, $L_1$ is a linking group, and $X_1$ is a water soluble polymer.

Examples of coagulation moieties that are well suited for use in the present invention can be found, for example, in U.S. Patent Application No. 20060293499, which describes the use of conjugation moieties with degradable linkages; WO 2004/089280, which describes the use of reversible PEGylation moieties, including PEGylation moieties coupled to proteins through a 9-hydroxymethyl-7-sulfofluorene-N-hydroxysuccinimide linkage (PEG-FMS), U.S. Patent Application No. 20050009988, which describes the use of various linking moieties that may be used to couple a polymer with a coagulation protein of the present invention; U.S. Pat. No. 5,672,662, which describes the use of monosubstituted Poly(ethylene glycol) and related moieties for protein conjugation; U.S. Patent Application No. 20060171920, which describes the use of modifying groups that are sensitive to mild basic conditions, such as Fmoc and 2-sulfo-9-fluorenylmethoxycarbonyl (FMS), for conjugation of polymers to proteins; U.S. Patent Application Nos. 20040235723 and 20080058504, which describe polymer conjugates of FVIII; and U.S. Patent Application No. 20060160948, which describes VWF and FVIII polymer conjugates; all of which are herein incorporated by reference in their entirety for all purposes. In certain embodiments, the methods of the invention may be practiced using the modified coagulation proteins described in, for example, WO 2008/082669 or WO 2007/126808, which are herein incorporated by reference in their entirety for all purposes.

The conjugates of the present invention may comprise a variety of formulae. In one embodiment, a conjugate of the invention may comprise the general formula;

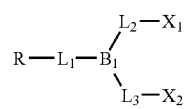

wherein R is a coagulation protein, $L_1$, $L_2$, and $L_3$ are linker moieties, $B_1$ is a first branching moiety, and $X_1$ and $X_2$ are water soluble polymer groups. In certain embodiments, $L_1$, $L_2$, and $L_3$ are optional. In particular embodiments, the conjugation moiety may be chemically stable. In other embodiments, the conjugation moieties used in the present invention may be hydrolysable. In certain embodiments, $L_1$ or $B_1$ may comprise a protecting group, such as an alcohol protecting group, an amine protecting group, a carbonyl protecting group, a carboxylic protecting group, and the like.

In a particular embodiment, the protecting group is a substituted Fmoc group. In one embodiment, a conjugate of the invention may comprise the formula;

wherein, POLY¹ is a first water-soluble polymer; POLY² is a second water-soluble polymer; X¹ is a first spacer moiety; X² is a second spacer moiety; $H_\alpha$ is an ionizable hydrogen atom; R¹ is H or an organic radical; R² is H or an organic radical; (a) is either zero or one; (b) is either zero or one; $R^{e1}$, when present, is a first electron altering group; $R^{e2}$, when present, is a second electron altering group; and Y¹ is O or S; Y² is O or S; and R is a coagulation protein.

In one specific embodiment, the present invention provides a conjugate of a coagulation protein comprising the structure;

wherein R is a coagulation protein, L₁ and L₂ are linkers, and X₁ and X₂ are water soluble polymers. In other embodiments, the conjugation moieties of the present invention may be one of those shown in FIG. 13 or 15. In certain embodiments, the conjugation moiety may be conjugated at an amino acid side, at the carboxy-terminus of the protein, or at the amino-terminus of the protein. In certain embodiments, the water soluble moieties are conjugated to a side chain at a free sulfhydryl-group, a primary amine, a hydroxyl-group, or a combination thereof. In a particular embodiment, the water soluble protein is VWF or FVIII.

In one embodiment, the present invention provides a conjugate of a coagulation protein comprising the structure;

wherein R is a coagulation protein and m-PEGO is a PEG moiety, or other water soluble polymer, connected to the remainder of the structure through an ether linkage. In certain embodiments, the conjugation moiety may be conjugated at an amino acid side, at the carboxy-terminus of the protein, or at the amino-terminus of the protein. In certain embodiments, the water soluble moieties are conjugated to a side chain at a free sulfhydryl-group, a primary amine, a hydroxyl-group, or a combination thereof. In a particular embodiment, the water soluble protein is VWF or FVIII.

In one specific embodiment, the present invention provides a conjugate of a coagulation protein comprising the structure;

wherein R is a coagulation protein. In certain embodiments, the conjugation moiety may be conjugated at an amino acid side, at the carboxy-terminus of the protein, or at the amino-terminus of the protein. In certain embodiments, the water soluble moieties are conjugated to a side chain at a free sulfhydryl-group, a primary amine, a hydroxyl-group, or a combination thereof. In a particular embodiment, the water soluble protein is VWF or FVIII.

In one specific embodiment, the present invention provides a conjugate of a coagulation protein comprising the structure;

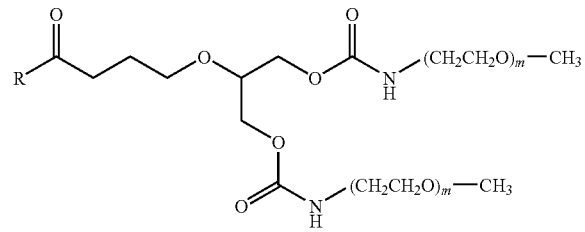

wherein R is a coagulation protein. In certain embodiments, the conjugation moiety may be conjugated at an amino acid side, at the carboxy-terminus of the protein, or at the amino-terminus of the protein. In certain embodiments, the water soluble moieties are conjugated to a side chain at a free sulfhydryl-group, a primary amine, a hydroxyl-group, or a combination thereof. In a particular embodiment, the water soluble protein is VWF or FVIII.

In yet another embodiment, the present invention provides a conjugate of a coagulation protein comprising the structure;

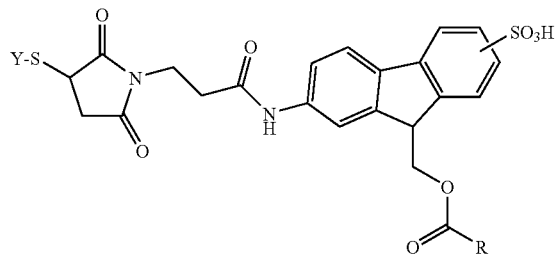

wherein R is a coagulation protein and Y is a water soluble polymer, such as a PEG. In certain embodiments, the conjugation moiety may be conjugated at an amino acid side, at the carboxy-terminus of the protein, or at the amino-terminus of the protein. In certain embodiments, the water soluble moieties are conjugated to a side chain at a free sulfhydryl-group, a primary amine, a hydroxyl-group, or a combination thereof. In a particular embodiment, the water soluble protein is VWF or FVIII.

In yet another embodiment, the present invention provides a conjugate of a coagulation protein comprising the formula;

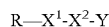

wherein R is a coagulation protein, $X^1$ is selected from the group consisting of NH, S, CO, COO, $CH_2$, $SO_2$, $SO_3$, $PO_2$, and $PO_3$, $X^2$ is a bond or linker which connects the water soluble moiety to $X^1$, and Y is a water soluble moiety. In a specific embodiment, the water soluble moiety is a PEG. In certain embodiments, the conjugation moiety may be conjugated at an amino acid side, at the carboxy-terminus of the protein, or at the amino-terminus of the protein. In certain embodiments, the water soluble moieties are conjugated to a side chain at a free sulfhydryl-group, a primary amine, a hydroxyl-group, or a combination thereof. In a particular embodiment, the water soluble protein is VWF or FVIII.

The modified or conjugated coagulation proteins of the present invention are considered to be "substantially uniformly modified" generally if at least about 40% of the proteins in a given batch or solution are modified to the same extent. In other embodiments, the coagulation proteins in a uniformly modified batch or solution may be about 50%, 60%, 70%, 80%, 90%, 95%, 99%, or higher modified to the same extent. In certain embodiments, the extent of protein modification may be determined in terms of number of moles of modifying polymer per number of moles of protein. For example, a modified coagulation protein of the invention may be conjugated by about 1 to about 30 water soluble polymers. In certain embodiments, a coagulation protein of the invention may comprise about 1, or about 2, 3, 4, 5, 6, 7, 8, 9, 10, 11, 12, 13, 14, 15, 16, 17, 18, 19, 20, 25, 30, or more moles of conjugated polymer per mol protein. Typically, the extent of modification occurring in a conjugation reaction can be controlled. For example, an average reaction may result in a variation in the extent of conjugation of less than about 50%. In other embodiments, the variation in the extent of conjugation may be less than about 40%, or less than about 35%, 30%, 25%, 20%, 15%, 10%, or 5%. Alternatively, the variation in the extent of conjugation for a particular batch of coagulation protein, may further be controlled by fractionation after the conjugation reaction, for example by size exclusion chromatography. Thus, small amounts of variation in the extent of conjugation may be achieved. In other embodiments, the extent of modification may be expressed in terms of the percent of potential conjugation sites that are modified. For example, a coagulation protein may be from about 1% to about 100% modified. In certain embodiments, the conjugates of the present invention may be about 1%, 2%, 3%, 4%, 5%, 10%, 15%, 20%, 25%, 30%, 40%, 50%, 60%, 70%, 80%, 90%, 95%, 98%, 99%, or more modified.

Compositions and Formulations

In certain embodiments, the coagulation protein compositions of the present invention, i.e. FVIII, vWF, or FVIII/vWF, further comprise bulking agents, stabilizing agents, buffering agents, sodium chloride, calcium salts, and, advantageously, other excipients. These excipients have been chosen in order to maximize the stability of Factor VIII in lyophilized preparations. However, the blood factor compositions of the present invention exhibit stability in the liquid state as well.

As used herein, a "bulking agent" refers to a chemical entity which provides structure to the "cake" or residual solid mass of a pharmaceutical preparation after it has been lyophilized and which protect it against collapse. A "crystallizable bulking agent" shall mean a bulking agent as described herein which can be crystallized during lyophilization, other than sodium chloride. Particularly well suited bulking agents for use in the present invention include, without limitation, mannitol, glycine, alanine, and hydroxyethyl starch (HES).

The bulking agents used in the present formulations, which form the crystalline portion of a lyophilized product (except in the case of HES), are selected from the group consisting of mannitol, glycine, alanine, hydroxyethyl starch (HES), and the like. One of ordinary skill will know of other bulking agents particularly well suited for use with the present invention. Mannitol, glycine, or alanine are present in an amount of about 1% to about 15%. In certain embodiments, the amount is about 1%, 2%, 3%, 4%, 5%, 6%, 7%, 8%, 9%, 10%, 11%, 12%, 13%, 14%, 15%, or more. When HES is used as a bulking agent, it is present in an amount of about 1% to about 10%. In certain embodiments, the amount is about 1%, 2%, 3%, 4%, 5%, 6%, 7%, 8%, 9%, 10%, or more HES.

In some embodiments, the stabilizing agents used in the formulations of the present invention are selected from the group consisting of sucrose, trehalose, raffinose, sorbitol, glycerol, arginine, or the like. One of ordinary skill will know of other stabilizers particularly well suited for use with the present invention. These agents are present in the formulations of the present invention in an amount of about 1% to about 10%. In certain embodiments, the amount is about 1%, 2%, 3%, 4%, 5%, 6%, 7%, 8%, 9%, 10%, or more stabilizing agent.

Various physiologically compatible salts may also be used in the formulations of the present invention. In one embodiment of the invention, sodium chloride is included in the present formulations in an amount of about 100 to about 300 mM, or from about 150 to about 250 mM, or about 225 mM. In one embodiment of the present invention, sodium chloride itself can be used without any of the aforementioned bulking agents, in which case it would be included in the formulation in an amount of between about 300 mM and about 500 mM NaCl. In certain embodiments of the invention, a physiologically compatible salt may be used at about 50 to about 1000 mM. In other embodiments, the concentration of salt in the formulation may be about 50 mM, or about 100, 150, 200, 250, 300, 350, 400, 450, 500, 600, 700, 800, 900, 1000 mM or higher. It is understood that the pharmaceutically acceptable salts are non-toxic. Additional information on suitable pharmaceutically acceptable salts can be found in Remington's Pharmaceutical Sciences, 17th ed., Mack Publishing Company, Easton, Pa., 1985, which is incorporated herein by reference.

In some embodiments, the compositions of the present invention will include a buffer at concentration of from about 10 mM to about 200 mM. In other embodiments, the buffer concentration will be from about 10 mM to about 50 mM. In yet other embodiments, the compositions of the present invention may comprise about 10 mM, 20 mM, 30 mM, 40 mM, 50 mM, 75 mM, 100 mM, 125 mM, 150 mM, 175 mM, 200 mM, or more buffer. Buffers well suited for use in the present invention include, without limitation, histidine, Tris, BIS-Tris Propane, PIPES, MOPS, HEPES, MES, ACES, and the like. One of skill in the art will know of other buffers that are particularly well suited for use in the compositions of the present invention. The compositions of the present invention may further comprise an antioxidant.

As used herein, "administering" means oral administration, administration as a suppository, topical contact, intravenous, intraperitoneal, intramuscular, intralesional, intranasal or subcutaneous administration, or the implantation of a slow-release device e.g., a mini-osmotic pump, to a subject. Administration is by any route including parenteral, and transmucosal (e.g., oral, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

Formulations suitable for parenteral administration, such as, for example, by intraarticular (in the joints), intravenous, intramuscular, intratumoral, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally. The formulations of compounds can be presented in unit-dose or multi-dose sealed containers, such as ampules and vials. Injection solutions and suspensions can be prepared from sterile powders, granules, and tablets.

In certain embodiments, the pharmaceutical preparation is in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. The composition can, if desired, also contain other compatible therapeutic agents.

Pharmaceutically acceptable carriers are determined in part by the particular composition being administered, as well as by the particular method used to administer the composition. Accordingly, there are a wide variety of suitable formulations of pharmaceutical compositions of the present invention (see, e.g., *Remington's Pharmaceutical Sciences*, 20$^{th}$ ed., 2003, supra). As used herein, "pharmaceutically acceptable carrier" includes any material, which when combined with the conjugate retains the conjugates' activity and is non-reactive with the subject's immune systems. Examples include, but are not limited to, any of the standard pharmaceutical carriers such as a phosphate buffered saline solution, water, emulsions such as oil/water emulsion, and various types of wetting agents. Other carriers may also include sterile solutions, tablets including coated tablets and capsules. Typically such carriers contain excipients such as starch, milk, sugar, certain types of clay, gelatin, stearic acid or salts thereof, magnesium or calcium stearate, talc, vegetable fats or oils, gums, glycols, or other known excipients. Such carriers may also include flavor and color additives or other ingredients. Compositions comprising such carriers are formulated by well known conventional methods.

Effective dosage forms, modes of administration and dosage amounts of the composition of the invention may be determined empirically, and making such determinations is within the skill of the art. It is understood by those skilled in the art that the dosage amount will vary with the particular composition employed, the condition being treated, the severity of the condition, the route of administration, the rate of excretion, the duration of the treatment, the identity of any other drugs being administered to the mammal, the age, size and species of the mammal, and like factors well known in the medical and veterinary arts. In general, a suitable daily dose of a compound of the present invention will be that amount which is the lowest dose effective to produce a therapeutic effect. However, the total daily dose will be determined by an attending physician or veterinarian within the scope of sound medical judgment. If desired, the daily dose may be administered in multiple sub-doses, administered separately at appropriate intervals throughout the day.

EXAMPLES

Example 1

It has been shown that LRP1 contributes to the regulation of FVIII plasma levels. LRP1 is a cellular receptor that is able to bind and transport FVIII to intracellular degradation pathways. The present example, demonstrates that PEGylation or polysialylation of FVIII disrupts in vitro binding to LRP1.

Components: Purified recombinant wild-type FVIII (batch MOQ-Hepes-08E; 2.28 mg/ml; 12117 IU/ml); PEGylated FVIII (batch hydrolysable PEG-rFVIII ORHLUFB07001PHR; 1.76 mg/ml; 2498 IU/ml); polysialylated FVIII (batch PSA-rFVIII-11.0 KD NHS; 0.613 mg/ml; 268 IU/ml). Purified LRP1 was obtained from Biomac (Leipzig; Cat no. #04-03).

Experimental design: Binding of FVIII or its derivatives to LRP1 was assessed using surface plasmon resonance (SPR) analysis using Biacore2000 equipment. Specifications: LRP1 was immobilized on a standard CM5-biosensorchip (Biacore). The flow rate was set at 20 μl/min to avoid potential rebinding due to mass-transfer limitations. Samples were run in buffer containing 0.005% Tween-20, 150 mM NaCl, 2 mM $CaCl_2$, and 20 mM Hepes (pH 7.4) at 25° C. Proteins were diluted on basis of protein content. Proteins were injected for 10 minutes to allow equilibrium to be reached, and dissociation was followed for an additional 2.5 minutes. Data analysis involved plotting of the response at equilibrium versus protein concentration. Since the experimental system is sensitive to changes in buffer composition during the analysis (buffer-refraction index), all preparations to be injected were designed to contain similar buffer compositions. Thus, for comparison between wt-FVIII and PEG-FVIII, equal amounts of the respective buffers were present in the final preparations. An example of an experimental set-up for wt-rFVIII and hydrolysable PEG-FVIII is provided in Table 1.

TABLE 1

Dillution series for a typical LPR1 binding assay.

| | pre-dillution | μl Sample | μl rFVIII buffer | μl PEG-FVIII buffer | μl system buffer | total volume (μl) |
|---|---|---|---|---|---|---|
| rFVIII (μg/ml) | | | | | | |
| 0 | — | 0.0 | 12.28 | 22.84 | 244.88 | 280 |
| 0.1 | 1/1000 | 12.28 | 0.0 | 22.84 | 244.88 | 280 |
| 0.5 | 1/100 | 6.14 | 6.14 | 22.84 | 244.88 | 280 |
| 1.0 | 1/10 | 12.28 | 0.0 | 22.84 | 244.88 | 280 |
| 2.5 | 1/10 | 3.07 | 9.21 | 22.84 | 244.88 | 280 |
| 5.0 | 1/10 | 6.14 | 6.14 | 22.84 | 244.88 | 280 |
| 10 | 1/10 | 12.28 | 0.0 | 22.84 | 244.88 | 280 |
| 25 | — | 3.07 | 9.21 | 22.84 | 244.88 | 280 |
| 50 | — | 6.14 | 6.14 | 22.84 | 244.88 | 280 |
| PEG-FVIII (μg/ml) | | | | | | |
| 0 | — | 0.0 | 12.28 | 22.84 | 244.88 | 280 |
| 0.1 | 1/100 | 4.57 | 12.28 | 18.27 | 244.88 | 280 |
| 0.5 | 1/10 | 2.28 | 12.28 | 20.56 | 244.88 | 280 |
| 1.0 | 1/10 | 4.57 | 12.28 | 18.27 | 244.88 | 280 |
| 2.5 | 1/10 | 11.42 | 12.28 | 11.42 | 244.88 | 280 |
| 5.0 | — | 2.28 | 12.28 | 20.56 | 244.88 | 280 |
| 10 | — | 4.57 | 12.28 | 18.27 | 244.88 | 280 |
| 25 | — | 11.42 | 12.28 | 11.42 | 244.88 | 280 |
| 50 | — | 22.84 | 12.28 | 0.0 | 244.88 | 280 |

Figure 2:
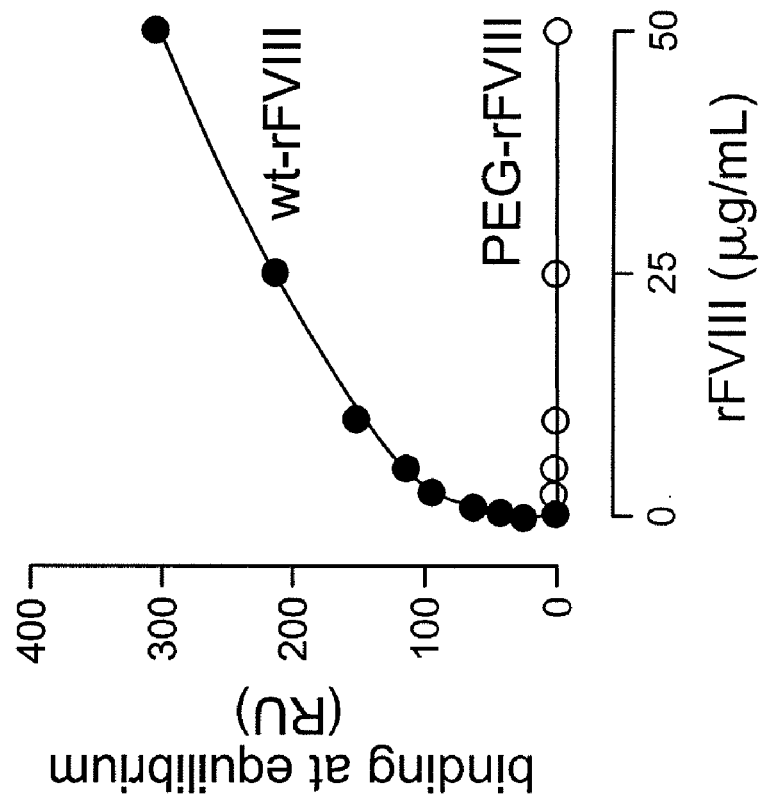
FIG. 2. Comparison of wt-FVIII and hPEGylated-FVIII binding to immobilized LRP1 as determined by SPR analysis.
Figure 3:
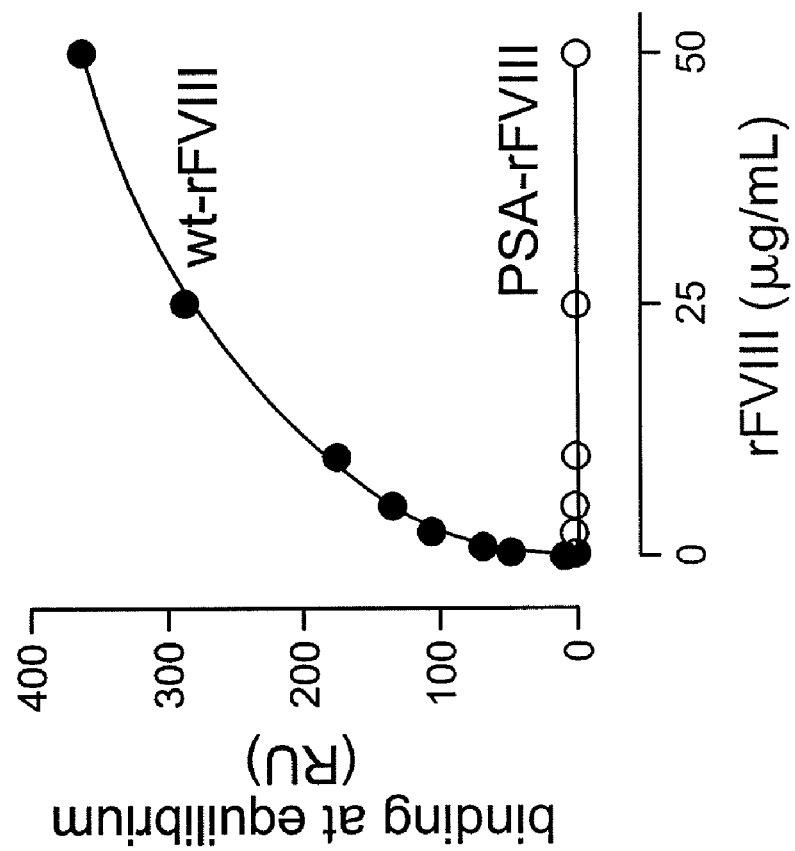
FIG. 3. Comparison of wt-FVIII and PSA-FVIII binding to immobilized LRP1 as determined by SPR analysis.

As an example, raw sensorgram-data for the binding of wt-rFVIII to immobilized LRPI is depicted in FIG. 1. In agreement with published data (eg. Lenting et al 1999, JBC 274:23734), FVIII binds efficiently to LRP1 in a dose-dependent manner. It appeared that 10-min injections are indeed sufficient to allow equilibrium to be reached. In FIGS. 2 and 3, typical equilibrium-responses are depicted for PEG-FVIII and PSA-FVIII, respectively. Strikingly, no binding of PEG-FVIII or PSA-FVIII to immobilized LRP1 could be detected, even at concentrations of 50 μg/ml (corresponding to 50-fold the normal plasma concentration).

Example 2

Binding of FVIII to LRP1 is inhibited in the presence of VWF, because LRP1 interaction sites within the FVIII light chain are inaccessible when FVIII is bound to VWF. The present example demonstrates that PEGylation or polysialylation of vWF does not interfere with the vWF-mediated inhibition of LRP1 binding by FVIII.

Components: Purified recombinant wild-type FVIII (batch MOQ-Hepes-08E; 2.28 mg/ml; 12117 IU/ml); recombinant-wt-vWF (batch ORWSEC06006F1HL; 0.464 mg/ml; 72.1 IU Ag/ml; 20.6 IU RCo/ml), stable PEG-vWF (batch NTT-VWF-600-S2 I; 1.021 mg/ml; 61.4 IU Ag/ml; 41.9 IU RCo/ml); and stable PSA-vWF (batch PSA-RVWF-19.3 KD CAO batch2 (Oct. 6, 2006); 0.0087 mg/ml; 11.3 IU Ag/ml; 0.2 IU RCo/ml).

Wild-type recombinant FVIII (40 nM) was pre-incubated with various concentrations of vWF (0-400 nM for wt-vWF and PEG-vWF and 0-200 nM for PSA-vWF). Concentrations of vWF were based on protein concentrations and a molecular weight of 250 kDa per vWF monomer. Again, since the various proteins were in different buffers, dilution-schemes were designed in such a way that buffer-compositions remained equal throughout the analysis. Mixtures of FVIII/vWF were applied to LRP1 (immobilized on a CM5-biosensorchip) at a flow rate of 20 μl/min in system-buffer containing 0.005% Tween-20, 150 mM NaCl, 2 mM $CaCl_2$, 20 mM Hepes (pH 7.4) at 25° C.

Figure 4:
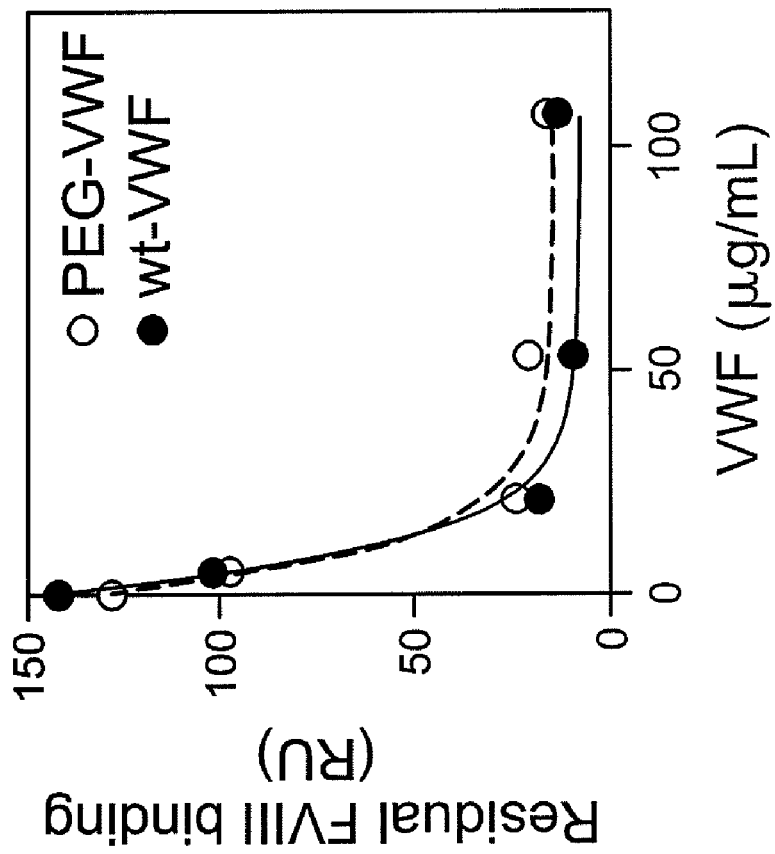
FIG. 4. Comparison of the inhibitory binding effect of vWF and PEGylated-vWF on FVIII binding to LRP1 as determined by SPR analysis. Similar inhibition is seen for both vWF constructs.

In the absence of vWF, efficient binding of FVIII to LRP1 was observed. However, increasing concentrations of vWF resulted in a concordant decrease in binding of FVIII to LRP1. As for PEG-vWF, this modulated protein appeared to be as efficient as wt-vWF in interfering with the FVIII-LRP1 interaction (FIG. 4). Although PSA-vWF also interfered with LRPI-binding (FIG. 5), this conjugated protein seemed slightly less efficient than wt-vWF. However, these data are based on a single range of concentrations, and additional experiments need to be performed to determine whether this difference is within the experimental range, or whether it represents a true decrease in capacity to inhibit the FVIII/LRP1 interaction. Nevertheless, since both conjugations affected the capacity of vWF to inhibit binding of FVIII to LRP1 to only a minor extent, if any, these data also indicate that conjugating vWF by either PEG or PSA does not affect the ability of vWF to interact with FVIII to a major extent, if at all.

Apart from functioning as a carrier-protein for FVIII, vWF also plays a critical role in the recruitment of platelets to sites of vascular injury. VWF acts as a molecular bridge between the subendothelial matrix and the platelet Glycoprotein (Gp)-Ib/IX/V receptor complex. In order to interact with GpIbα, vWF needs to be converted from a cryptic into an active conformation. Since chemical modulation of vWF may affect the exposure of the GpIbα binding site, we have tested binding of wt-vWF and its conjugated derivatives to GpIbα (both in the absence and presence of Botrocetin) and to nanobody AU/vWFa-11, an antibody fragment which displays preferential binding to vWF in its active conformation.

Components: recombinant-wt-vWF (batch ORWSEC06006F1HL; 0.464 mg/ml; 72.1 IU Ag/ml; 20.6 IU RCo/ml), stable PEG-vWF (batch NTT-vWF-600-S2 I; 1.021 mg/ml; 61.4 IU Ag/ml; 41.9 IU RCo/ml); and stable PSA-vWF (batch PSA-RvWF-19.3 KD CAO batch2 (Oct. 6, 2006); 0.0087 mg/ml; 11.3 IU Ag/ml; 0.2 IU RCo/ml).

Recombinant GpIbα (comprising residues 1-290) has been described previously (Huizinga et al (2002) Science 2973176). Botrocetin was obtained from Kordia BV (Leiden, the Netherlands). Anti-GpIbα antibody 2D4 was kindly provided by Dr. H. Deckmyn (Kortrijk, Belgium). Nanobody AU/vWFa-11 has been described previously (Hulstein et al 2005 Blood 106:3035). HRP-conjugated Polyclonal anti-vWF antibodies were purchased from Dako (Glostrup, Denmark).

Figure 6:
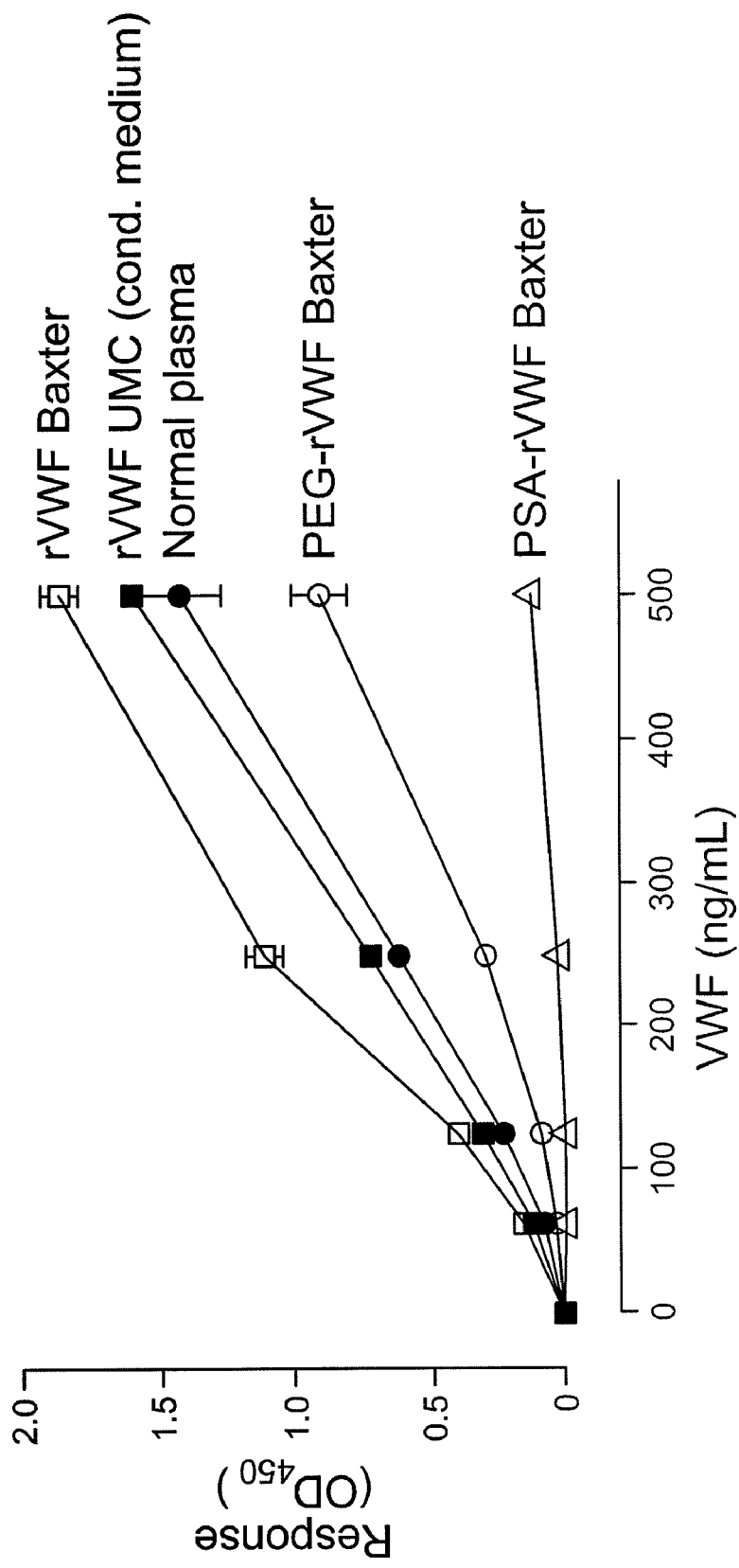
FIG. 6. Comparison of rVWF, natural VWF, and conjugated VWF binding to GpIbα in the presence of botrocetin, as determined by SPR analysis. Binding of PEGylated-VWF to GpIbα is reduced by approximately 50%, whereas PSA-VWF virtually lacks the ability to bind GpIbα in a botrocetin-dependent manner.

Binding to GpIbα and AU/vWFa-11 were performed in an immunosorbent assay, essentially as described (van Schooten et al 2005, JTH 3:2228 and Hulstein et al 2005 Blood 106: 3035, respectively). In the absence of botrocetin, no binding of wt-vWF or its conjugated derivatives (up to 1 µg/ml) to GpIba could be observed. Thus, in none of the preparations tested (including wt-vWF), vWF molecules appear to be presence that are able to spontaneously interact with GpIbα. The presence of botrocetin, however, is sufficient to induce efficient binding to GpIbα in the case of wt-vWF (FIG. 6). In fact, it seems that wt-vWF provided by Baxter is slightly more efficient than VWF present in normal pooled plasma, or recombinant VWF that is produced in a university laboratory setting. Conjugation of vWF diminishes botrocetin-induced GpIbα binding as both PEG-vWF and PSA-vWF bind with lower affinity to GpIBα as compared to non-conjugated vWF. PEG-vWF bound with approximately 2-fold less affinity than wt-vWF, whereas PSA-vWF was virtually unable to bind to GpIbα in the presence of botrocetin. The fact that PSA-vWF displayed strongly impaired botrocetin-binding to GpIbα corresponds to the low Ristocetin-cofactor activity that is reported for this protein (2.3 IU/mg protein). In contrast, PEG-vWF has a similar Ristocetin-cofactor activity compared to wt-vWF (41.0 IU/mg compared to 44.4 IU/mg, respectively). It is of importance to mention, however, that both assays are dependent on the activation of vWF by ristocetin or botrocetin. It cannot be excluded that pegylation and/or polysialylation of vWF affects the interaction with these activators. Conclusive data regarding the interaction between VWF and GpIba may be obtained from in vitro perfusion experiments.

Figure 7:
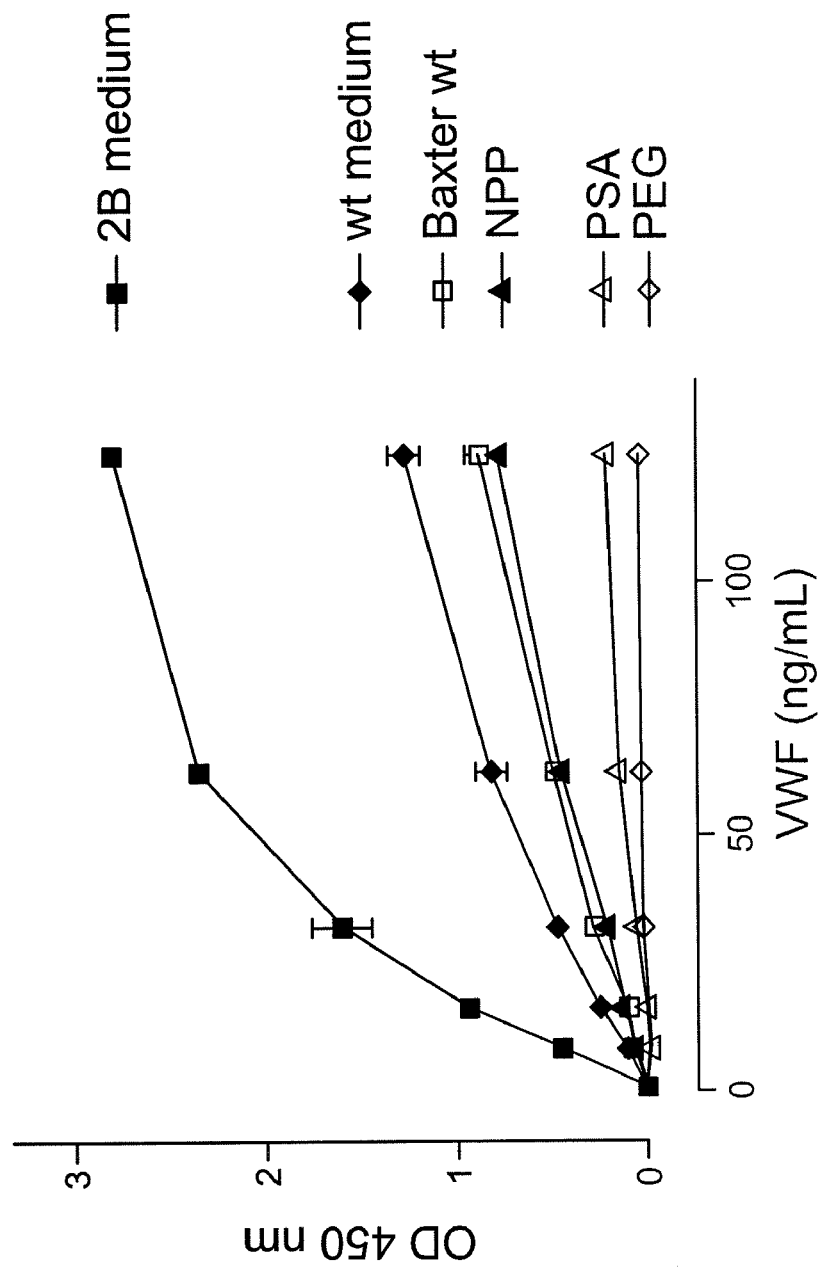
FIG. 7. Comparison of rVWF (wt), natural VWF (NPP), mutant rVWF (2B), and conjugated VWF binding to nanobody AU/vWFa-11. The binding of conjugated VWF to the nanobody is greatly reduced.

The results of AU/vWFa-11 binding experiments are given in FIG. 7. Normal pooled plasma (NPP) is used as a binding control reference, the slope of which is arbitrarily assigned as 1. As positive control, we have included recombinant vWF carrying an Arg1306Gln mutation (type 2B) which induces a platelet-binding conformation. The relative activity of this preparation (defined as the ratio's between the slopes of the preparation over the slope of normal pooled plasma) is 6.9. Recombinant wt-vWF from the University Medical Center Utrecht preparation displayed slightly enhanced binding to nanobody AU/vWFa-11 (relative activity 1.6), whereas recombinant wt-vWF provided by Baxter was similar to normal pooled plasma (relative activity 1.1). In contrast, both PEG-vWF and PSA-vWF displayed reduced binding to AU/vWFa-11 (relative activities 0.04 and 0.3, respectively). Usually, these types of reduced relative activities are found in vWF molecules carrying a type 2A mutation. Reduced biding to AU/vWFa-11 indicates that conjugation of vWF with PEG or PSA does not convert the molecule into an active, platelet binding conformation. Alternatively, conjugation of VWF may alter access of the nanobody to its binding site within the vWF A1 domain.

Example 3

The relationship between the half-life survival rate of FVIII in the presence and absence of VWF was studied in patients with Haemophilia A and Von Willebrand Disease type 3. Haemophilia A patients have a deficiency in FVIII levels, but typically display normal VWF expression. Conversely, patients with Von Willebrand Disease (VWD) type 3 are homozygous for deficient VWF, but show normal FVIII expression. However, despite the normal expression of FVIII in patients with Von Willebrand Disease type 3, plasma levels of the clotting factor are greatly reduced, presumably due to a lack of protection normally provided by stable binding of VWF to FVIII. Thus, it is predicted that administration of a FVIII concentrate to Haemophilia A patients will result in a longer half life of the clotting factor than will administration to patients with Von Willebrand Disease type 3.

Figure 8:
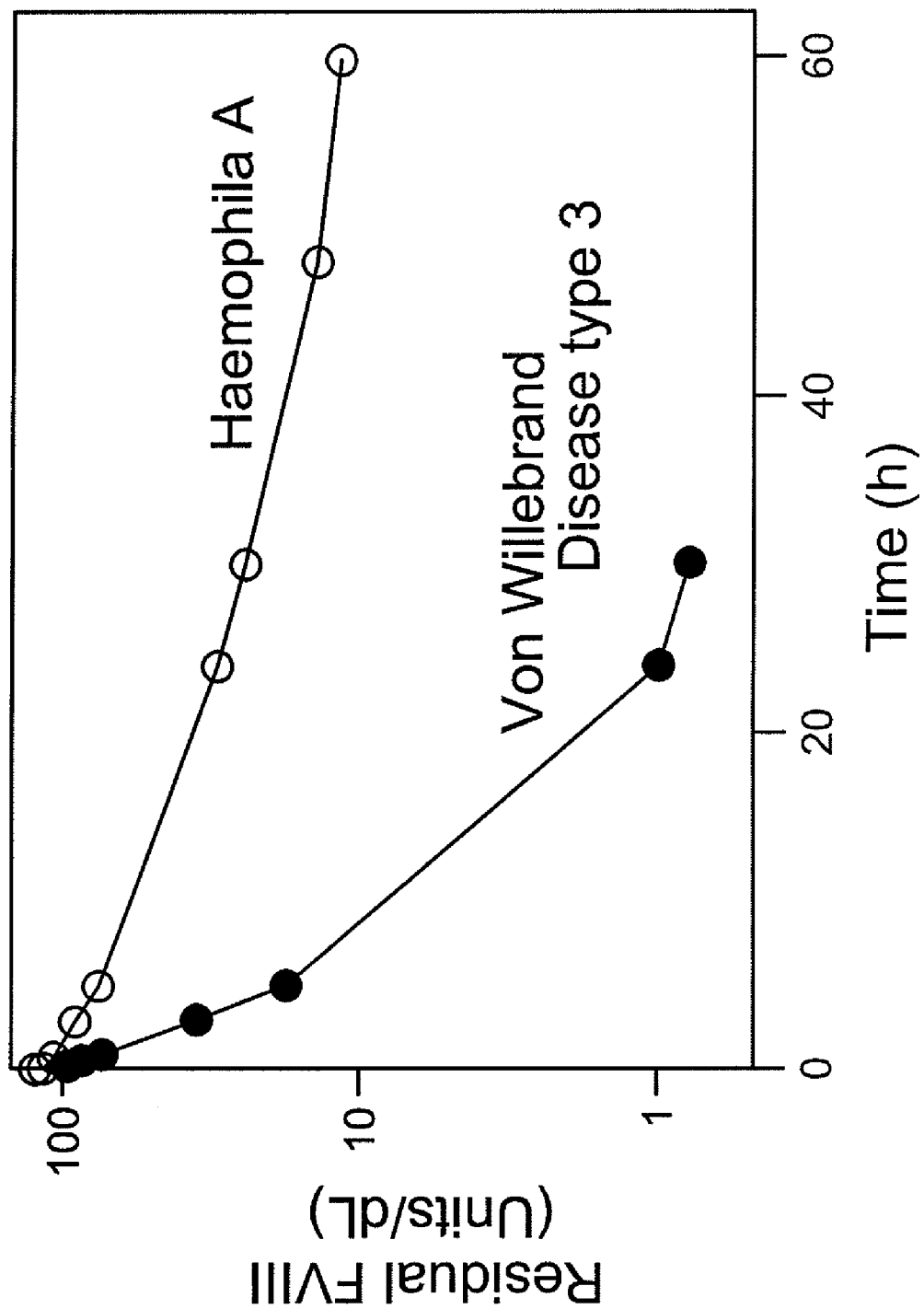
FIG. 8. Survival assays of recombinant FVIII administered to patients suffering from Haemophilia A and Von Willebrand Disease type 3. Administered rFVIII appears to be stabilized in Haemophilia A patients as compared to VWD type 3 patients presumably by the presence of functional vWF in the former.
Figure 9:
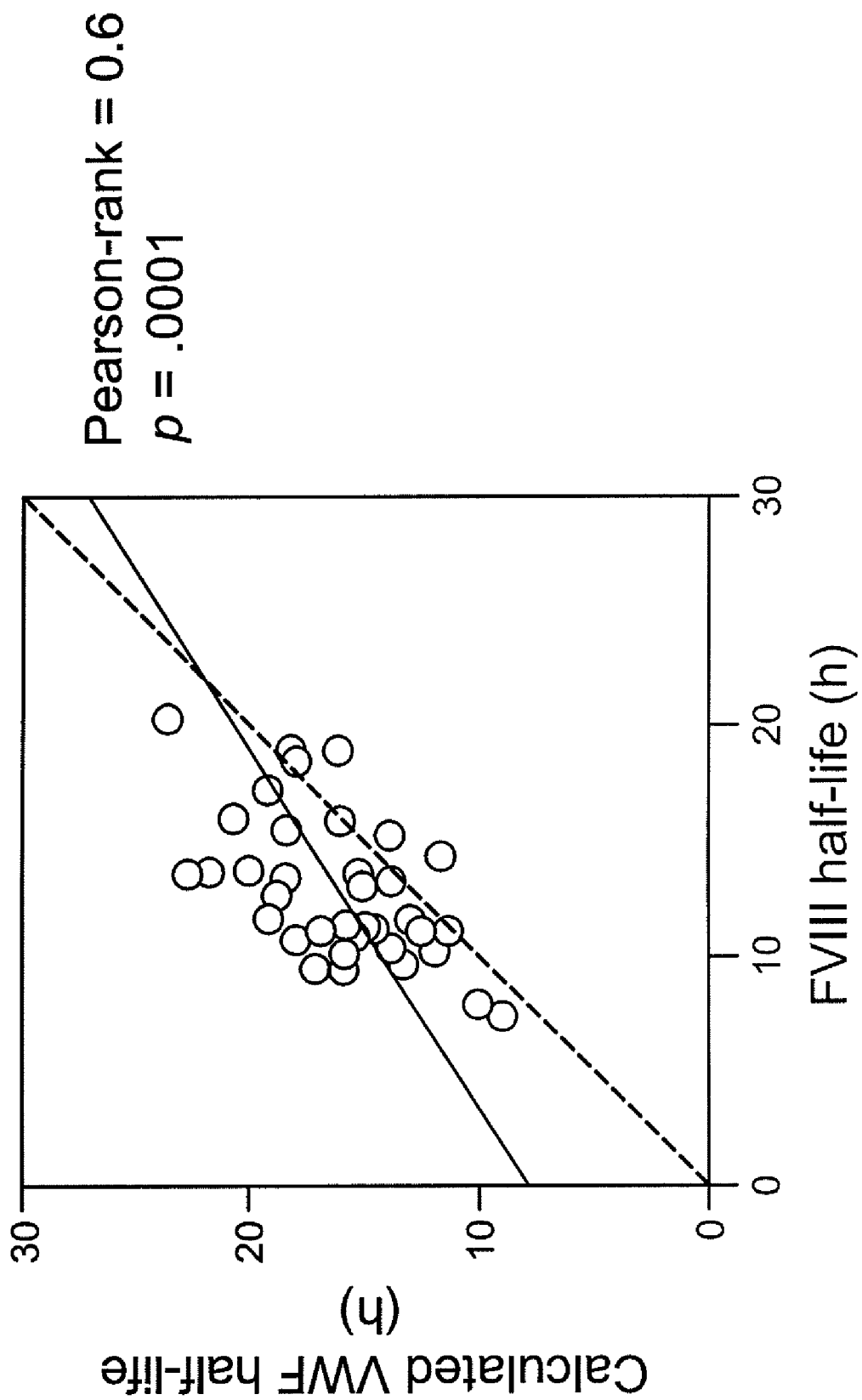
FIG. 9. Correlation between the calculated half-life of VWF and the half-life of administered rFVIII in Haemophilia A patients. It is noted that in 33 of 38 patients, the half-life of VWF is equal to or greater than the half-life of administered rFVIII.

The hypothesis presented above was tested by determining the survival rate of administered FVIII in Haemophilia A patients and in patients with VWD type 3. Briefly, 30 IU/kg b.w. of a Factor VIII concentrate (Advate, Baxter Healthcare Corp.) was administered to patients with Haemophilia A and VWD type 3. Blood samples were drawn, citrated plasma was prepared and FVIII levels were measured by ELISA (Asserachrom, Stago; Asnieres sur Seine, France), using a monoclonal antibody specific for FVIII, at different time points after administration. As can be seen in FIG. 8, the half life of administered FVIII in Haemophilia A patients is roughly 20 hours, while the half-life in patients with Von Willebrand Disease type 3 is only 1 to 2 hours. Thus, FVIII clearance in vivo occurs at a much greater rate in the absence of wild type VWF, as indicated by the lower half-life of FVIII administered to patients suffering from Von Willebrand Disease Type 3.

Figure 10:
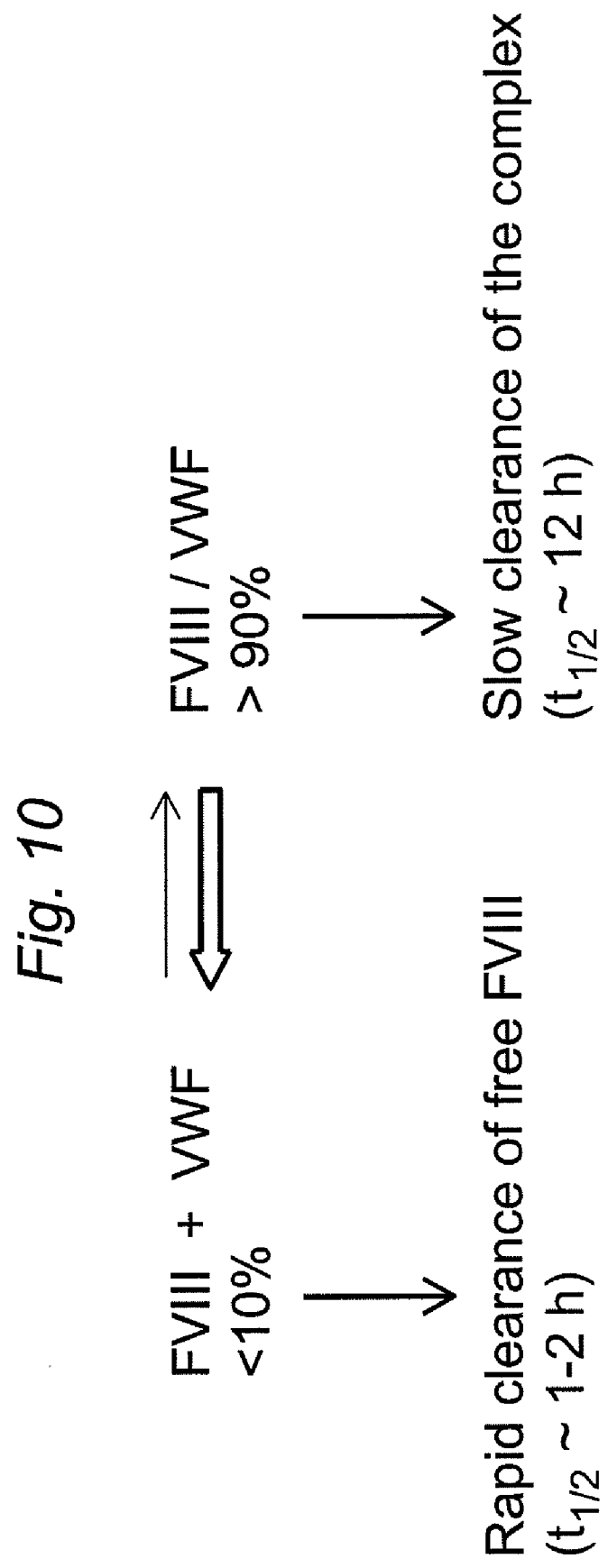
FIG. 10. Diagram of the equilibrium between free and VWF-bound FVIII in vivo.

Next, the relationship between the half-life of administered FVIII and VWF in Haemophilia A patients was determined. The half-life of VWF in the patients was calculated as proposed by Nossent et al. (*Journal of Thrombosis and Haemostasis*, 4(12):2556-62 (2006)). Specifically, it was assumed that the half-life, in hours, of VWF is equal to twice the ratio of the concentration of steady state VWF to the steady state concentration of the propeptide. In this fashion, the half-life was calculated in 38 severe Haemophilia A patients after administration of 30 IU FVIII/kg b.w. of a Factor VIII concentrate, by determining the plasma levels of VWF-antigen by ELISA using a polyclonal antibody specific for VWF (DAKO Cytomation, Glostrup, Denmark) and VWF propeptide levels by a specific monoclonal antibody (Sanquin Research; Amsterdam, NL). The determined half-lives of FVIII and VWF from the sample cohort were plotted and a Pearson-rank coefficient of 0.6 (P=0.0001) was found, indicating that the two half-lives are strongly correlated (FIG. F). Notably, in 33 of the 38 patients, the half-life of VWF was greater than the half-life of FVIII. A proposed equilibrium for FVIII clearance in vivo is shown in FIG. 10.

Example 4

Several receptors have been described as being putatively responsible for FVIII clearance in vivo, including LDL-receptor related protein (LRP1, CD91)/megalin (Lenting et al., *JBC* 274:23734-9 (1999); Saenko et al., *JBC* 274:37685-92)), LDL-receptor/vLDL-receptor Bovenschen et al., Blood 106: 906-12 (2005)), Asialoglycoprotein-receptor (Bovenschen et al., *J Thromb Haemost* 3:1257-65 (2005)), and CD206 (macrophage mannose-receptor) (Lenting et al, *J Thromb Haemost* 5:1353-60 (2007)). It is known that FVIII binding to these receptors is prevented or reduced in the presence of VWF. However, only LRP1 has been shown to be physiologically relevant for FVIII clearance (Bovenschen et al., *Blood* 101(10):3933-9 (2003)). Therefore, kinetic studies of the interaction between FVIII and LRP1 were undertaken in an attempt to determine conditions that result in reduced FVIII clearance via LRP1.

Figure 11:
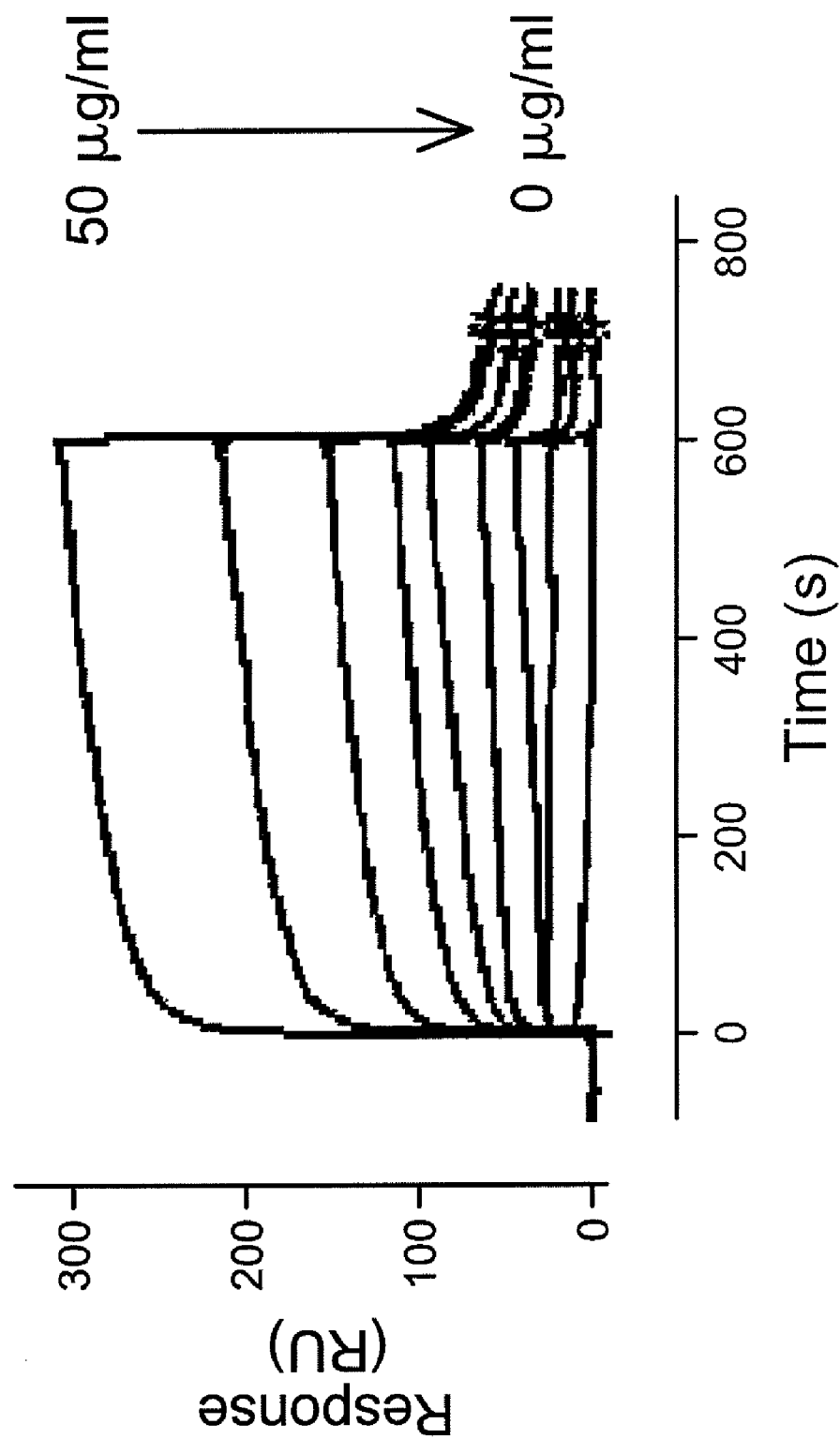
FIG. 11. SPR analysis of FVIII (0-50 μg) binding to immobilized LRP1.
Figure 12:
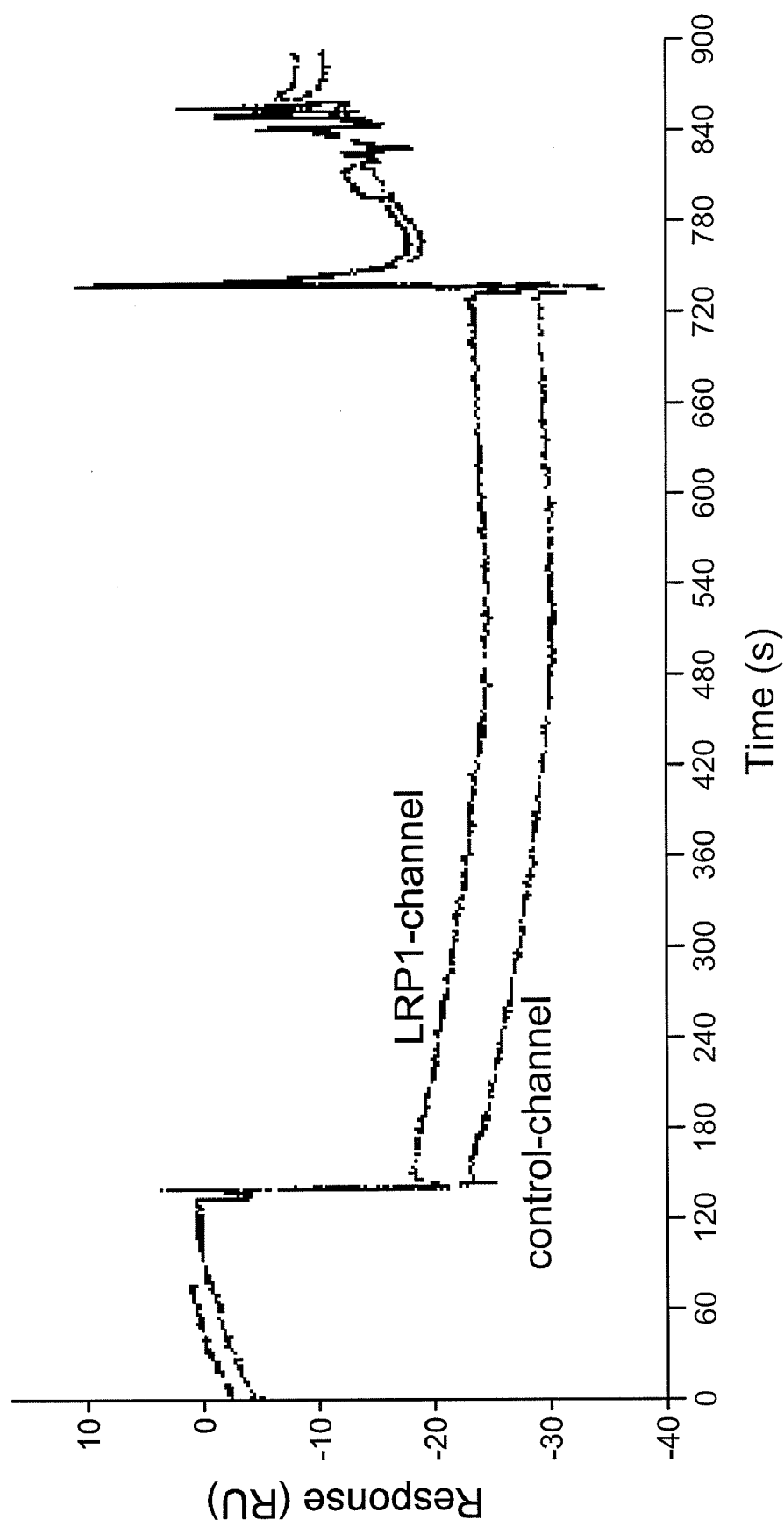
FIG. 12. SPR analysis of hPEGylated-FVIII (50 μg) binding to immobilized LRP1.
Figure 14:
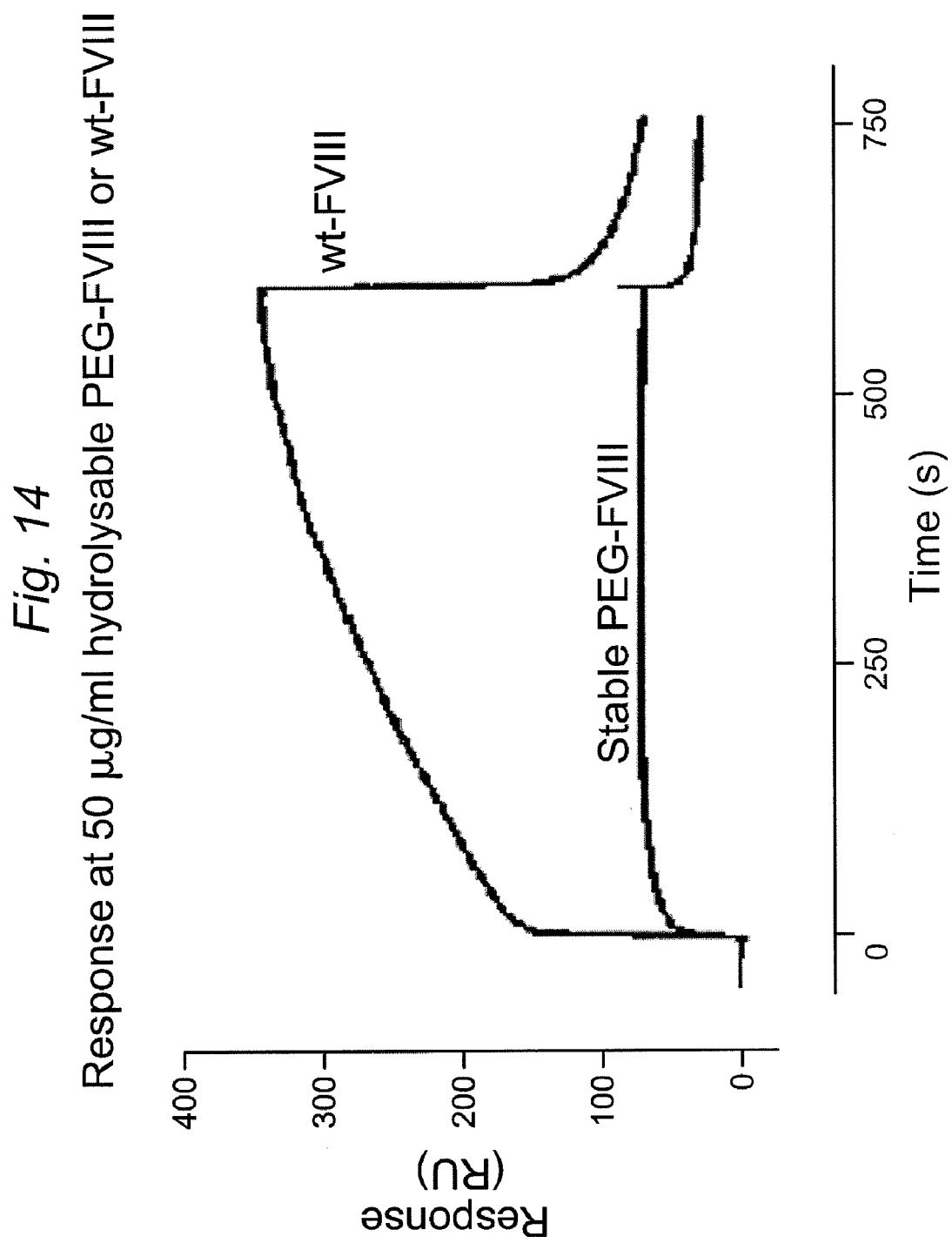
FIG. 14. SPR results comparing wt-rFVIII and hPEGylated-rFVIII binding (50 μg) to immobilized LRP1.

Surface Plasmon Resonance (SPR) experiments were carried out on the Biacore 2000 system to determine the effect that chemical conjugation and the presence of additional blood factors have on the kinetics of FVIII-LRP1 binding. Briefly, LRP1, purified as described by Huizinga et al. (*J Thromb Haemost* 3:2228-37 (2005), was immobilized onto a CM5 biosensor chip at 4000 RU/mm$^2$, which was determined to be approximately 6.7 fmol/mm$^2$ LRP1. Various concentrations of recombinant FVIII, PEGylated (FIG. 11) and non-conjugated (FIG. 12), were flowed over the chips at 20 μl/min, and steady state kinetics of the interaction were determined using a Biacore 2000 system and the BIAevaluation software. hPEGylated-FVIII was modified with a hydrolysable PEG moiety shown in FIG. 13, which was attached as described in US 2008/0234193 A1. As can be seen in FIG. 13, hPEGylated FVIII failed to bind LRP1, even at concentrations as high as 50 μg/ml. The experiments were then repeated with sPEGylated-FVIII, which was modified by a stable PEG moiety as shown in FIG. L. As seen in FIGS. 14 and 15, sPEGylated FVIII (open circles) bound to LRP1 at substantially reduced levels as compared to unmodified FVIII (closed circles). These experiments show that PEGylation of FVIII inhibits binding to LRP1.

Figure 16:
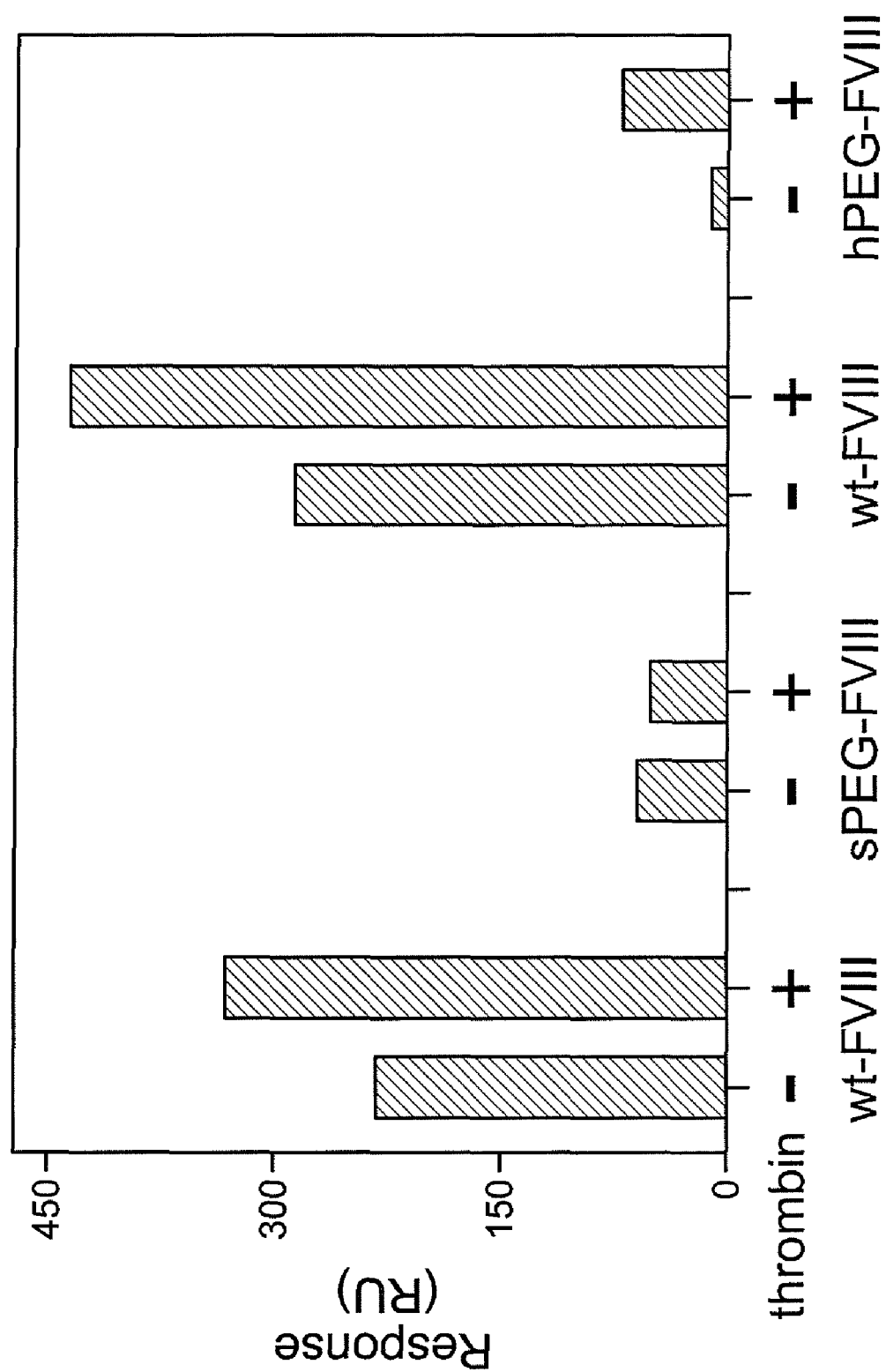
FIG. 16. Comparison of equilibrium LRP1 binding responses for wt and conjugated FVIII protein activated by thrombin cleavage. Results indicate that hPEGylated-, but not sPEGylated-, FVIII is induced to bind LRP1 upon thrombin activation (compare bars 7 and 8 to bars 3 and 4).

It is known that LRP1 interacts with FVIII light chain, but not to full-length FVIII heavy chain (Lenting et al., *JBC* 274(34):23734-9 (1999)). However, after partial proteolysis by thrombin, FVIII heavy chain becomes competent to bind to LRP1 (Bovenschen et al., *J Thromb Haemost.* 4(7):1487-93 (2006)). Thus, the effect of PEGylation on thrombin activated FVIII binding to LRP1 was investigated. Briefly, unmodified FVIII, hPEGylated-FVIII, and sPEGylated-FVIII at 250 μg/ml was incubated with 2 nM thrombin for 5 minutes at 37° C. To stop proteolysis, the reaction mixture was diluted 10-fold in 50 nM aqueous solution of a thrombin specific inhibitor (PPACK, Biomol Int., Germany). LRP1 binding of the activated FVIII solutions were than analyzed by SPR using a Biacore 2000 system as described before. As can be seen by results of the SPR FVIII binding experiments, shown in FIG. 16, thrombin cleavage induces LRP-binding of unmodified and hPEGylated-FVIII, but not sPEGylated-FVIII.

The effect of VWF on FVIII-LRP1 binding was next examined by SPR analysis. 40 nM unmodified FVIII was preincubated with 0 to 400 nM VWF, either unmodified or PEGylated, for 25 minutes at 37° C. VWF/FVIII complexes were then subjected to SPR analysis as above. Both sPEGylated (FIG. 17) and hPEGylated (FIG. 18) VWF further inhibited FVIII binding to LRP1 with respect to unmodified VWF. These data suggest that PEGylation of VWF can further reduce FVIII clearance via the LRP1 receptor.

In summary, the FVIII-LRP1 binding experiments show that PEGylation of FVIII strongly reduces the interaction between FVIII and its clearance receptor LRP1. Further, thrombin cleavage of hPEGylated-FVIII, but not sPEGylated-FVIII, induces binding to LRP1, although not to the same level as unmodified FVIII. Finally, PEGylation of VWF does not interfere with VWF mediated inhibition of the interaction between FVIII and its clearance receptor LRP1. Conversely, PEGylation actually increases VWF's inhibitory effect on FVIII binding to LRP1, as demonstrated. These experiments suggest that PEGylation of either or both of recombinant VWF and FVIII may have beneficial effects for administration in patients with blood clotting disorders such as Haemophilia and Von Willebrand Disease.

Example 5

Figure 19:
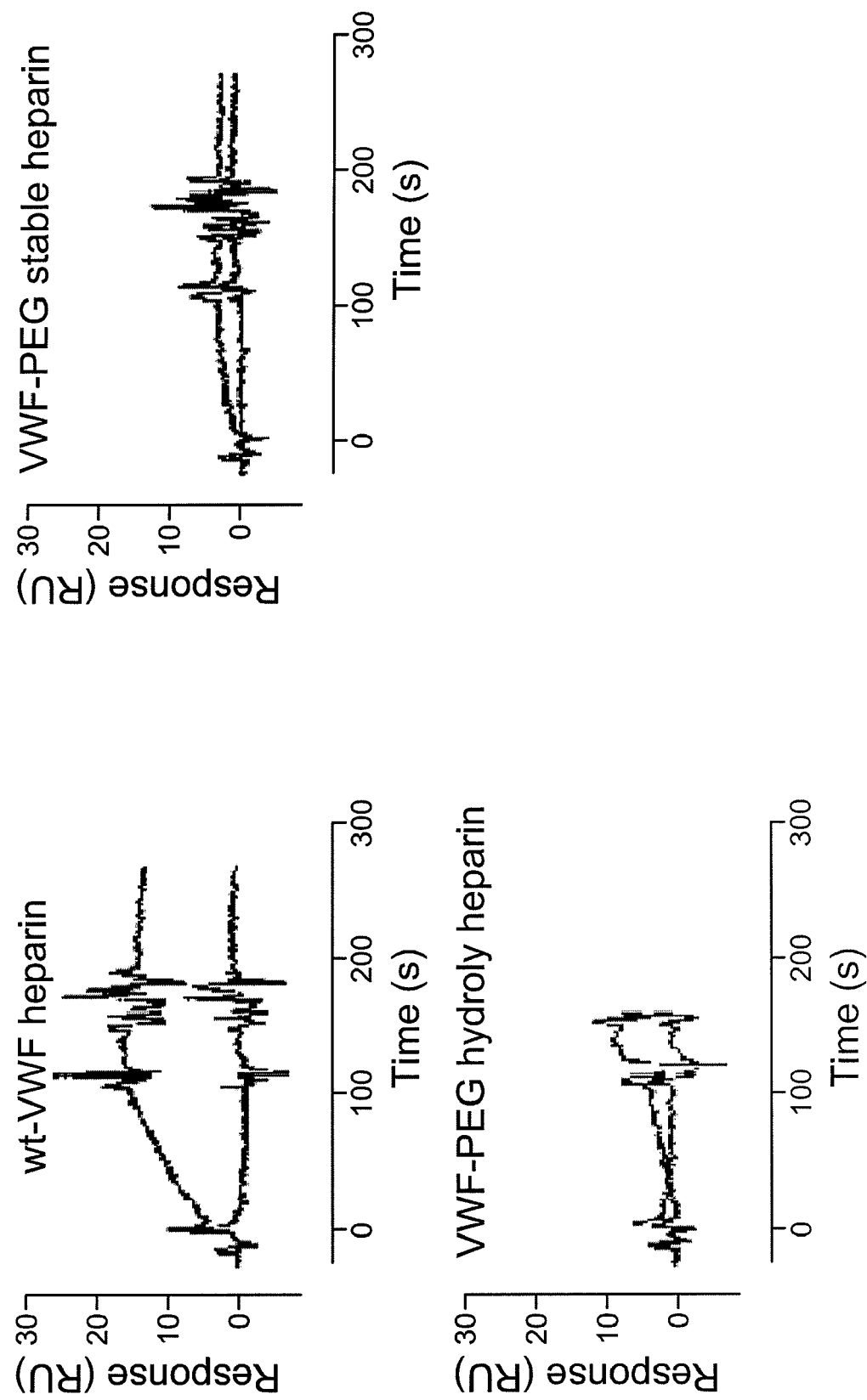
FIG. 19. SPR analysis of wt-VWF, hPEG-VWF, and sPEG-VWF binding to immobilized heparin.

To further characterize the effects of VWF PEGylation, SPR experiments were employed on a Biacore 2000 system to test the binding of conjugated VWF to heparin. Briefly, biotinylated heparin was conjugated to streptavidin coated sensorchips (GE Healthcare) at an RU/mm$^2$ of 70. 25 μg/ml non-conjugated, sPEGylated, and hPEGylated VWF, in buffer containing 20 mM HEPES (pH 7.4) and 100 mM NaCl, was then flowed over the chips at a flow rate of 10 μl/ml. As before data was collected and analyzed on a Biacore 2000 system (GE Healthcare) using the BIAevaluation software package. As seen in FIG. 19, non-conjugated VWF bound heparin with low affinity. This is in contrast to PEGylated VWF, which failed to bind heprin at all. These data suggest that PEGylation of VWF reduces or eliminates the proteins capacity to bind heparin.

Example 6

ELISA experiments were performed to determine the effect PEGylation has on VWF binding to GpIbα. Briefly, recombinant GpIbα was immobilized on antibody-conjugated microtiter plates and blocked with PBS-buffer, pH 7.4 containing 3% Bovine Serum Albumin (BSA) and 0.1% Tween 20. 0 to 500 ng/ml VWF from various sources was dialyzed into PBS-buffer containing 3% BSA and 0.1% Tween 20, and then incubated in the microtiter wells for 120 minutes at 37° C. Unbound protein was then removed and the wells were washed 3 times with washing buffer (PBS-buffer, pH 7.4 containing 0.1% Tween 20). VWF was detected using Horseradish Peroxidase (HRP) labeled polyclonal anti-VWF antibody (DAKO Cytomation). As seen in FIG. 6, PEGylated VWF bound GpIbα with slightly reduced affinity as compared to non-conjugated VWF. These results indicate that PEGylated-VWF is still competent for GpIbα-mediated platelet binding.

Example 7

Figure 20:
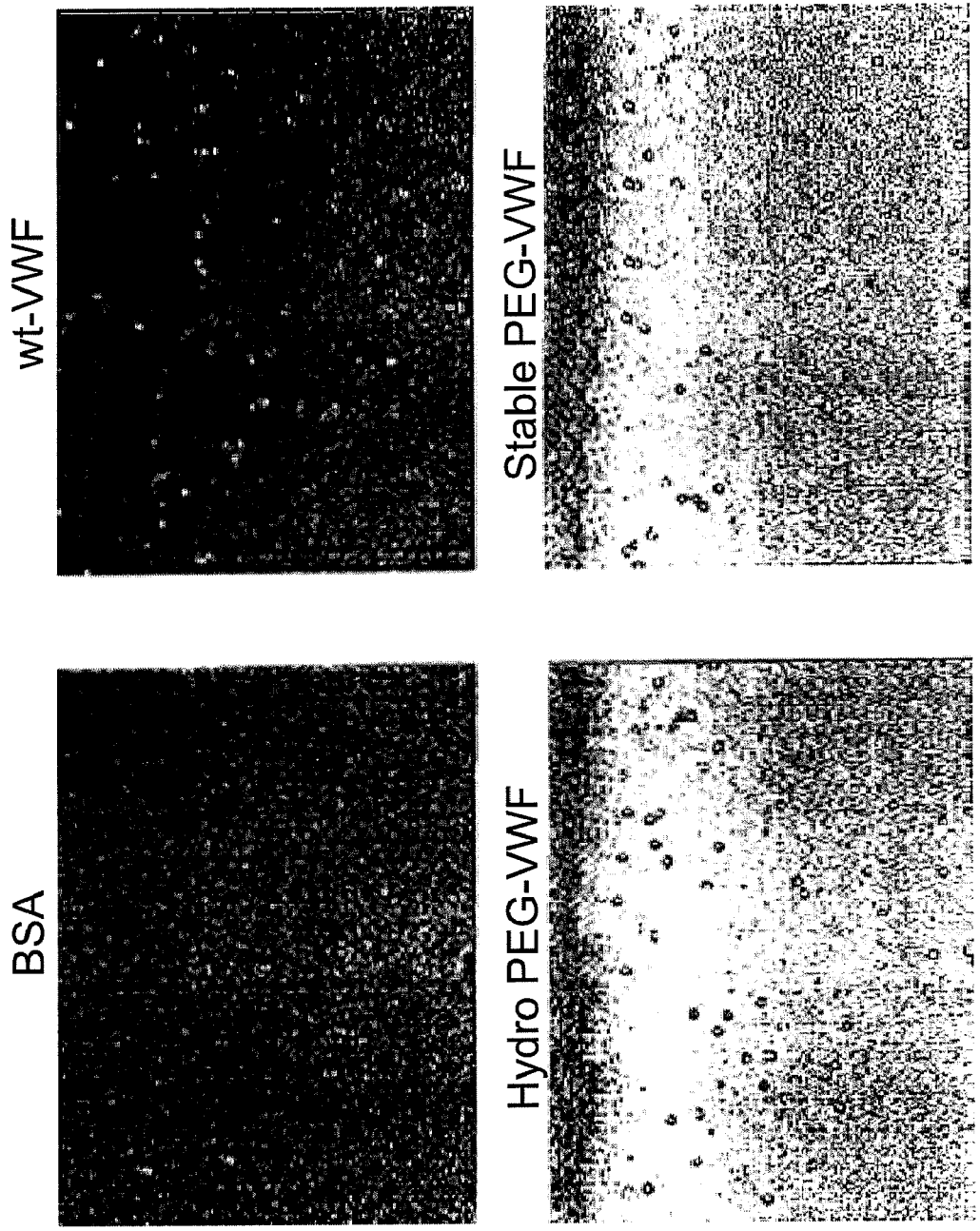
FIG. 20. Images of PMN static adhesion to immobilized wt and conjugated VWF.

VWF binds leukocytes under both perfusion and static conditions (Pendu et al, *Blood* 108(12):3746-52 (2006)). Static binding assays were performed to investigate the effect that PEGylation has on these interactions. Briefly, unmodified, hPEGylated, and sPEGylated VWF was immobilized in microtiter wells, PMN cells were then pre-treated, subsequently added to the protein coated wells, and incubated for 60 minutes at 37° C. (Pendu et al., *Blood* 108(12):3746-52 (2006)) Unbound cells were then removed by gentle washing of the wells with PBS—buffer, pH 7.4. As can be seen in FIG. 20, both sPEGylated and hPEGylated-VWF stably bound PMN cells at similar levels as non-conjugated VWF, under static conditions. This data indicates that conjugation of VWF does not affect specific interactions with leukocytes.

Example 9

Figure 21:
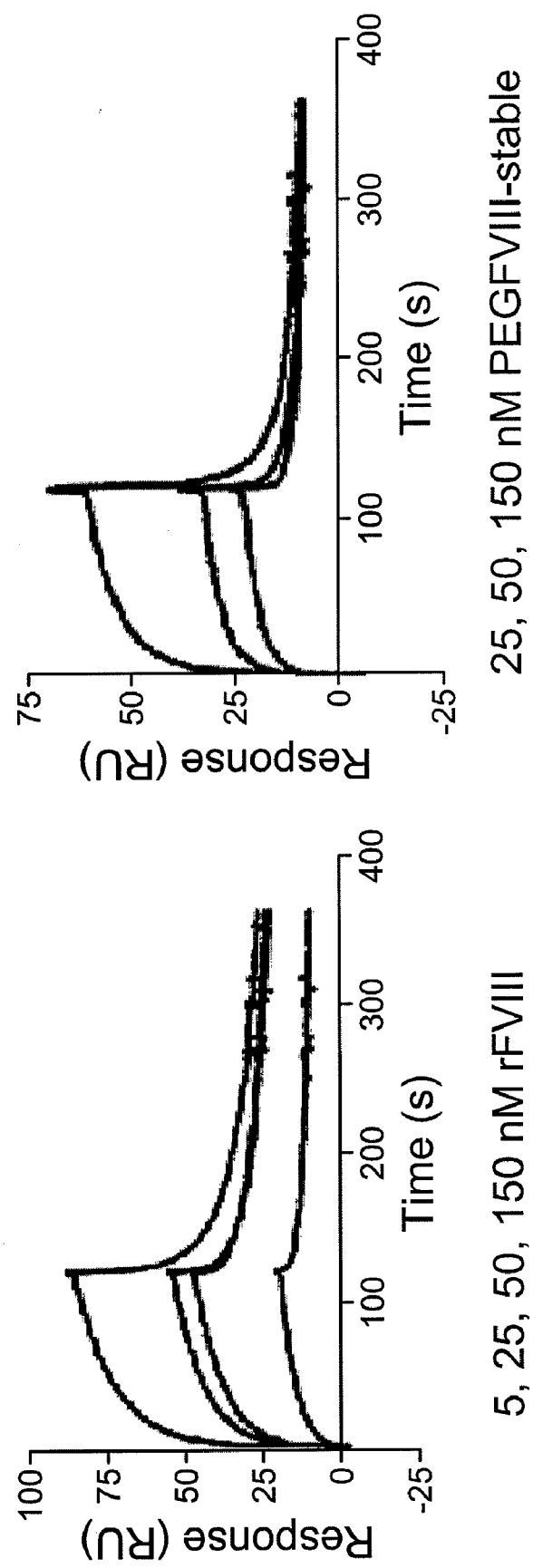
FIG. 21. SPR analysis of FVIII and sPEG-FVIII binding to immobilized LRP1.
Figure 22:
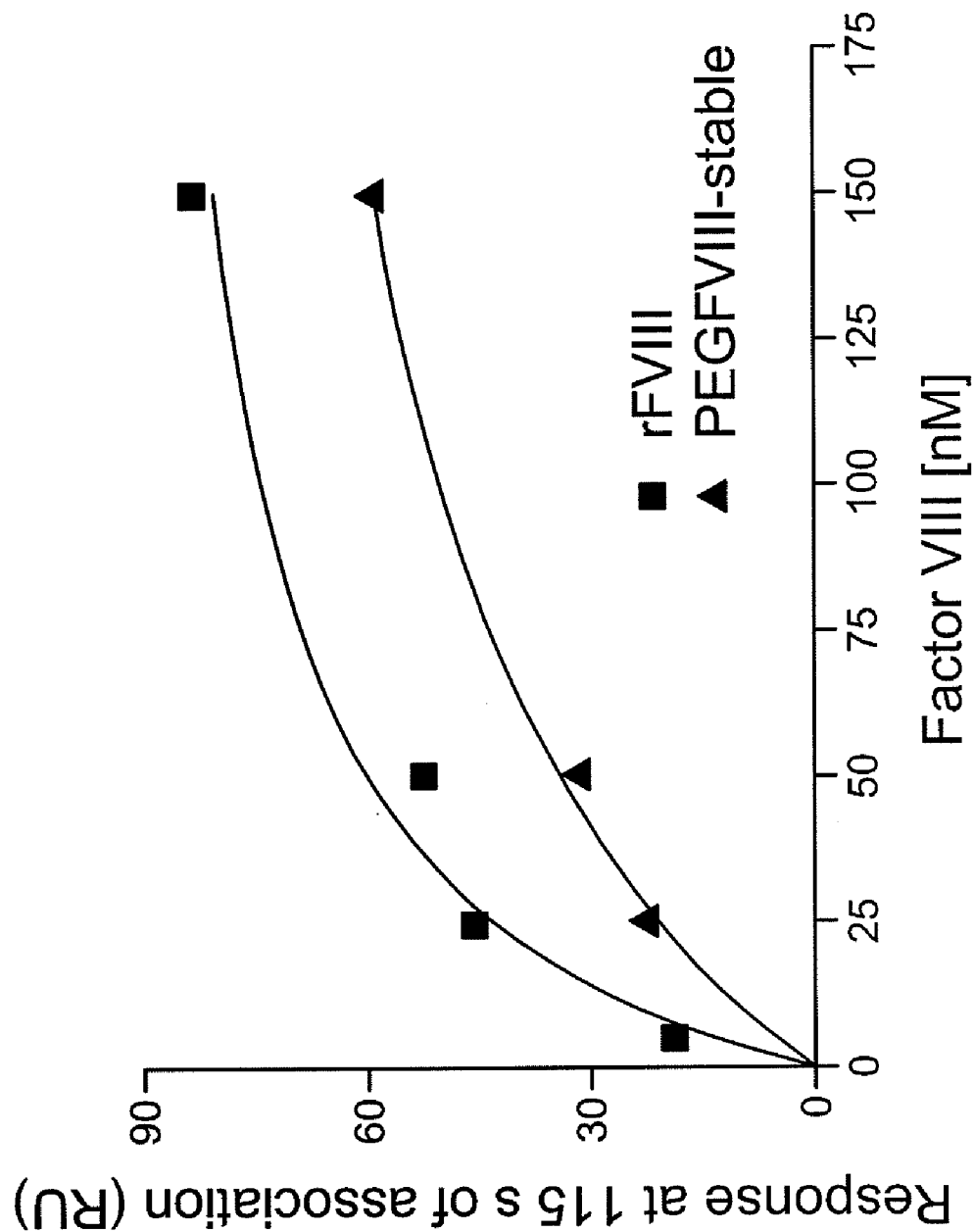
FIG. 22. Comparison of FVIII and sPEG-FVIII (0-150 nM) binding to immobilized LRP1 as determined by SPR analysis.
Figure 23:
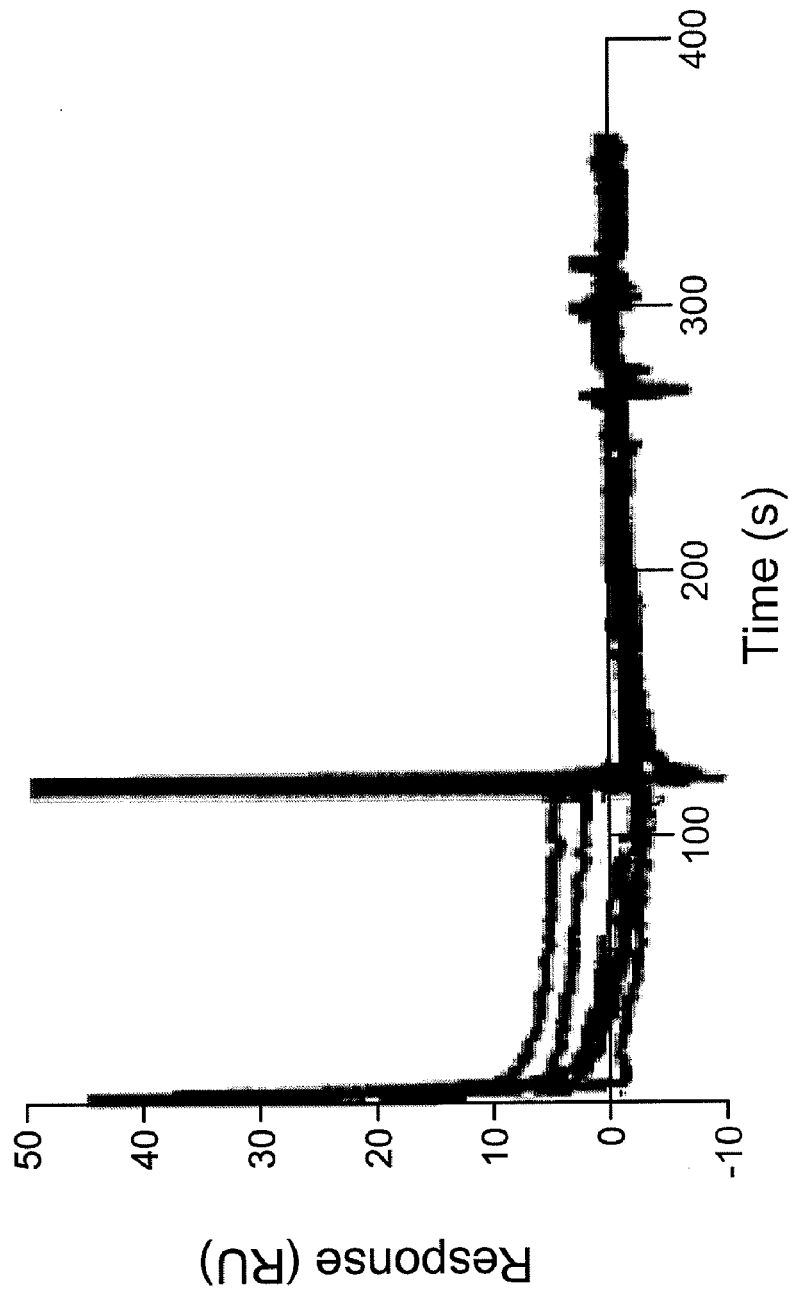
FIG. 23. SPR analysis of hPEG-FVIII binding to immobilized LRP1.
Figure 24:
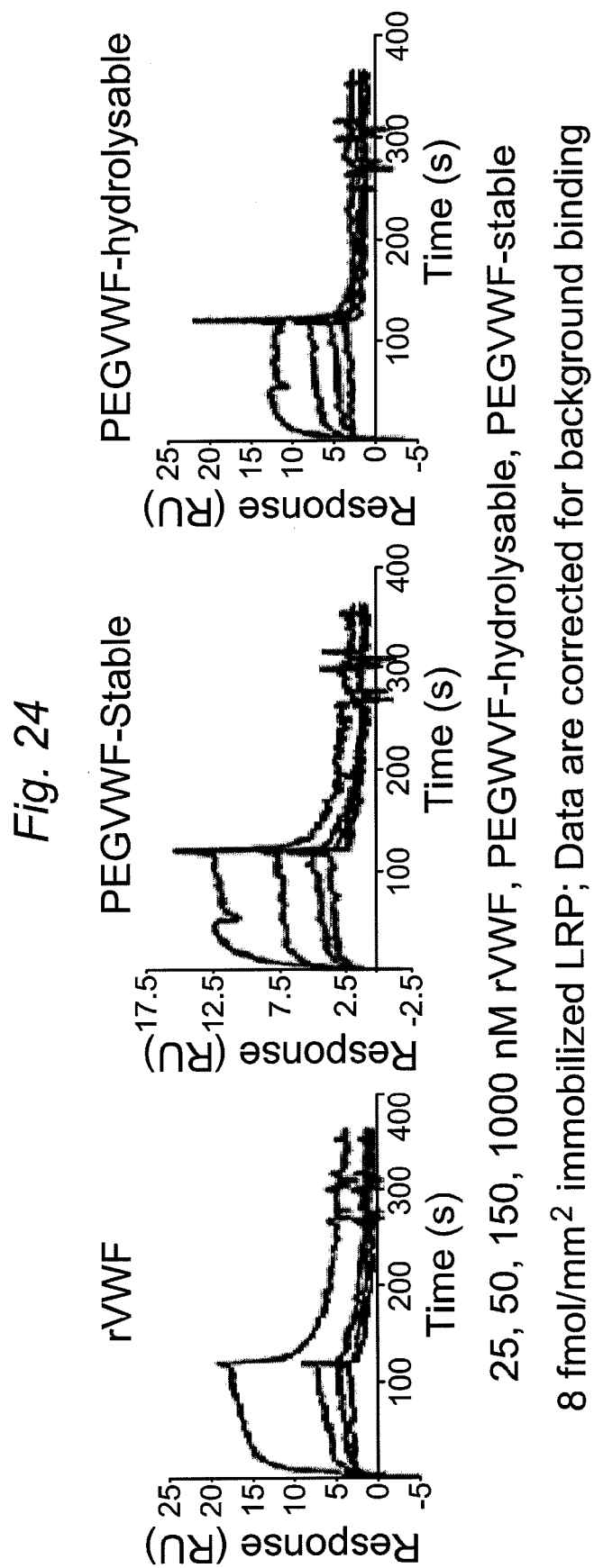
FIG. 24. SPR analysis of wt and conjugated VWF binding to immobilized LRP1.
Figure 25:
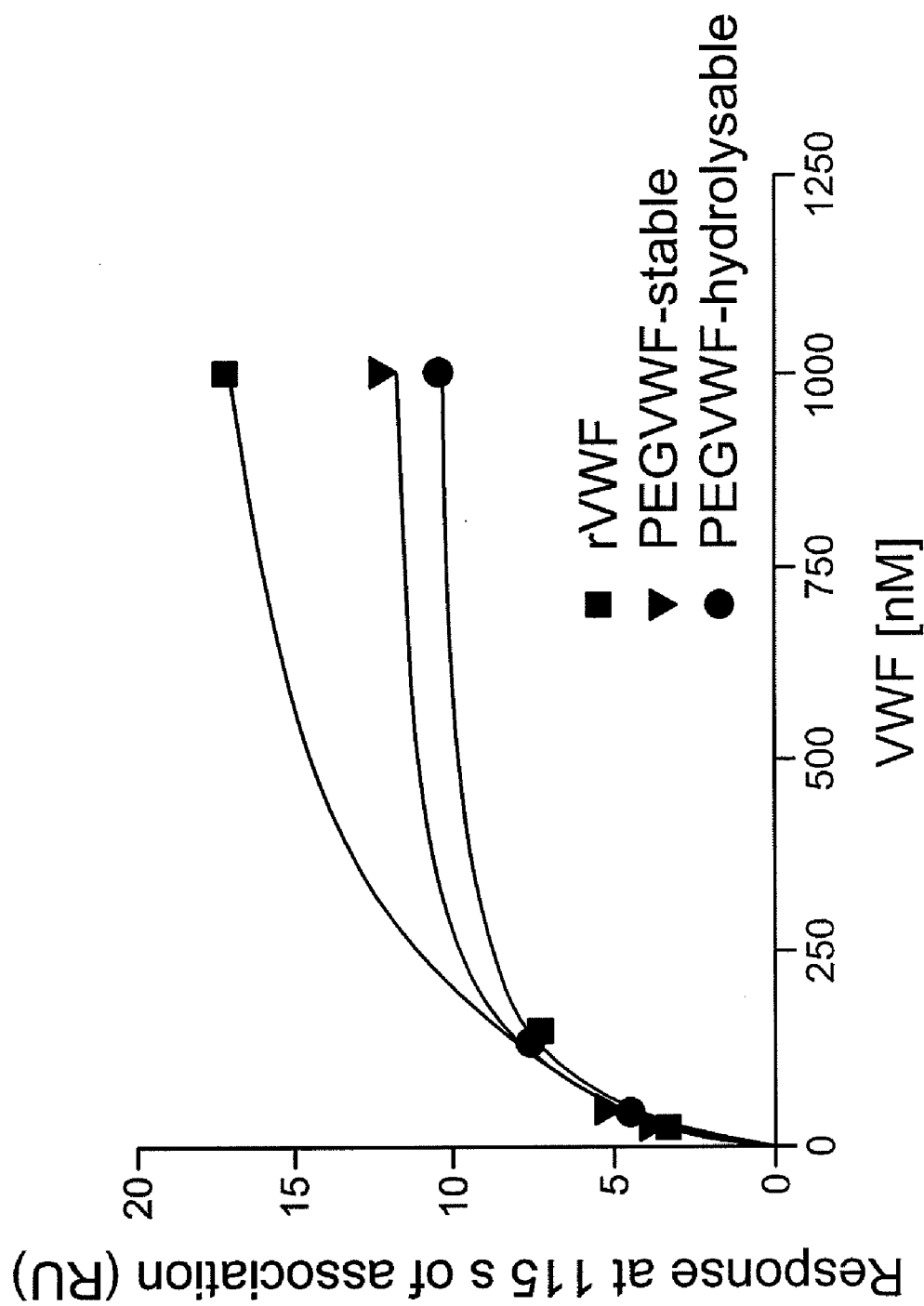
FIG. 25. Comparison of wt and conjugated VWF (0-1000 nM) binding to immobilized LRP1 as determined by SPR analysis.

To characterize the effect that PEGylation has on interactions between FVIII/VWF and LRP1, SPR experiments were performed. Briefly, LRP1 was conjugated to CM5-biosensor chips (Biacore Life Sciences) as before, and the conjugation was measured at approximately 8 fmol/mm$^2$ LPR1. Various concentrations of both conjugated and non-conjugated VWF and FVIII were diluted with 20 mM Hepes buffer (pH 6.5) containing 150 mM NaCl, 2 mM CaCl$_2$ and 0.005% (v/v) Tween 20. Protein samples were then flowed over the chips at 20 μL/min and equilibrium kinetics determined using a Biacore 2000 system employing the BIAevaluation software. As seen previously, sPEGylated-FVIII bound to LRP1 with reduced affinity as compared to non-conjugated FVIII (FIGS. 21 and 22), and hPEGylated-FVIII failed to bind LRP1 at all (FIG. 23). Surprisingly, it was found that both non-conjugated and PEGylated-VWF also bound to LRP1, although at a much lower affinity than FVIII (FIGS. 24 and 25). PEGylated-VWF bound to LRP1 with roughly half the affinity of the non-conjugated protein. These data show that the affinity of both FVIII and VWF for the clearance receptor LRP1 is reduced by conjugation of PEG to the blood clotting factors. Taken together, this suggests that PEGylation of FVIII and/or VWF will raise the in vivo half-live of said proteins administered to patients suffering from a blood clotting disorder, such as Haemophilia and Von Willebrand Disease, as these modified factors demonstrate reduced affinity for the LRP1 clearance receptor.

Example 10

Figure 26:
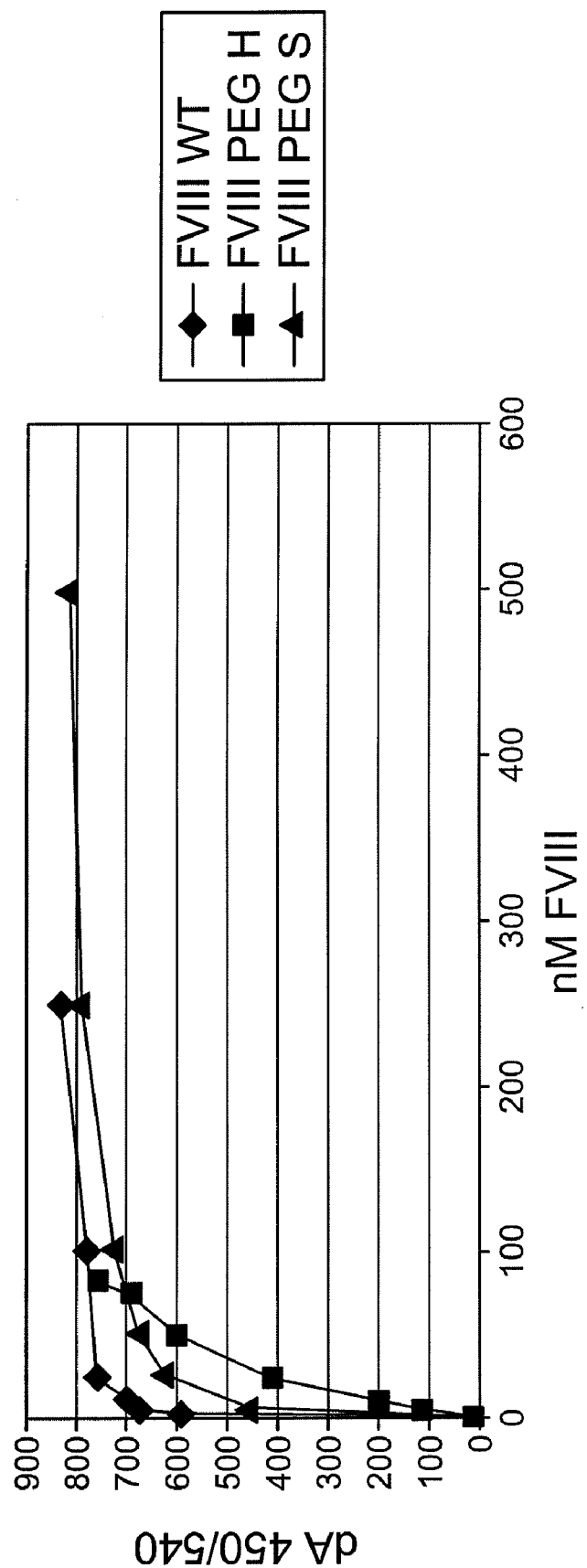
FIG. 26. Results of ELISA experiments comparing wt-FVIII and conjugated FVIII binding to cluster II of LRP1.
Figure 27:
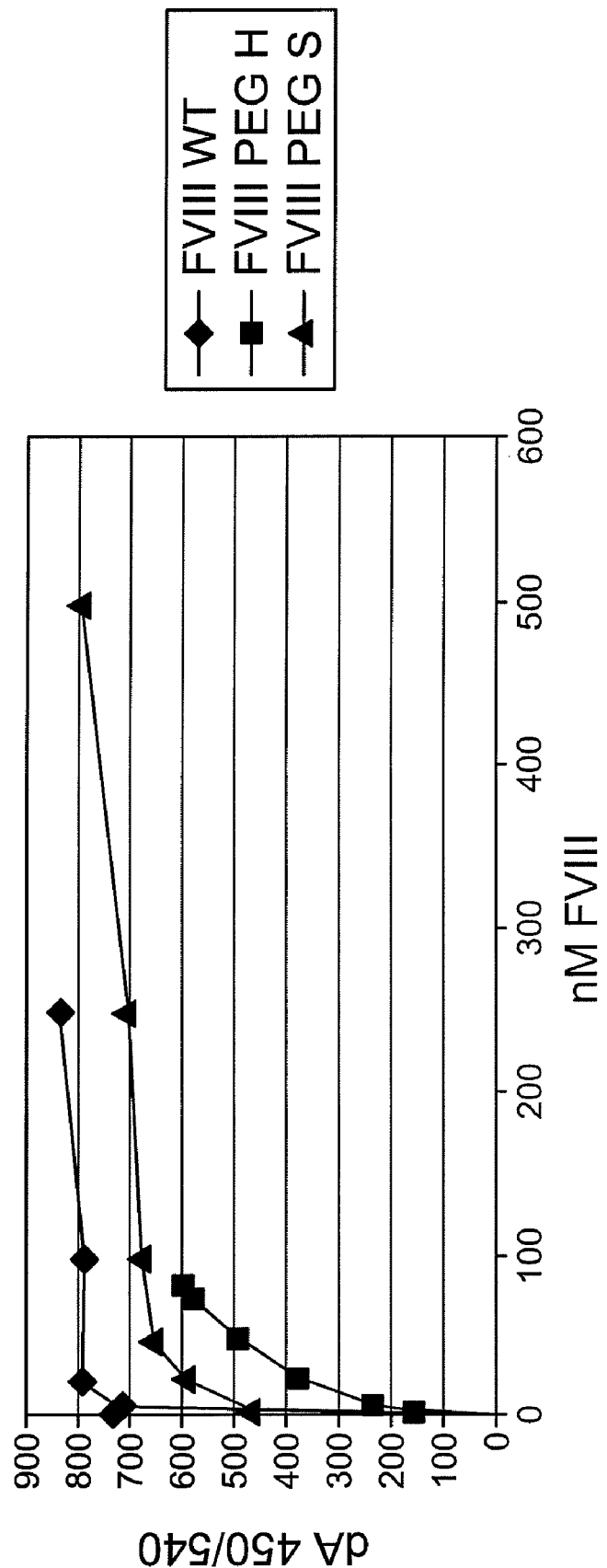
FIG. 27. Results of ELISA experiments comparing wt-FVIII and conjugated FVIII binding to cluster IV of LRP1.
Figure 28:
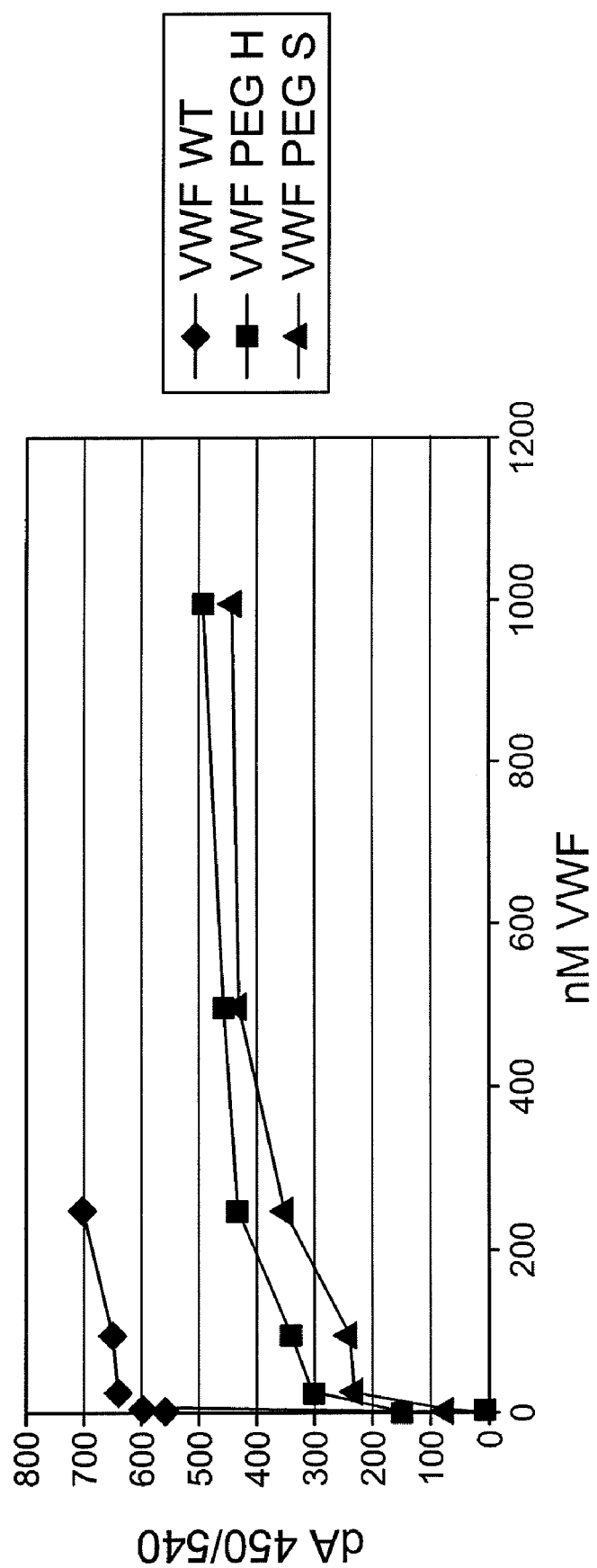
FIG. 28. Results of ELISA experiments comparing wt-VWF and conjugated VWF binding to cluster II of LRP1.
Figure 29:
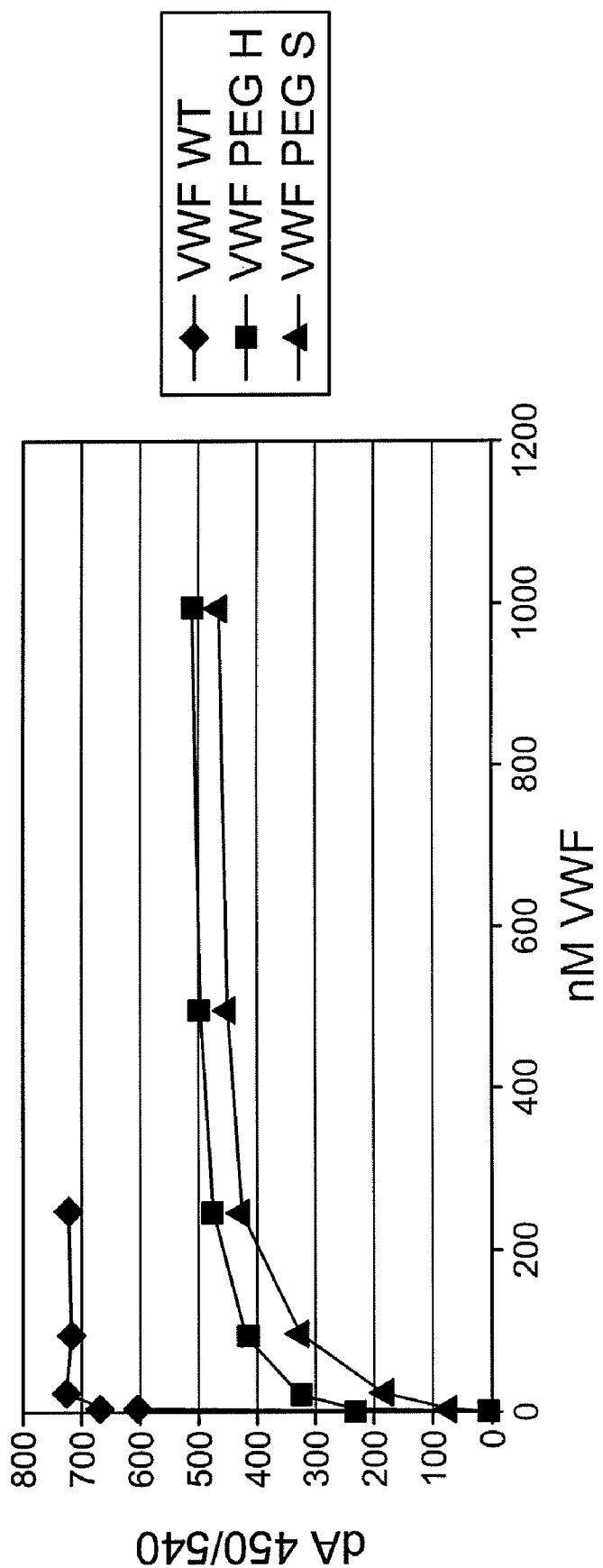
FIG. 29. Results of ELISA experiments comparing wt-VWF and conjugated VWF binding to cluster IV of LRP1.

It is widely accepted that different clusters in the extracellular domain of LRP1 bind with different affinities to different substrates (Willnow et al., *JBC* 269(22): 15827-32 (1994)). Particularly, it is though that cluster II and IV demonstrate the highest binding promiscuity and therefore likely contribute to the binding affinity for blood factors such as FVIII and VWF. In order to characterize the interactions between FVIII/VWF and LRP1, with respect to individual LRP1 clusters, ELISA experiments were performed comparing the binding affinities of conjugated and non-conjugated blood factors to clusters II and IV of LRP1. Briefly, recombinant cluster II or cluster IV peptides were immobilized in microtiter wells and blocked with Tris/NaCl buffer, pH 7.4 (50 mM Tris, 150 mM NaCl, 5 mM $CaCl_2$, 1% HSA, 0.1% Tween 20). Conjugated and non-conjugated FVIII and VWF was dialyzed into the same Tris/NaCl buffer, pH 7.4. The blood factors were then incubated in the microtiter wells for 120 minutes at 37° C. Unbound protein was removed and the wells were washed 3 times with Tris/NaCl buffer, pH 7.4. Bound FVIII or VWF was detected with HRP-labeled FVIII monoclonal antibody (Lenting et al., JBC 269:7150-5 (1994). or HRP-labeled VWF polyclonal antibody (DAKO Cytomation). As seen in FIGS. 26 and 27, conjugated and non-conjugated FVIII, bound to both LRP1 clusters II and IV. Consistent with the SPR data, conjugated FVIII consistently bound to the LRP1 clusters with reduced affinity as compared to the non-conjugated protein. Similarly, conjugated and non-conjugated VWF also bound to both LRP1 clusters. Again, consistent with the SPR results, PEGylated-VWF reproducibly bound with significantly reduced affinity to both clusters II and IV.

Example 11

The present example demonstrates conjugation of rFVIII with PSA using the MAL-FMS-OSU-linker. For preparation of rFVIII-PSA conjugate, 6 ml of a solution of recombinant FVIII (4.5 mg/ml) derived from the Advate manufacturing process in 20 mM Hepes buffer, pH 7.4 the bifunctional linker MAL-FMS-OSU (prepared as outlined by Tsubery et al., JBC 2004; 279:38118-24) was added (concentration: 0.315 mg/mg protein) and incubated at R.T. for 30 min. Then derivatized PSA containing a terminal SH group was prepared. The PSA derivative was added to the mixture (concentration: 27.8 mg PSA-SH/mg protein—450 fold molar excess) and incubated for additional 2 hours at R.T. The reaction was stopped by adding an aqueous solution of 0.1 M glycine (final concentration 10 mM) and 5 mM cysteine (end concentration 0.5 mM). The free reagents were separated from the rFIX-PSA conjugate by Hydrophobic Interaction Chromatography using a prepacked Butyl Sepharose column (HiTrap Butyl FF 5 ml, GE Healthcare). A buffer containing 5 M NaCl (50 mM Hepes-buffer, 5M NaCl, 0.01% Tween 80, 6.7 mM $CaCl_2$, pH 6.9) was added to the PSA-rFIX containing solution to give a final concentration of 3M NaCl. Then this mixture is applied to the column, which was subsequently washed with 10 CV equilibration buffer (50 mM Hepesbuffer, 3M NaCl, 0.1% Tween 80, 5 mM $CaCl_2$, pH 6.9) and the elution of the rFIX-PSA conjugate was carried out with Citrate buffer, pH 7.4 (13.6 mM $Na_3$Citrate, 20 mM $CaCl_2$, 20 mM Histidine, 0.01% Tween 80). After elution of the conjugate the pH was adjusted to pH 6.9. The eluate contained 2.5 mg/ml protein (BCA assay).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of increasing the survival of Factor VIII by inhibiting interaction of actor VIII with a clearance receptor, the method comprising the steps of:
   (a) modifying a coagulation protein with a water soluble polymer, wherein the coagulation protein is von Willebrand Factor, and
   (b) administering to a mammal in need thereof a therapeutically effective amount of a composition comprising the modified coagulation factor;
   wherein the modification increases the survival of the protein in the blood circulation of a mammal.

2. The method of claim 1, wherein the clearance receptor is LRP1.

3. The method of claim 1, wherein the water soluble polymer is selected from the group consisting of polysialic acid and polyethylene glycol.

4. The method of claim 1, wherein the water soluble polymer is releasable from the coagulation protein.

5. The method of claim 1, wherein the water soluble polymer is stably linked to the coagulation protein.

6. The method of claim 1, wherein the water soluble polymer is linked to the protein via a linker.

7. The method of claim 1, wherein Factor VIII is administered with the modified von Willebrand Factor.

8. The method of claim 7, wherein the Factor VIII being administered is also modified with a water soluble polymer.

9. A method of treating an individual with a blood, clotting disease or a disease characterized by a Factor VII deficiency, the method comprising administering to a patient suffering from a blood clotting disease von Willebrand Factor modified with a water soluble polymer, wherein said modified c von Willebrand Factor reduces binding affinity of Factor VIII for its clearance receptor.

10. The method of claim 9, wherein said water soluble polymer is selected from the group consisting of polysialic acid and polyethylene glycol.

11. The method of claim 9, wherein the clearance receptor is LRP1.

12. The method of claim 9, wherein the blood clotting disease is selected from the group consisting of Haemophelia and von Willebrand Disease.

13. The method of claim 9, wherein said method further comprises administering FVIII to the individual.

14. The method of claim 13, wherein said FVIII is not conjugated to a water soluble polymer.

15. The method of claim 13, wherein said FVIII is conjugated to a water soluble polymer.

\* \* \* \* \*

UNITED STATES PATENT AND TRADEMARK OFFICE
CERTIFICATE OF CORRECTION

PATENT NO. : 8,173,597 B2  
APPLICATION NO. : 12/267491  
DATED : May 8, 2012  
INVENTOR(S) : Hans-Peter Schwarz and Peter Turecek Page 1 of 1

It is certified that error appears in the above-identified patent and that said Letters Patent is hereby corrected as shown below:

Col. 36, Claim 1, Line 22: delete "actor" and replace it with --Factor--

Col. 36, Claim 9, Line 46: delete "," after blood

Col. 36, Claim 9, Line 47: delete "VII" and replace it with --VIII--

Col. 36, Claim 9, Line 50: delete "c" after modified

Signed and Sealed this
Nineteenth Day of June, 2012

David J. Kappos
*Director of the United States Patent and Trademark Office*